US012617790B2

(12) United States Patent
Pasternak et al.

(10) Patent No.: US 12,617,790 B2
(45) Date of Patent: May 5, 2026

(54) MITRAGYNINE ANALOGS AND USES THEREOF

(71) Applicant: Memorial Sloan-Kettering Cancer Center, New York, NY (US)

(72) Inventors: Gavril Pasternak, New York, NY (US); Susruta Majumdar, Stamford, CT (US); Rashad Karimov, Berkeley, CA (US); Andras Varadi, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 810 days.

(21) Appl. No.: 17/304,713

(22) Filed: Jun. 24, 2021

(65) Prior Publication Data

US 2022/0024923 A1 Jan. 27, 2022

Related U.S. Application Data

(62) Division of application No. 15/570,308, filed as application No. PCT/US2016/030305 on Apr. 29, 2016, now Pat. No. 11,046,692.

(Continued)

(51) Int. Cl.
*C07D 471/14* (2006.01)
*A61K 31/438* (2006.01)
(Continued)

(52) U.S. Cl.
CPC .......... *C07D 471/14* (2013.01); *A61K 31/438* (2013.01); *A61K 45/06* (2013.01);
(Continued)

(58) Field of Classification Search
CPC ..... C07D 471/14; C07D 471/20; A61P 25/00; A61P 25/04; A61P 25/18; A61P 29/00
See application file for complete search history.

(56) References Cited

U.S. PATENT DOCUMENTS 5,739,145 A 4/1998 Nagase et al.
5,834,478 A 11/1998 Ito
(Continued)

FOREIGN PATENT DOCUMENTS

EP 1746097 A1 1/2007
EP 1762569 A1 3/2007
(Continued)

OTHER PUBLICATIONS

Yamamoto et al., "Opioid receptor agonistic characteristics of mitragynine pseudoindoxyl in comparison with mitragynine derived from Thai medicinal plant Mitragyna speciosa" Gen Pharmacol. 1999, 33(1), 73-81. (Year: 1999).*

(Continued)

*Primary Examiner* — Kamal A Saeed
*Assistant Examiner* — Sagar Patel
(74) *Attorney, Agent, or Firm* — Foley Hoag LLP; DeAnn F. Smith; Lawrence P. Tardibono

(57) ABSTRACT

Described herein are compounds of Formulae (I')-(II'), compounds of Formulae (I)-(II) and pharmaceutically acceptable salts thereof. Compounds of the present invention are useful for modulating opioid receptor activity. The provided compounds may have both agonistic and antagonistic effect on one or more opioid receptors. Methods of using the compounds for treating or managing pain are also described.

(I')

(I)

(II')

(Continued)

-continued (II)

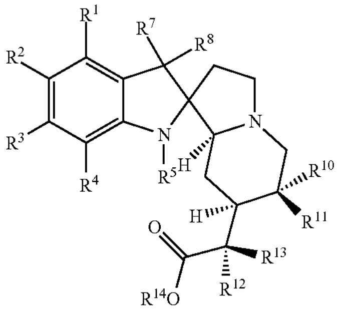

37 Claims, 17 Drawing Sheets

Specification includes a Sequence Listing.

Related U.S. Application Data

(60) Provisional application No. 62/155,248, filed on Apr. 30, 2015.

(51) Int. Cl.

| | |
|---|---|
| ***A61K 45/06*** | (2006.01) |
| ***A61P 25/00*** | (2006.01) |
| ***A61P 25/04*** | (2006.01) |
| ***A61P 25/18*** | (2006.01) |
| ***A61P 29/00*** | (2006.01) |
| ***C07D 471/20*** | (2006.01) |

(52) U.S. Cl.

CPC ............... *A61P 25/00* (2018.01); *A61P 25/04* (2018.01); *A61P 25/18* (2018.01); *A61P 29/00* (2018.01); *C07D 471/20* (2013.01)

(56) References Cited

U.S. PATENT DOCUMENTS

| | | | | |
|---|---|---|---|---|
| 6,147,084 | A | 11/2000 | Nagase et al. | |
| 6,177,438 | B1 | 1/2001 | Nagase et al. | |
| 6,323,212 | B1 | 11/2001 | Nagase et al. | |
| 6,583,151 | B2 | 6/2003 | Nagase et al. | |
| 8,338,442 | B2 | 12/2012 | Kumagai et al. | |
| 8,420,662 | B2 | 4/2013 | Takaki et al. | |
| 8,481,501 | B2 | 7/2013 | Cashman et al. | |
| 8,637,539 | B2 | 1/2014 | Nagase et al. | |
| 8,778,958 | B2 | 7/2014 | Cashman | |
| 8,796,301 | B2 | 8/2014 | Ikeda et al. | |
| 8,829,019 | B2 | 9/2014 | Ohta et al. | |
| 9,006,262 | B2 | 4/2015 | Suzuki et al. | |
| 9,725,457 | B2 | 8/2017 | Pasternak et al. | |
| 10,150,775 | B2 | 12/2018 | Pasternak et al. | |
| 11,046,692 | B2 | 6/2021 | Pasternak et al. | |
| 11,760,758 | B2 * | 9/2023 | Kruegel ............... | C07D 491/18 514/278 |
| 2004/0116456 | A1 | 6/2004 | Kumagai et al. | |
| 2008/0234307 | A1 | 9/2008 | Schuetz et al. | |
| 2009/0041687 | A1 | 2/2009 | Beumer et al. | |
| 2009/0221623 | A1 * | 9/2009 | Takayama ............ | C07D 459/00 514/285 |
| 2009/0325857 | A1 | 12/2009 | Beumer et al. | |
| 2010/0120815 | A1 | 5/2010 | Takaki et al. | |
| 2010/0130524 | A1 | 5/2010 | Ikeda et al. | |
| 2010/0190728 | A1 | 7/2010 | Cashman et al. | |
| 2010/0222309 | A1 | 9/2010 | Ona et al. | |
| 2011/0263630 | A1 | 10/2011 | Cashman | |
| 2012/0114752 | A1 | 5/2012 | Ohta et al. | |
| 2012/0302590 | A1 | 11/2012 | Bhide et al. | |
| 2013/0203797 | A1 | 8/2013 | Kobayashi et al. | |
| 2013/0289060 | A1 | 10/2013 | Pasternak et al. | |
| 2013/0289061 | A1 | 10/2013 | Bhide et al. | |
| 2013/0310414 | A1 | 11/2013 | Suzuki et al. | |
| 2014/0255308 | A1 | 9/2014 | Pasternak et al. | |
| 2018/0057504 | A1 | 3/2018 | Pasternak et al. | |
| 2018/0134708 | A1 | 5/2018 | Pasternak et al. | |
| 2022/0135564 | A1 * | 5/2022 | Kruegel .................. | A61P 25/36 514/285 |
| 2023/0250098 | A1 * | 8/2023 | Majumdar ........... | C07D 471/20 514/278 |

FOREIGN PATENT DOCUMENTS

| | | | |
|---|---|---|---|
| JP | 2009507872 | A | 2/2009 |
| WO | WO 2001/068080 | A2 | 9/2001 |
| WO | WO 2005/117589 | A1 | 12/2005 |
| WO | WO 2010/006119 | A1 | 1/2010 |
| WO | WO 2010/083384 | A2 | 7/2010 |

OTHER PUBLICATIONS

Takayama et al., "New Procedure to Mask the 2,3-pi Bond of the Indole Nucleus and Its Application to the Preparation of Potent Opioid Receptor Agonists with a Corynanthe Skeleton", Org. Lett., (2006), 8(25), pp. 5705-5708. (Year: 2006).*

Supplemental information of Takayama et al., "New Procedure to Mask the 2,3-pi Bond of the Indole Nucleus and Its Application to the Preparation of Potent Opioid Receptor Agonists with a Corynanthe Skeleton", Org. Lett., (2006), 8(25), pp. 5705-5708. (Year: 2006).*

Takayama, H., H. Ishikawa, M. Kitajima and N. Aimi, "Formation of an Unusual Dimeric Compound by Lead Tetraacetate Oxidation of a Corynanthe-Type Indole Alkaloid, Mitragynine", Chem. Pharm. Bull. (2002), 50(7), pp. 960-963. (Year: 2002).*

Extended European Search Report for Application No. EP 22190598.7, mailed Aug. 28, 2023.

Supplementary European Search Report for Application No. EP 11835042.0, mailed Mar. 28, 2014.

International Search Report for PCT/US2011/056827 mailed May 17, 2012.

International Preliminary Report on Patentability for Application No. PCT/US2011/056827, mailed Apr. 23, 2013.

Partial Supplementary European Search Report for Application No. EP 16787284.5, mailed Oct. 31, 2018.

Extended European Search Report for Application No. EP 16787284.5, mailed Feb. 4, 2019.

International Search Report for Application No. PCT/US2016/030305, mailed Sep. 1, 2016.

International Preliminary Report on Patentability for Application No. PCT/US2016/030305, mailed, Nov. 9, 2017.

Adkins et al., Mitragyna speciosa, a psychoactive tree from Southeast Asia with opioid activity. Curr Top Med Chem. 2011;11(9):1165-75.

Ananthan, Opioid ligands with mixed mu/delta opioid receptor interactions: an emerging approach to novel analgesics. AAPS J. Mar. 10, 2006;8(1):E118-25. doi: 10.1208/aapsj080114.

Cadet et al., Molecular identification and functional expression of mu 3, a novel alternatively spliced variant of the human mu opiate receptor gene. J Immunol. May 15, 2003;170(10):5118- 23.

Cheng et al., Rhodium-catalyzed intermolecular C—H silylation of arenes with high steric regiocontrol. Science. Feb. 21, 2014;343(6173):853-7. doi:10.1126/science.1248042.

Clark et al., Kappa opiate receptor multiplicity: evidence for two U50,488-sensitive kappa 1 subtypes and a novel kappa 3 subtype. J Pharmacol Exp Ther. Nov. 1989;251(2):461-8.

D'Amour, A Method for Determining Loss of Pain Sensation. J Pharmacol Exp Ther. May 1941;72(1):74-9.

Domling et al., Chemistry and biology of multicomponent reactions. Chem Rev. Jun. 13, 2012;112(6):3083-135. doi: 10.1021/cr100233r. Epub Mar. 22, 2012.

(56) References Cited

OTHER PUBLICATIONS

Domling, Ugi I I. Multicomponent Reactions with Isocyanides. Angew Chem Int Ed Engl. Sep. 15, 2000;39(18):3168-3210.
Dumas et al., Opioid tolerance development: a pharmacokinetic/pharmacodynamic perspective. AAPS J. Dec. 2008;10(4):537-51. doi: 10.1208/s12248-008-9056-1. Epub Nov. 7, 2008.
Eisenberg, TRIMU-5, a mu 2-opioid receptor agonist, stimulates the hypothalamo-pituitary-adrenal axis. Pharmacol Biochem Behav. Apr. 1994;47(4):943-6.
Gengo et al., DPI-3290 [(+)-3-((alpha-R)-alpha-((2S,5R)-4-allyl-2,5-dimethyl-1-piperazinyl)-3-hydroxybenzyl)-N-(3-fluorophenyl)-N-methylbenzamide]. I. A mixed opioid agonist with potent antinociceptive activity. J Pharmacol Exp Ther. Dec. 2003;307(3):1221-6. doi: 10.1124/jpet.103.054361. Epub Oct. 8, 2003.
Gengo et al., DPI-3290 [(+)-3-((alpha-R)-alpha-((2S,5R)-4-Allyl-2,5-dimethyl-1-piperazinyl)-3-hydroxybenzyl)-N-(3-fluorophenyl)-N-methylbenzamide]. II. A mixed opioid agonist with potent antinociceptive activity and limited effects on respiratory function. J Pharmacol Exp Ther. Dec. 2003;307(3):1227-33. doi: 10.1124/jpet.103.054429. Epub Oct. 8, 2003.
Ghirmai et al. Synthesis and Biological Evaluation of .alpha. and .beta.-6-Amido Derivatives of 17-cyclopropylmethyl-3, 14 .beta.-dihydroxy-4 5.alpha.-epoxymorphinan: Potential Alcohol-Cessation. J. Med. Chem., 51, pp. 1913-1924 (2008).
Ghirmai et al. Synthesis and Pharmacological Evaluation of 6-naltrexamine Analogs or Alcohol Sessation. Biorganic and Medicinal Chemistry, vol. 17, pp. 6671-6681 (2009).
Gistrak et al., Pharmacological actions of a novel mixed opiate agonist/antagonist: naloxone benzoylhydrazone. J Pharmacol Exp Ther. Nov. 1989;251(2):469-76.
Gistrak et al., Pharmacological actions of a novel mixed opiate agonist/antagonist: naloxone benzoylhydrazone. J.Pharmacol.Exp. Ther. 1989, 251, 469-476.
Haley et al., Pharmacological effects produced by intracerebral injection of drugs in the conscious mouse. Br. J. Pharmacol. Chemother. 1957, 12, 12-15.
Inturrisi, Clinical pharmacology of opioids for pain. Clin J Pain. Jul.-Aug. 2002;18(4 Suppl):S3-13.
Jansen et al., Ethnopharmacology of kratom and the Mitragyna alkaloids. J Ethnopharmacol. May-Jun. 1988;23(1):115-9.
Jiang et al., Stereochemical studies on medicinal agents. 23. Synthesis and biological evaluation of 6-amino derivatives of naloxone and naltrexone. J Med Chem. Aug. 1977;20(8):1100-2.
Kim et al., A chemical synthesis of 11-methoxy mitragynine pseudoindoxyl featuring the interrupted Ugi reaction. Chem Sci. Sep. 1, 2012;3(9):2849-2852.
Kim et al., A chemical synthesis of 11-methoxy mitragynine pseudoindoxyl featuring the interrupted Ugi reaction. Chem Sci. Sep. 1, 2012;3(9):2849-2852. Supporting Information. 22 pages.
Kim et al., Copper-mediated sequential cyanation of aryl C—B and arene C—H bonds using ammonium iodide and DMF. J Am Chem Soc. Feb. 8, 2012;134(5):2528-31. doi: 10.1021/ja211389g. Epub Jan. 30, 2012.
Kuzmin et al., Kappa-opioid receptor blockade with nor-binaltorphimine modulates cocaine self-administration in drug-naive rats. Eur J Pharmacol. Oct. 9, 1998;358(3):197-202.
Lee et al., A nonpeptidic delta opioid receptor agonist, BW373U86, attenuates the development and expression of morphine abstinence precipitated by naloxone in rat. J Pharmacol Exp Ther. Nov. 1993;267(2):883-7.
Li et al., Design, synthesis, and biological evaluation of 6alpha- and 6beta-N-heterocyclic substituted naltrexamine derivatives as mu opioid receptor selective antagonists. J Med Chem. Mar. 12, 2009;52(5):1416-27. doi: 10.1021/jm801272c. Epub Jun. 4, 2010. 31 pages.
Lowery et al., In vivo characterization of MMP-2200, a mixed ?/? opioid agonist, in mice. J Pharmacol Exp Ther. Mar. 2011;336(3):767-78. doi: 10.1124/jpet.110.172866. Epub Nov. 3, 2010.
Majumdar et al., Generation of novel radiolabeled opiates through site-selective iodination. Bioorg Med Chem Lett. Jul. 1, 2011;21(13):4001-4. doi: 10.1016/j.bmcl.2011.05.008. Epub Jul. 1, 2012. 11 pages.
Majumdar et al., Generation of novel radiolabeled opiates through site-selective iodination. Bioorg.Med.Chem.Lett. 2011, 21, 4001-4004.
Majumdar et al., Synthesis and evaluation of aryl-naloxamide opiate analgesics targeting truncated exon 11-associated mu opioid receptor (MOR-1) splice variants. J.Med.Chem. 2012, 55, 6352-6362.
Majumdar et al., Truncated G protein-coupled mu opioid receptor MOR-1 splice variants are targets for highly potent opioid analgesics lacking side effects. Proc.Natl.Acad.Sci. U.S.A 2011, 108, 19776-19783.
Matsumoto et al., Orally active opioid ?/? dual agonist MGM-16, a derivative of the indole alkaloid mitragynine, exhibits potent antiallodynic effect on neuropathic pain in mice. J Pharmacol Exp Ther. Mar. 2014;348(3):383-92. doi: 10.1124/jpet.113.208108. Epub Dec. 17, 2013. Erratum in: J Pharmacol Exp Ther. Apr. 2019;369(1):142.
Nitsche et al., Thiazolidinone-peptide hybrids as dengue virus protease inhibitors with antiviral activity in cell culture. J Med Chem. Nov. 14, 2013;56(21):8389-403. oi:10.1021/jm400828u. Epub Oct. 22, 2013.
O'Neill et al., Antagonistic modulation between the delta opioid agonist BW373U86 and the mu opioid agonist fentanyl in mice. J Pharmacol Exp Ther. Jul. 1997;282(1):271-7.
Pan et al., Identification and characterization of six new alternatively spliced variants of the human mu opioid receptor gene, Oprm. Neuroscience. 2005;133(1):209-20.
Pan, Identification and characterization of a novel promoter of the mouse mu opioid receptor gene (Oprm) that generates eight splice variants. Gene. Jul. 24, 2002;295(1):97-108.
Pasternak et al., Antisense mapping KOR-1: evidence for multiple kappa analgesic mechanisms. Brain Research 1999, 826, 289-292.
Paul et al., Differential blockade by naloxonazine of two m opiate actions: analgesia and inhibition of gastrointestinal transit. Eur.J. Pharmacol. 1988, 149, 403-404.
Paul et al., Differential blockade by naloxonazine of two mu opiate actions: analgesia and inhibition of gastrointestinal transit. Eur J Pharmacol. May 10, 1988;149(3):403-4.
Phillipson et al: Alkaloids of Uncaria attenuata, U. orientalis and U. Canescens. Phytochemistry, Pergamon Press, GB, vol. 14, No. 8, 1975, pp. 1855-1863.
Pickett et al., Pd-catalyzed stannylation of radioiodination targets. Bioorganic & Medicinal Chemistry Letters 2015, 25, 1761-1764.
Podolsky et al., Novel fentanyl-based dual ?/?-opioid agonists for the treatment of acute and chronic pain. Life Sci. Dec. 18, 2013;93(25-26):1010-6. doi: 10.1016/j.lfs.2013.09.016. Epub Sep. 29, 2013.
Ponglux et al., A New Indole Alkaloid, 7 alpha-Hydroxy-7H-mitragynine, from Mitragyna speciosa in Thailand. Planta Med 1994, 60, 580-1.
Riviere et al., Opioid receptors. Targets for new gastrointestinal drug development. Drug Development, Molecular Targets for GI Diseases . 2000. Totowa, NJ: Humana Press; 203-238.Eds.: Gaginella et al.
Rossi et al., Antisense mapping DOR-1 in mice: further support for delta receptor subtypes. Brain Res. 1997, 753, 176-179.
Rossi et al., Differential blockade of morphine and morphine-6b-glucuronide analgesia by antisense oligodeoxynucleotides directed against MOR-1 and G-protein a subunits in rats. Neurosci.Lett. 1995, 198, 99-102.
Rossi et al., Novel receptor mechanisms for heroin and morphine-6b-glucuronide analgesia. Neurosci.Lett. 1996, 216, 1-4.
Rothman et al., Interaction of endogenous opioid peptides and other drugs with four kappa opioid binding sites in guinea pig brain. Peptides. Mar.-Apr. 1990;11(2):311-31.
Su et al., Delta-opioid ligands reverse alfentanil-induced respiratory depression but not antinociception. J Pharmacol Exp Ther. Dec. 1998;287(3):815-23.
Takayama et al., Studies on the synthesis and opioid agonistic activities of mitragynine-related indole alkaloids: discovery of opioid agonists structurally different from other opioid ligands. Journal of Medicinal Chemistry 2002, 45, 1949-56.

(56) References Cited

OTHER PUBLICATIONS

Takayama et al., The first total synthesis of (?)-mitragynine, an analgesic indole alkaloid in mitragyna speciosa. Tetrahedron Letters v36(51), Dec. 18, 1995:9337-9340.
Takayama, Chemistry and pharmacology of analgesic indole alkaloids from the rubiaceous plant, Mitragyna speciosa. Chem Pharm Bull (Tokyo). Aug. 2004;52(8):916-28.
Varadi et al., Novel 6beta-acylaminomorphinans with analgesic activity. Eur.I.Med.Chem 2013, 69C, 786-789.
Varadi et al., Synthesis and Characterization of a Dual Kappa-Delta Opioid Receptor Agonist Analgesic Blocking Cocaine Reward Behavior. ACS Chemical Neuroscience 2015, 6, 1813-1824.
Varadi et al., Synthesis of Carfentanil Amide Opioids Using the Ugi Multicomponent Reaction. ACS Chem Neurosci 2015,6, 1570-1577.
Váradi et al., Mitragynine/Corynantheidine Pseudoindoxyls As Opioid Analgesics with Mu Agonism and Delta Antagonism, Which Do Not Recruit β-Arrestin-2. J Med Chem. 2016;59(18):8381-8397. doi:10.1021/acs.jmedchem.6b00748.
Watanabe et al., Inhibitory effect of mitragynine, an alkaloid with analgesic effect from Thai medicinal plant Mitragyna speciosa, on electrically stimulated contraction of isolated guinea-pig ileum through the opioid receptor. Life Sci. 1997;60(12):933-42.
Xu et al., Characterizing exons 11 and 1 promoters of the mu opioid receptor (Oprm) gene in transgenic mice. BMC Mol Biol. Nov. 13, 2006;7:41.
Xu et al., Identification and characterization of seven new exon 11-associated splice variants of the rat ? opioid receptor gene, OPRM1. Mol Pain. Jan. 21, 2011;7:9. doi:10.1186/1744-8069-7-9.
Xu et al., Stabilization of the ?-opioid receptor by truncated single transmembrane splice variants through a chaperone-like action. J Biol Chem. Jul. 19, 2013;288(29):21211-27. doi: 10.1074/jbc.M113.458687. Epub Jun. 11, 2013.
Yamamoto et al., Opioid receptor agonistic characteristics of mitragynine pseudoindoxyl in comparison with mitragynine derived from Thai medicinal plant Mitragyna speciosa. Gen Pharmacol. Jul. 1999;33(1):73-81.
Zarembo et al., Metabolites of mitragynine. J Pharm Sci. Sep. 1974;63(9):1407-15.
Zhang et al., Specific cross-linking of Lys233 and Cys235 in the mu opioid receptor by a reporter affinity label. Biochemistry. Feb. 22, 2005;44(7):2271-5.
Zou et al., Highly efficient aerobic oxidative hydroxylation of arylboronic acids: photoredox catalysis using visible light. Angew Chem Int Ed Engl. Jan. 16, 2012;51(3):784-8. doi: 10.1002/anie.201107028. Epub Dec. 7, 2011.
Partial Supplementary European Search Report for Application No. EP 22190598.7, mailed May 23, 2023.
Takayama et al., New procedure to mask the 2,3-pi bond of the indole nucleus and its application to the preparation of potent opioid receptor agonists with a Corynanthe skeleton. Org Lett. Dec. 7, 2006;8(25):5705-8. doi: 10.1021/01062173k.
Herlem et al., [Photochemical oxidation of tertiary amines and alkaloids XI: Sensitized photooxidation of corynantheidine. Transformation of corynantheine-like derivatives into sarpagine-like derivatives]. Tetrahedron. 1982;38(2):271-278.

* cited by examiner

A: Derived from papaverine morphine (1) buprenorphine pentazocine fentanyl

B: Salvinorin analogs salvinorin A (2) herkinorin

C: Mitragynine analogs mitragynine (3) 7-hydroxymitragynine (4) mitragynine pseudoindoxyl (5)

corynantheidine (6) 9-hydroxycorynantheidine (7)

Table 1. Receptor binding and [$^{35}$S]GTPγS functional assays in transfected cell lines.

| | Affinity ($K_i$ nM)[a] | | | [$^{35}$S]GTPγS functional assays[b] | | | | | | | |
|---|---|---|---|---|---|---|---|---|---|---|---|
| Compound | Mu | Kappa | Delta | Mu | | Kappa | | | Delta | | |
| | | | | $EC_{50}$ (nM) | $E_{max}$ (%) | $EC_{50}$ (nM) | $E_{max}$ (%) | $IC_{50}$ (nM) | $EC_{50}$ (nM) | $E_{max}$ (%) | $IC_{50}$ (nM) |
| **morphine** | 2 | 49 | 278 | | | | | | | | |
| 3 | 230 | 231 | 1011 | 185 | 63 | – | antagonist | 4613 | – | antagonist | >10uM |
| 3 (racemic) | 420 | 510 | 2084 | | | | | | | | |
| 4 | 33 | 105 | 91 | 55 | 64 | – | antagonist | 2134 | – | antagonist | 998 |
| 4 (racemic) | 62 | 208 | 180 | | | | | | | | |
| 5 | 2.3 | 58 | 14 | 0.6 | 74 | – | antagonist | 32 | – | antagonist | 0.8 |
| 7 | 182 | 973 | 451 | 451 | 58 | – | – | – | – | – | – |
| 8 | 38 | 69 | 20.46 | 10.89 | 112 | – | antagonist | 620 | – | antagonist | 139 |
| 17 | 102 | 40 | >1000 | 129 | 90 | 49 | 104 | – | – | – | – |
| 18 | 24 | 194 | 640 | 18 | 90 | 298 | 79.5 | – | 546 | 47 | – |
| 19 | 180 | 35 | 898 | >1uM | ~10% | 136.9 | 109 | | >1uM | ~10% | |

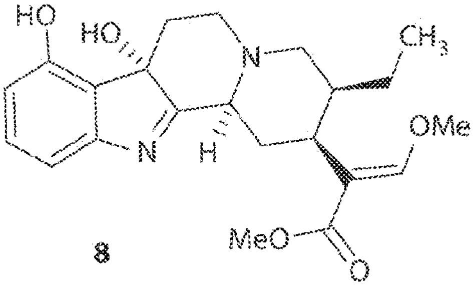

8

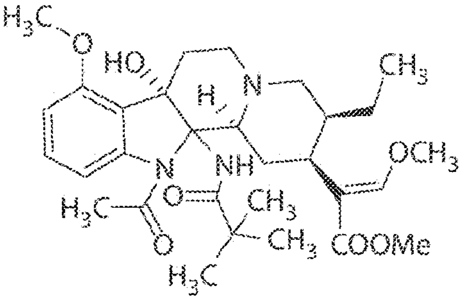

19: R = *t*-butyl

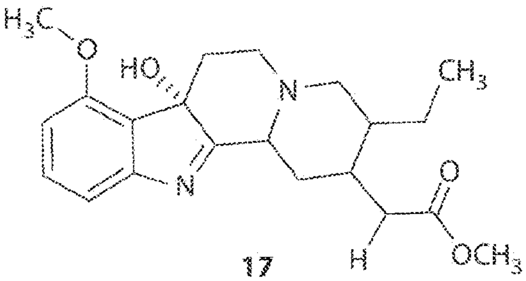

17

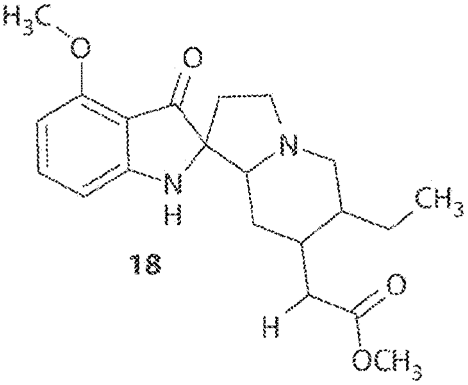

Table 2: Mouse strain sensititivities of morphine and mitragynine alkaloids

| | Tail Flick Analgesia $ED_{50}$(icv, µg) | | | | | |
|---|---|---|---|---|---|---|
| **Drug** | **CD1** | **C57** | **129** | **Swiss Webster** | **BALB-C** | **CXBK** |
| Morphine | 0.6 | 4.1 | 0.03 | 3.3 | 0.21 | >10 |
| **3**[a] | 50 | >300 | | | | |
| **4** | 0.11 | 10 | 0.032 | >10 µg[b] | 0.46 | 18.7 |
| **5** | 0.6 | 1.2 | 0.31 | 1.3 | 0.16 | |
| **8** | 0.2 | | | | | |

9

10 a) 0.1-10 mol% $[Ir(COD)Cl]_2$, 0.1-10 mol% chiral phoshpine ligands (binaphthalenes, benzodioxoles, biphenyls, phosphinooxazolines)
0-10 mol% $I_2$, 50-600 psi $H_2$, RT-100 °C, various solvents b) $HB(C_6F_5)$, various alkenes, 50-600 psi $H_2$, RT-100 °C, various solvents

14 + 16 → 9

0.1-10 mol% KI, 50-120 °C, 2h-24h reaction time, various solvents (DMF, benzene, acetonitrile)

Figure 6A

Table 3. *In Vivo* Pharmacology Evaluation of Intracerebroventricular Administration

| **Compound** | **Analgesia, *icv* ($ED_{50}$, ug)** | | | |
|---|---|---|---|---|
| | **CD1** | **C57** | **129S6/SvEv** | **E11 KO** |
| 7-hydroxymitragynine | 0.11 | | 0.032 | 1.05 (33x) |
| Morphine | 0.6 | | | |
| Mitragynine pseudoindoxyl | 0.6 | 1.15 | | 6.15 (5x) |

Figure 6B

Table 4. *In Vivo* Pharmacology Evaluation of Subcutaneous Administration

| **Compound** | **Analgesia, *sc* ($ED_{50}$, mg/kg)** |
|---|---|
| | **CD1 mice** |
| 7-hydroxymitragynine | 1.25 |
| Mitragynine pseudoindoxyl | 3-5 |
| Morphine | 5 |

*In vitro* pharmacology of the compounds
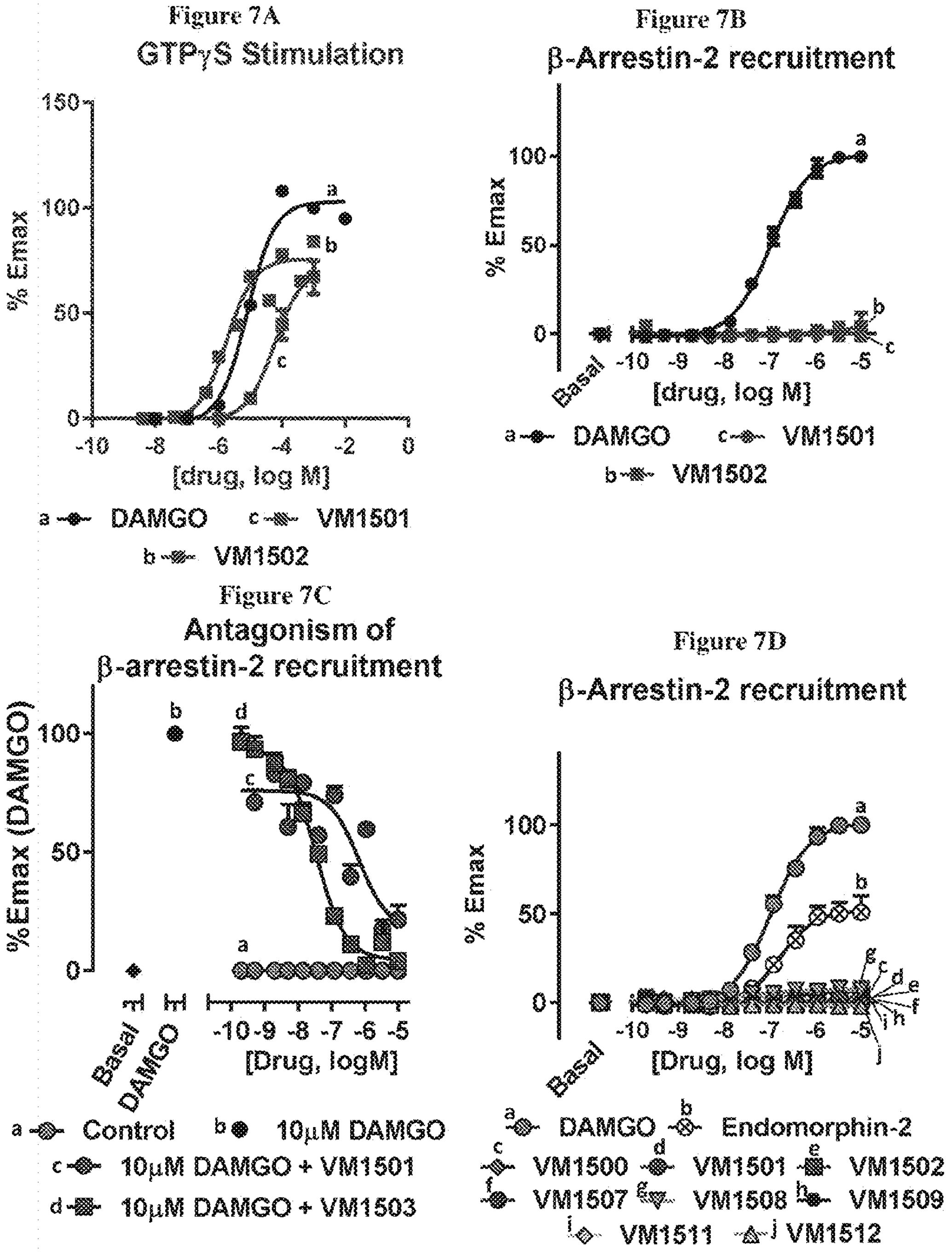

*In vivo* pharmacology of VM1501

Antinociception of VM1502 upon intracerebroventricular, subcutaneous, and oral administration.

Figure 10. Antinociception of VM1502 in rats upon subcutaneous administration.
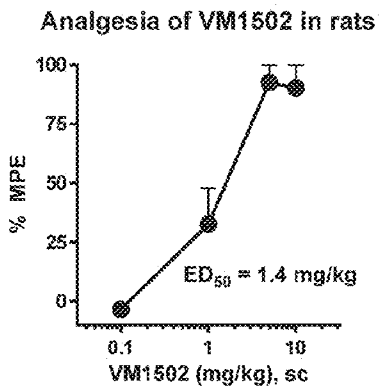

Pharmacological and genetic reversal of antinociception of VM1502.

Side effect studies with VM1502.

Development of tolerance to VM1502 and morphine.

Figure 14. Comparison of respiratory depression of VM1502 and VM1512.
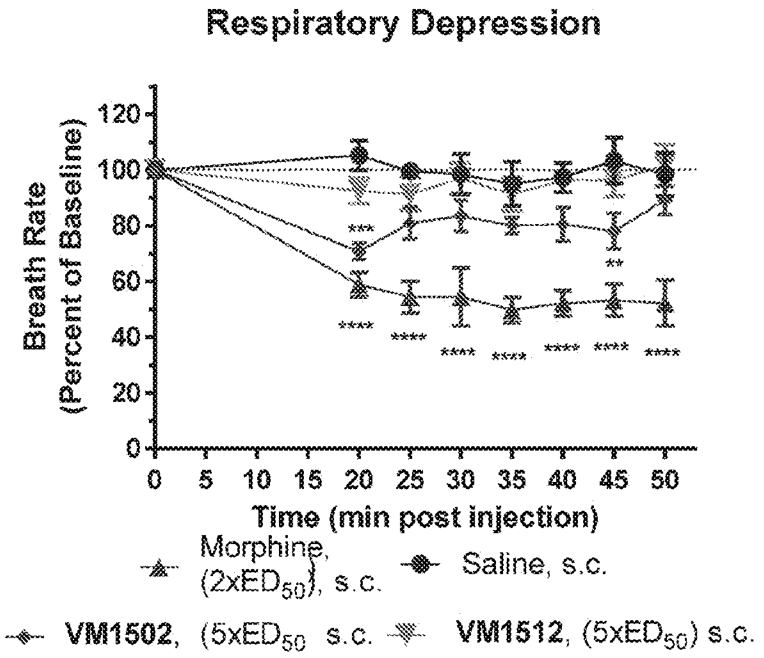

MITRAGYNINE ANALOGS AND USES THEREOF

RELATED APPLICATIONS

This application is a division of U.S. patent application Ser. No. 15/570,308, filed Oct. 27, 2017, which is a national stage filing under 35 U.S.C. § 371 of International PCT Application, PCT/US2016/030305, filed on Apr. 29, 2016, which claims priority under 35 U.S.C. § 119(e) to U.S. Provisional Application, U.S. Ser. No. 62/155,248, filed Apr. 30, 2015, each of which is incorporated herein by reference.

REFERENCE TO A SEQUENCE LISTING SUBMITTED AS A TEXT FILE VIA EFS-WEB

The application contains a Sequence Listing which has been submitted in ASCII format via EFS-Web and is hereby incorporated by reference in its entirety. Said ASCII copy, created on Oct. 13, 2021, is named S171570017US02-SEQ-WWZ and is 1,367 bytes in size.

BACKGROUND OF THE INVENTION

Opioid receptors are a group of G protein-coupled receptors with opioids as ligands. The opioid receptors are categorized into three subsets, μ (MOR), δ (DOR) and κ (KOR) receptors. Opioid receptors are found throughout the central and peripheral nervous system of many mammalian species, including humans. Modulation of the respective receptors can elicit numerous, albeit different, biological effects (Riviere et al., *Drug Development,* 2000, 203-238). A couple of biological effects identified for opioid modulators have led to many useful medicinal agents. Most significant are the many centrally acting MOR agonistic modulators, marketed as analgesic agents, to attenuate pain (e.g., morphine), as well as peripherally acting MOR agonists to regulate motility (e.g., loperamide).

Mitragynine, an indole alkaloid, is the most abundant active alkaloid in the plant *Mitragyna speciosa*, commonly known as Kratom (Jansen, *J. Ethnopharmacol.,* 1988, 23 (1), 115-119). The pharmacological activities of mitragynine and related alkaloids have been found to have agonistic effects on opioid receptors (Watanabe et al., *Life Sci.,* 1997, 60, 933-942; Takayama et al., *J. Med. Chem.,* 2002, 45, 1949-1956). Studies have been carried out on the opioid agonistic effects of the constituents of *Mitragyna speciosa* using in vitro assays. 7-Hydroxymitragynine and mitragynine pseudoindoxyl have been found to be more active as opioid agonists than mitragynine, and 7-Hydroxymitragynine and mitragynine pseudoindoxyl are more potent than morphine (Takayama et al., *Chem. Pharm. Bull.* 52 (8): 916-928 (2004); see also Kim et al., *Chem Sci.,* 2012, 3(9): 2849-2852).

Opioid modulators produce a diverse spectrum of centrally- and peripherally-mediated side effects, including respiratory depression, nausea, sedation, euphoria or dysphoria, decreased gastrointestinal motility, and itching (Inturrisi, *Clin. J. Pain,* 2002, 18(4 Suppl): S3-S13.). Long-term use of opioids can also be problematic due to the rapid development of profound tolerance to the analgesic effects coupled with slow development of untoward side effects. It is the inability to tolerate these undesirable side effects that eventually limits dose escalations and analgesic efficacy (Dumas et al., *AAPS J.,* 2008, 10(4): 537-551). Therefore, there is a need to develop new therapeutic agents for pain treatment with improved pharmacological profiles.

SUMMARY OF THE INVENTION

Mitragynine and 7-hydroxymitragynine, and mitragynine pseudoindoxyl (FIG. 1) are indole alkaloids isolated from the plant *Mitragyna* speciose (Takayama et al., *Chem. Pharm. Bull.* 52 (8): 916-928 (2004); see also Kim et al., *Chem Sci.,* 2012, 3(9): 2849-2852). Mitragynine pseudoindoxyl has been reported to be a microbial transformation product of mitragynine. (Zarembo et. al., Journal of Pharmaceutical Sciences 1974, 63, 1407-15). Oxidation of the indole nucleus of mitragynine produces 7-hydroxymitragynine, which can undergo a base/acid-induced rearrangement to the isomeric metabolite mitragynine pseudoindoxyl. 7-Hydroxymitragynine and mitragynine pseudoindoxyl are more active as opioid agonists than the parent indole mitragynine, and 7-hydroxymitragynine and mitragynine pseudoindoxyl are more potent than the well-known opioid morphine. These indole alkaloids present a class of useful therapeutics for pain treatment and modulating activities of opioid receptors with reduced side effects compared to the prior alkaloid analgesics, such as morphine and morphine derivatives.

The present invention provides compounds of Formulae (I')-(II'), pharmaceutical compositions thereof, and kits including the compounds and compositions described herein useful in pain management/treatment or modulating the activities of opioid receptors. The present invention provides compounds of Formulae (I)-(II), pharmaceutical compositions thereof, and kits including the compounds and compositions described herein useful in pain management/treatment or modulating the activities of opioid receptors. The present invention further provides methods of using the inventive compounds, and pharmaceutically acceptable salts, solvates, hydrates, polymorphs, co-crystals, tautomers, stereoisomers, isotopically labeled derivatives, and prodrugs thereof, and compositions thereof, to treat or manage pain and/or modulate the activities of opioid receptors (e.g., MOR).

In one aspect, the present invention provides compounds of Formula (I'):

(I')

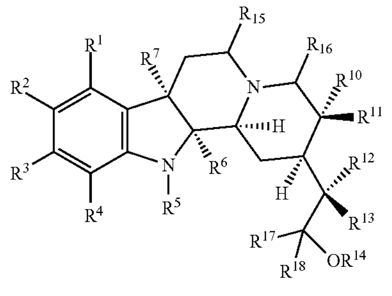

and pharmaceutically acceptable salts, solvates, hydrates, polymorphs, co-crystals, tautomers, stereoisomers, isotopically labeled derivatives, and prodrugs thereof.

In one aspect, the present invention provides compounds of Formula (I):

(I)

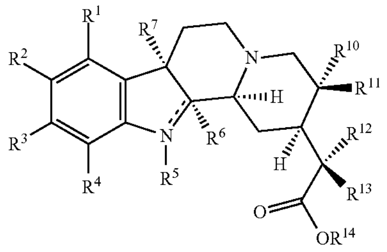

and pharmaceutically acceptable salts, solvates, hydrates, polymorphs, co-crystals, tautomers, stereoisomers, isotopically labeled derivatives, and prodrugs thereof.

In another aspect, the present invention provides compounds of Formula (II'):

(II')

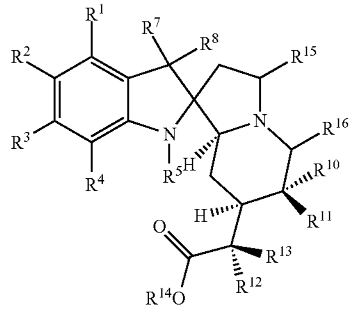

and pharmaceutically acceptable salts, solvates, hydrates, polymorphs, co-crystals, tautomers, stereoisomers, isotopically labeled derivatives, and prodrugs thereof.

In another aspect, the present invention provides compounds of Formula (II):

(II)

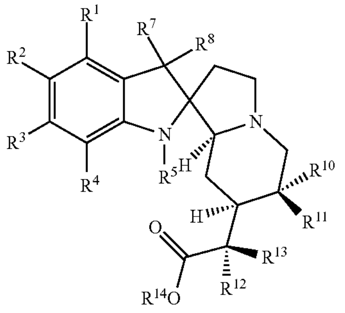

and pharmaceutically acceptable salts, solvates, hydrates, polymorphs, co-crystals, tautomers, stereoisomers, isotopically labeled derivatives, and prodrugs thereof.

In another aspect, the present invention provides methods of synthesizing a compound of any one of Formulae (I')-(II'), or a pharmaceutically acceptable salt, solvate, hydrate, polymorph, co-crystal, tautomer, stereoisomer, isotopically labeled derivative, or prodrug thereof. In another aspect, the present invention provides methods of synthesizing a compound of any one of Formulae (I)-(II), or a pharmaceutically acceptable salt, solvate, hydrate, polymorph, co-crystal, tautomer, stereoisomer, isotopically labeled derivative, or prodrug thereof.

In another aspect, the present invention provides pharmaceutical compositions comprising a compound of any one of Formulae (I')-(II'), or a pharmaceutically acceptable salt, solvate, hydrate, polymorph, co-crystal, tautomer, stereoisomer, isotopically labeled derivative, or prodrug thereof, and optionally a pharmaceutically acceptable carrier. In another aspect, the present invention provides pharmaceutical compositions comprising a compound of any one of Formulae (I)-(II), or a pharmaceutically acceptable salt, solvate, hydrate, polymorph, co-crystal, tautomer, stereoisomer, isotopically labeled derivative, or prodrug thereof, and optionally a pharmaceutically acceptable carrier. In certain embodiments, the pharmaceutical compositions described herein include a therapeutically effective amount of a compound of Formula (I')-(II'), or a pharmaceutically acceptable salt thereof. In certain embodiments, the pharmaceutical compositions described herein include a therapeutically effective amount of a compound of Formula (I)-(II), or a pharmaceutically acceptable salt thereof. In certain embodiments, the provided pharmaceutical compositions comprise a second therapeutic agent. In certain embodiments, the compounds and pharmaceutical compositions described herein are useful for pain treatment or pain management. In certain embodiments, the compounds and pharmaceutical compositions described herein are useful for inducing an analgesic effect in a subject. In certain embodiments, the compounds and pharmaceutical compositions described herein are useful for treating a neurological or psychiatric disease (e.g., addiction or depression) in a subject. In certain embodiments, the compounds and pharmaceutical compositions described herein are useful for modulating activities of one or more opioid receptors in a subject. In certain embodiments, the compounds and pharmaceutical compositions described herein are useful for modulating activities of one or more opioid receptors in a biological sample. In certain embodiments, the compounds and pharmaceutical compositions described herein have an agonistic effect on an opioid receptor. In certain embodiments, the compounds and pharmaceutical compositions described herein have an antagonistic effect on an opioid receptor. In certain embodiments, the opioid receptor is a μ opioid receptor (MOR). In certain embodiments, the MOR is 6TM/E11. In certain embodiments, the opioid receptor is a δ opioid receptor (DOR). In certain embodiments, the opioid receptor is a κ opioid receptor (KOR). In certain embodiments, the compounds and pharmaceutical compositions described herein have dual activities, having an agonistic effect on an opioid receptor (e.g. MOR) and an antagonistic effect on another opioid receptor (e.g. KOR).

In another aspect, the present invention provides methods of treating or managing pain comprising administering to a subject in need thereof a therapeutically effective amount of a compound, or a pharmaceutical composition thereof, as described herein.

In another aspect, the present invention provides methods of inducing an analgesic effect comprising administering to the subject in need thereof a therapeutically effective amount of a compound, or a pharmaceutical composition thereof, as described herein.

In another aspect, the present invention provides methods of treating a neurological disease comprising administering to the subject in need thereof a therapeutically effective amount of a compound, or a pharmaceutical composition thereof, as described herein.

In another aspect, the present invention provides methods of treating a psychiatric disease comprising administering to the subject in need thereof a therapeutically effective amount of a compound, or a pharmaceutical composition thereof, as described herein.

In another aspect, the present invention provides methods of treating an inflammatory disease comprising administering to the subject in need thereof a therapeutically effective amount of a compound, or a pharmaceutical composition thereof, as described herein.

In another aspect, the present invention provides methods of modulating an opioid receptor activity in a subject comprising administering to the subject in need thereof a therapeutically effective amount of a compound, or a pharmaceutical composition thereof, as described herein.

In another aspect, the present invention provides methods of modulating an opioid receptor activity in a biological sample comprising contacting the biological sample with a therapeutically effective amount of a compound, or a composition thereof, as described herein.

In another aspect, the present invention provides kits comprising a compound of any one of Formulae (I')-(II'), or a pharmaceutically acceptable salt, solvate, hydrate, polymorph, co-crystal, tautomer, stereoisomer, isotopically labeled derivative, or prodrug thereof, or a pharmaceutical composition thereof. In another aspect, the present invention provides kits comprising a compound of any one of Formulae (I)-(II), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of any one of Formulae (I')-(II'), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of any one of Formulae (I)-(II), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for pain treatment or pain management. The provided kits may be useful for inducing an analgesic effect in a subject. The provided kits may be useful for treating a neurological or psychiatric disease in a subject. The provided kits may be useful for treating an inflammatory disease in a subject. The provided kits may also be useful for modulating the activities of one or more opioid receptor in a subject or biological sample. In certain embodiments, the kits described herein further include instructions for administering a compound of any one of Formulae (I')-(II'), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits described herein further include instructions for administering a compound of any one of Formulae (I)-(VI), or a pharmaceutically acceptable salt, solvate, hydrate, polymorph, co-crystal, tautomer, stereoisomer, isotopically labeled derivative, or prodrug thereof, or a pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

The details of certain embodiments of the invention are set forth herein. Other features, objects, and advantages of the invention will be apparent from the Detailed Description, the Figures, the Examples, and the Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-4}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), 10ydroxy[2.2.1]heptanyl ($C_7$), 10ydroxy[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused to one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl, and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Arylalkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 $\pi$ electrons shared in a cyclic array) having ring carbon atoms and 1-4 ring heteroatoms provided in the aromatic ring system, wherein each heteroatom is independently selected from nitrogen, oxygen, and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$—, —$SSR^{cc}$, —C(=O)$R^{aa}$, —$CO_2H$, —CHO, —$C(OR^{cc})_2$, —$CO_2R^{aa}$, —OC(=O)$R^{aa}$, —$OCO_2R^{aa}$, —C(=O)$N(R^{bb})_2$, —OC(=O)$N(R^{bb})_2$, —$NR^{bb}$C(=O)$R^{aa}$, —$NR^{bb}CO_2R^{aa}$, —$NR^{bb}$C(=O)$N(R^{bb})_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)$N(R^{bb})_2$, —OC(=$NR^{bb}$)$N(R^{bb})_2$, —$NR^{bb}$C(=$NR^{bb}$)$N(R^{bb})_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —$Si(R^{aa})_3$, —$OSi(R^{aa})_3$—C(=S)$N(R^{bb})_2$, —C(=O)$SR^{aa}$, —C(=S)$SR^{aa}$, —SC(=S)$SR^{aa}$, —SC(=O)$SR^{aa}$—OC(=O)$SR^{aa}$, —SC(=O)$OR^{aa}$, —SC(=O)$R^{aa}$, —P(=O)$(R^{aa})_2$, —P(=O)$(OR^{cc})_2$, —OP(=O)$(R^{aa})_2$, —OP(=O)$(OR^{aa})_2$, —P(=O)$(N(R^{bb})_2)_2$, —OP(=O)$(N(R^{bb})_2)_2$, —$NR^{bb}$P(=O)$(R^{aa})_2$, —$NR^{bb}$P(=O)$(OR^{cc})_2$, —$NR^{bb}$P(=O)$(N(R^{bb})_2)$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C(=O)R^{aa}$, $—C(=O)N(R^{cc})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, $—NO_2$, $—N_3$, $—SO_2H$, $—SO_3H$, —OH, —OR, $—ON(R^{ff})_2$, $—N(R^{ff})_2$, $—N(R^{ff})_3^+X^-$, $—N(OR^{ee})R^{ff}$, —SH, $—SR^{ee}$, $—SSR^{ee}$, $—C(=O)R^{ee}$, $—CO_2H$, $—CO_2R^{ee}$, $—OC(=O)R^{ee}$, $—OCO_2R^{ee}$, $—C(=O)N(R^{ff})_2$, $—OC(=O)N(R^{ff})_2$, $—NR^{ff}C(=O)R^{ee}$, $—NR^{ff}CO_2R^{ee}$, $—NR^{ff}C(=O)N(R^{ff})_2$, $—C(=NR^{ff})OR^{ee}$, $—OC(=NR^{ff})R^{ee}$, $—OC(=NR^{ff})OR^{ee}$, $—C(=NR^{ff})N(R^{ff})_2$, $—OC(=NR^{ff})N(R^{ff})_2$, $—NR^{ff}C(=NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(=O)R^{ee}$, $—Si(R^{ee})_3$, $—OSi(R^{ee})_3$, $—C(=S)N(R^{ff})_2$, $—C(=O)SR^{ee}$, $—C(=S)SR^{ee}$, $—SC(=S)SR^{ee}$, $—P(=O)(OR^{ee})_2$, $—P(=O)(R^{ee})_2$, $—OP(=O)(R^{ee})_2$, $—OP(=O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, $—NO_2$, $—N_3$, $—SO_2H$, $—SO_3H$, —OH, $—OC_{1-6}$ alkyl, $—ON(C_{1-6}\ alkyl)_2$, $—N(C_{1-6}\ alkyl)_2$, $—N(C_{1-6}\ alkyl)_3^+X^-$, $—NH(C_{1-6}\ alkyl)_2^+X^-$, $—NH_2(C_{1-6}\ alkyl)^+X^-$, $—NH_3^+X^-$, $—N(OC_{1-6}\ alkyl)(C_{1-6}\ alkyl)$, $—N(OH)(C_{1-6}\ alkyl)$, —NH(OH), —SH, $—SC_{1-6}$ alkyl, $—SS(C_{1-6}\ alkyl)$, $—C(=O)(C_{1-6}\ alkyl)$, $—CO_2H$, $—CO_2(C_{1-6}\ alkyl)$, $—OC(=O)(C_{1-6}\ alkyl)$, $—OCO_2(C_{1-6}\ alkyl)$, $—C(=O)NH_2$, $—C(=O)N(C_{1-6}\ alkyl)_2$, $—OC(=O)NH(C_{1-6}\ alkyl)$, $—NHC(=O)(C_{1-6}\ alkyl)$, $—N(C_{1-6}\ alkyl)C(=O)(C_{1-6}\ alkyl)$, $—NHCO_2(C_{1-6}\ alkyl)$, $—NHC(=O)N(C_{1-6}\ alkyl)_2$, $—NHC(=O)NH(C_{1-6}\ alkyl)$, $—NHC(=O)NH_2$, $—C(=NH)O(C_{1-6}\ alkyl)$, $—OC(=NH)(C_{1-6}\ alkyl)$, $—OC(=NH)OC_{1-6}$ alkyl, $—C(=NH)N(C_{1-6}\ alkyl)_2$, $—C(=NH)NH(C_{1-6}\ alkyl)$, $—C(=NH)NH_2$, $—OC(=NH)N(C_{1-6}\ alkyl)_2$, $—OC(NH)NH(C_{1-6}\ alkyl)$, $—OC(NH)NH_2$, $—NHC(NH)N(C_{1-6}\ alkyl)_2$, $—NHC(=NH)NH_2$, $—NHSO_2(C_{1-6}\ alkyl)$, $—SO_2N(C_{1-6}\ alkyl)_2$, $—SO_2NH(C_{1-6}\ alkyl)$, $—SO_2NH_2$, $—SO_2C_{1-6}$ alkyl, $—SO_2OC_{1-6}$ alkyl, $—OSO_2C_{1-6}$ alkyl, $—SOC_{1-6}$ alkyl, $—Si(C_{1-6}\ alkyl)_3$, $—OSi(C_{1-6}\ alkyl)_3$-$C(=S)N(C_{1-6}\ alkyl)_2$, $C(=S)NH(C_{1-6}\ alkyl)$, $C(=S)NH_2$, $—C(=O)S(C_{1-6}\ alkyl)$, $—C(=S)SC_{1-6}$ alkyl, $—SC(=S)SC_{1-6}$ alkyl, $—P(=O)(OC_{1-6}\ alkyl)_2$, $—P(=O)(C_{1-6}\ alkyl)_2$, $—OP(=O)(C_{1-6}\ alkyl)_2$, $—OP(=O)(OC_{1-6}\ alkyl)_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^9$ substituents can be joined to form =O or =S; wherein $X^-$ is a counterion.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of $—C(=O)R^{aa}$, —CHO, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—C(=O)NR^{bb}SO_2R^{aa}$, $—C(=S)N(R^{bb})_2$, $—C(=O)SR^{aa}$, and $—C(=S)SR^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —C(═O)$R^{aa}$, —C(═O)N$(R^{cc})_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)N$(R^{cc})_2$, —$SO_2N(R^{cc})_2$, —$SO_2R^{cc}$, —$SO_2OR^{cc}$, —$SOR^{aa}$, —C(═S)N$(R^{cc})_2$, —C(═O)$SR^{cc}$, —C(═S)$SR^{cc}$, —P(═O)$_2R^{aa}$, —P(═O)$(R^{aa})_2$, —P(═O)$_2N(R^{cc})_2$, —P(═O)$(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —$N(R^{cc})_2$, —C(═O)$R^{aa}$, —C(═O)N$(R^{cc})_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)N$(R^{cc})_2$, —$SO_2N(R^{cc})_2$, —$SO_2R^{cc}$, —$SO_2OR^{cc}$, —$SOR^{aa}$, —C(═S)N$(R^{cc})_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(═O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(═O)$SR^{aa}$, —C(═O)$R^{aa}$, —$CO_2R^{aa}$, —C(═O)$N(R^{bb})_2$, —C(═$NR^{bb}$)$R^{aa}$, —C(═$NR^{bb}$)$OR^{aa}$, —C(═$NR^{bb}$)$N(R^{bb})_2$, —S(═O)$R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —P(═O)$(R^{aa})_2$, —P(═O)$(OR^{cc})_2$, and —P(═O)$(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(═O)$SR^{aa}$, —C(═O)$R^{aa}$, —$CO_2R^{aa}$, —C(═O)$N(R^{bb})_2$, —C(═$NR^{bb}$)$R^{aa}$, —C(═$NR^{bb}$)$OR^{aa}$, —C(═$NR^{bb}$)$N(R^{bb})_2$, —S(═O)$R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —P(═O)$(R^{aa})_2$, —P(═O)$(OR^{cc})_2$, and —P(═O)$(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulae (I)-(II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R\cdot x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R\cdot 0.5\ H_2O$)), and polyhydrates (x is a number greater than 1, e.g., dihydrates ($R\cdot 2\ H_2O$) and hexahydrates ($R\cdot 6\ H_2O$)).

As used herein, the term "tautomer" includes two or more interconvertible forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formulae (I')-(II'), which have cleavable groups and become by solvolysis or under physiological conditions the compounds of Formula (I')-(II') which are pharmaceutically active in vivo. The term "prodrugs" refer to compounds, including derivatives of the compounds of Formulae (I)-(II), which have cleavable groups and become by solvolysis or under physiological conditions the compounds of Formula (I)-(II) which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I)-(II) may be preferred in certain instances.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

The terms "administer," "administering," or "administration," as used herein, refers to implanting, absorbing, ingesting, injecting, inhaling, or otherwise introducing an inventive compound, or a pharmaceutical composition thereof, into a subject or biological sample.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formulae (I')-(II') refers to an amount sufficient to elicit a desired biological response, i.e., treating the condition. An "effective amount" of a compound of Formulae (I)-(II) refers to an amount sufficient to elicit a desired biological response, i.e., treating the condition. As will be appreciated by those of ordinary skill in this art, the effective amount of a compound of Formulae (I')-(II') may vary depending on such factors as the desired biological endpoint, the pharmacokinetics of the compound, the condition being treated, the mode of administration, and the age and health of the subject. As will be appreciated by those of ordinary skill in this art, the effective amount of a compound of Formulae (I)-(II) may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound of Formulae (I')-(II') is an amount sufficient to provide a therapeutic benefit in the treatment of a condition or to delay or minimize one or more symptoms associated with the condition. A "therapeutically effective amount" of a compound of Formulae (I)-(II) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formulae (I')-(II') is an amount sufficient to prevent a condition, or one or more symptoms associated with the condition or prevent its recurrence. A "prophylactically effective amount" of a compound of Formulae (I)-(II) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein "inhibition," "inhibiting," and "inhibit", refer to the ability of a compound to reduce, slow, halt or prevent activity of a particular biological process in a cell relative to vehicle. In certain embodiments, the biological process is in vitro (e.g., cellular assay). In certain embodiments, the biological process is in vivo.

As used herein, the term "effective amount" refers to the amount of a compound or composition that elicits the relevant response in vitro or in vivo. For example, in the case of a provided compound of the present invention used in an assay of the present invention, an effective amount of a provided compound is an amount that elicits the desired response, e.g., binding to a desired opioid receptor, activating a desired opioid receptor, or inhibiting a desired opioid receptor.

The term "independently" is used herein to indicate that the groups can be identical or different.

The terms "labeled", "labeled with a detectable agent", and "labeled with a detectable moiety" are used herein interchangeably. "Label" and "detectable moiety" are also used interchangeably herein. When used in reference to a probe compound, these terms specify that the probe compound can be detected or visualized. In certain embodiments, a label is selected such that it generates a signal which can be measured and whose intensity is related to the amount of probe compound bound to a protein (e.g., in a sample). A label may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Labels suitable for use in the present invention may be detectable by any of a variety of means including, but not limited to, spectroscopic, photochemical, biochemical, immunochemical, electrical, optical or chemical means. Suitable labels include, but are not limited to, various ligands, radionuclides, fluorescent dyes, chemiluminescent agents, microparticles, enzymes, calorimetric labels, magnetic labels, and haptens.

BRIEF DESCRIPTION OF THE DRAWINGS

FIG. 2 shows the evaluation of exemplary opioids in the receptor binding assays and [$^{35}$S]GTPγS functional assays in transfected cell lines (Table 1). The exemplary compounds from the present invention and the known opioids were subject to radioligand receptor binding assays and [$^{35}$S]-GTPγS functional assays in opioid transfected cell lines (Table 1). β-arrestin-2 recruitment using the MOR-1 DiscoveRx assay (4 and 5 only) and in vivo tail flick analgesia assays in mice, with the compound given supraspinally (icv). [a]Competition studies were performed with the indicated compounds against $^{125}$I-IBNtxA (0.1 nM) in membranes from CHO cells stably expressing the indicated cloned mouse opioid receptors. Ki values were calculated from the $IC_{50}$ values as previously described. [b]Efficacy data were obtained using agonist induced stimulation of [$^{35}$S] GTPγS binding assay. Efficacy is represented as EC50 (nM) and percent maximal stimulation (Emax) relative to standard agonist DAMGO peptide (MOR), DPDPE peptide (DOR), or U50,488H (KOR) at 100 nM. To determine the antagonist properties of a compound, membranes were incubated with 100 nM of the appropriate agonist in the presence of varying concentrations of the compound.

FIG. 3 shows the mouse strain sensitivities of morphine and mitragynine alkaloids (Table 2). ED50 values were determined supraspinally in groups of mice using a cumulative dosing paradigm. [a]Studies were difficult due to its low potency and poor solubility. [b]No analgesia at 10 μg. Higher doses resulted in seizures.

FIGS. 6A and 6B show the in vivo evaluation of morphine, 7-hydroxymitragynine, and mitragynine pseudoindoxyl.

FIGS. 7A-7D show the in vitro pharmacological evaluation of selected compounds. FIG. 7A shows [$^{35}$S]GTPγS stimulation for selected compounds. FIG. 7B and FIG. 7D show β-arrestin-2 recruitment for selected compounds. FIG. 7C shows evaluation of the antagonism of β-arrestin-2 recruitment in selected compounds.

FIG. 8A shows dose-response curves of antinociception of VM1501. FIG. 8B shows the analgesic response for selected compounds. FIG. 8C shows evaluation of the respiratory rate of animals for selected compounds. FIG. 8D shows evaluation of gastrointestinal transit with selected compounds. In FIG. 8E, reversal of antinociception by selective antagonists was evaluated. All values are expressed as the mean t SEM.

FIG. 9A shows dose-response curves of antinociception of VM1502 and morphine given supraspinally in CD1 mice. FIG. 9B shows dose-response curves of antinociception of VM1502 given subcutaneously in CD1 mice. FIG. 9C shows the time course of tail flick antinociception of VM1502 given orally in CD1 male mice. [a]The means of each point in each determination were determined as percentage maximal possible effect (% MPE) [(observed latency−baseline latency)/(maximal latency−baseline latency)]×100. Points represent mean±SEM.

FIG. 10 shows antinociception of compound VM1502 in rats upon subcutaneous administration. In FIG. 10, groups of rats (n=3) were assessed for subcutaneously given VM1502 analgesia at 15 mins in a cumulative dose-response paradigm where animals received escalating doses of VM1502 to generate the analgesic dose-response curve. The $ED_{50}$ was 1.4 mg/kg.

FIG. 11A depicts reversal of antinociception by selective antagonists. FIG. 11B shows analgesic response of VM1502 and antisense downregulation. *Significantly different from control ($p<0.05$). FIG. 11C depicts dose-response curves of antinociception of VM1502 and given subcutaneously in C57/BL6 (wild type and E1/E11 double MOR-1 knockout).

FIG. 12A shows evaluation of tolerance for the selected compound. *Significantly different from morphine ($p<0.05$). The experiment was replicated at least twice with similar results. FIG. 12B shows evaluation of physical dependence for the selected compound. *Significantly different from saline. (One-way ANOVA followed by Dunnett's multiple comparison test, $p<0.05$). FIG. 12C shows evaluation of gastrointestinal transit for the selected compound. FIG. 12D shows evaluation of respiratory rate. FIG. 12E shows evaluation of conditioned place-preference and aversion for the selected compound. Mean difference in time spent on the drug-paired side t SEM is presented (n=17-21). *Significantly different from matching preconditioning preference ($p<0.05$); + significantly different from cocaine, morphine, and U50,488 preference (two-way repeated measures ANOVA with Sidak's post hoc test).

FIGS. 13A-13B depict the shifts in the analgesic $ED_{50}$'s of VM1502 in groups of mice dosed chronically with VM1502 for 5,12, 22 and 29 days . . . FIG. 13C depicts the shifts in the analgesic $ED_{50}$'s of morphine in groups of mice dosed chronically e with morphine for 5 days.

FIG. 14 shows the comparison of respiratory depression for animals dosed with compounds VM1502 and VM1512.

DETAILED DESCRIPTION OF CERTAIN EMBODIMENTS

Figure 1A:
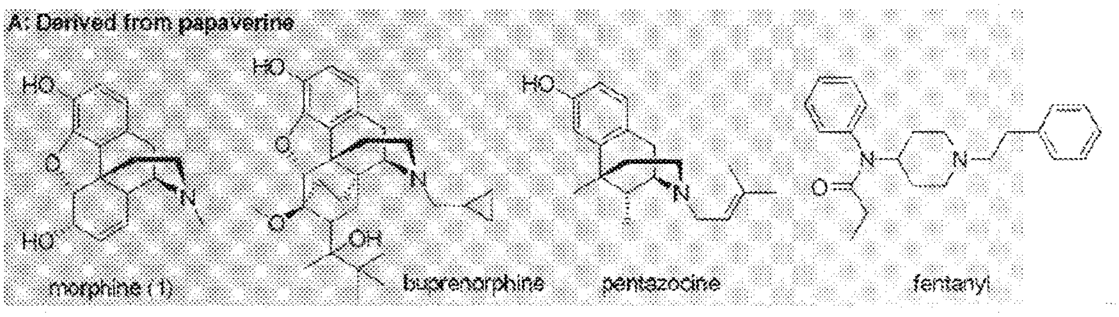
FIG. 1A shows exemplary opioids based on the morphine scaffold.
Figure 1B:
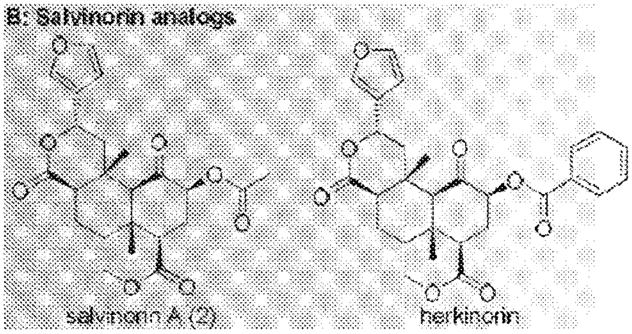
FIG. 1B shows exemplary opioids based on the salvinorin scaffold.
Figure 1C:
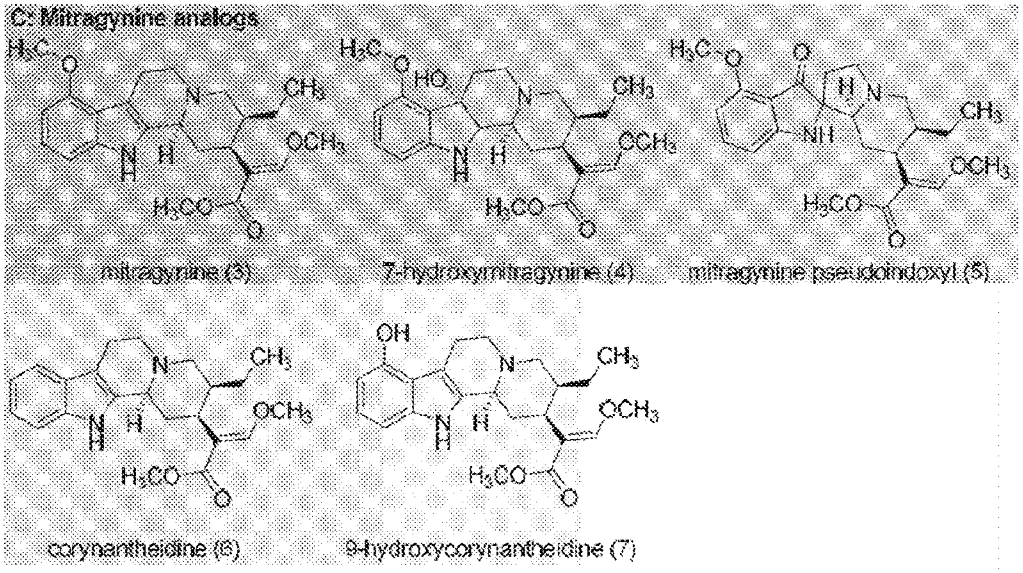
FIG. 1C shows exemplary opioids based on the mitragynine scaffold.

The opioids are commonly used to treat acute and severe pain. Long-term opioid administration eventually reaches a dose ceiling that is attributable to the rapid onset of analgesic tolerance coupled with the slow development of side effects such as respiratory depression, nausea, and decreased gastrointestinal motility. Mitragynine analogs are useful for modulating opioid receptor activities. 7-Hydroxymitragynine and mitragynine pseudoindoxyl are more active as opioid agonists than the parent indole mitragynine. 7-hydroxymitragynine and mitragynine pseudoindoxyl are more potent than the well-known opioid morphine. The compounds present an appealing scaffold to develop opioid receptor ligands for pain treatment/management and/or modulating activities of opioid receptors with improved pharmacological profiles.

The present invention provides compounds of Formulae (I')-(II'), and pharmaceutically acceptable salts thereof, solvates, hydrates, polymorphs, co-crystals, tautomers, stereoisomers, isotopically labeled derivatives, and prodrugs thereof. These compounds have been found to bind to and modulate the activities of opioid receptors. The present invention provides compounds of Formulae (I)-(II), and pharmaceutically acceptable salts thereof, solvates, hydrates, polymorphs, co-crystals, tautomers, stereoisomers, isotopically labeled derivatives, and prodrugs thereof. These compounds have been found to bind to and modulate the activities of opioid receptors. Also provided are methods of using these opioid receptor modulators, such as compounds of Formulae (I')-(II'), or pharmaceutically acceptable salts, solvates, hydrates, polymorphs, co-crystals, tautomers, stereoisomers, isotopically labeled derivatives, or prodrugs thereof, to treat a painful condition or manage pain in a subject. Also provided are methods of using these opioid receptor modulators, such as compounds of Formulae (I)-(II), or pharmaceutically acceptable salts, solvates, hydrates, polymorphs, co-crystals, tautomers, stereoisomers, isotopically labeled derivatives, or prodrugs thereof, to treat a painful condition or manage pain in a subject. Further provided are methods of using these opioid receptor modulators, such as compounds of Formulae (I')-(II'), or pharmaceutically acceptable salts, solvates, hydrates, polymorphs, co-crystals, tautomers, stereoisomers, isotopically labeled derivatives, or prodrugs thereof, to treat a neurological or psychiatric disease in a subject. Further provided are methods of using these opioid receptor modulators, such as compounds of Formulae (I)-(II), or pharmaceutically acceptable salts, solvates, hydrates, polymorphs, co-crystals, tautomers, stereoisomers, isotopically labeled derivatives, or prodrugs thereof, to treat a neurological or psychiatric disease in a subject. Also provided are methods of using these opioid receptor modulators, such as compounds of Formulae (I')-(II'), or pharmaceutically acceptable salts, solvates, hydrates, polymorphs, co-crystals, tautomers, stereoisomers, isotopically labeled derivatives, or prodrugs thereof, to treat an inflammatory disease in a subject. Also provided are methods of using these opioid receptor modulators, such as compounds of Formulae (I')-(II'), or pharmaceutically acceptable salts, solvates, hydrates, polymorphs, co-crystals, tautomers, stereoisomers, isotopically labeled derivatives, or prodrugs thereof, to treat an inflammatory disease in a subject. Also provided are methods of using these opioid receptor modulators, such as compounds of Formulae (I)-(II), or pharmaceutically acceptable salts, solvates, hydrates, polymorphs, co-crystals, tautomers, stereoisomers, isotopically labeled derivatives, or prodrugs thereof, to treat an inflammatory disease in a subject. The present invention further provides methods of using compounds of Formulae (I')-(II'), or pharmaceutically acceptable salts, solvates, hydrates, polymorphs, co-crystals, tautomers, stereoisomers, isotopically labeled derivatives, or prodrugs thereof as therapeutics, e.g., in modulating the activities of one or more opioid receptors. The present invention further provides methods of using compounds of Formulae (I)-(II), or pharmaceutically acceptable salts, solvates, hydrates, polymorphs, co-crystals, tautomers, stereoisomers, isotopically labeled derivatives, or prodrugs thereof as therapeutics, e.g., in modulating the activities of one or more opioid receptors. In certain embodiments, the provided compounds have an agonistic effect on one or more opioid receptors. In certain embodiments, the provided compounds have an antagonistic effect on one or more opioid receptors. In certain embodiments, the provided compounds have dual activities, an agonistic effect on one opioid receptor, and an antagonistic effect on another opioid receptor. In certain embodiments, the provided compounds have an agonistic effect on MOR, and an antagonistic effect on DOR and KOR. In certain embodiments, the provided compounds and compounds not recruiting β-arrestin-2 have an agonistic effect on MOR, and an antagonistic effect on DOR and KOR. The provided compounds and pharmaceutical compositions have improved pharmacological profiles with minimized side effects compared to the traditional analgesics, such as morphine.

Compounds

As generally described above, provided herein are compounds of Formula (I'):

(I')

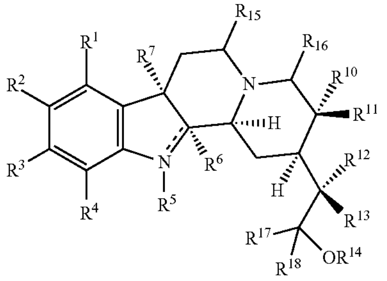

or a pharmaceutically acceptable salt, solvate, hydrate, polymorph, co-crystal, tautomer, stereoisomer, isotopically labeled derivative, or a prodrug thereof, wherein:

- ---- is a single bond or double bond;
- each of $R^1$, $R^2$, $R^3$, and $R^4$ is independently selected from the group consisting of hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$;
- $R^5$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(═O)$R^C$, —C(═O)$OR^A$, —C(═O)$N(R^B)_2$, S(═O)$R^C$, —$SO_2R^C$, —$SO_2N(R^B)_2$, or a nitrogen protecting group;
- $R^6$ is hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —C(═O)$R^C$, —C(═O)$OR^A$, —C(═O)$N(R^B)_2$, —OC(═O)$R^C$, —OC(═O)N$(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, or —$SO_2N(R^B)_2$;
- or $R^5$ and $R^6$ are absent and ---- is a double bond;
- $R^7$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —OC(═O)$R^C$, —C(═O)$R^C$, —C(═O)$OR^A$, —OC(═O)$N(R^B)_2$, —C(═O)$N(R^B)_2$, S(═O)$R^C$, —$SO_2R^C$, —$SO_2N(R^B)_2$, or an oxygen protecting group;
- each of $R^{10}$, $R^{11}$, $R^{12}$, and $R^{13}$ is independently selected from the group consisting of hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, and —$SR^A$;
- or $R^{12}$ and $R^{13}$ are taken together to form an optionally substituted alkenyl moiety;

- $R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;
- each of $R^{15}$ and $R^{16}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N_3$, —$OR^A$, —$N(R^B)_2$, and —$SR^A$;
- each of $R^{17}$ and $R^{18}$ is independently selected from the group consisting of hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, and —$SR^A$; or $R^{17}$ and $R^{18}$ are taken together to form

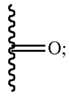

- each instance of $R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, or a sulfur protecting group when attached to sulfur, or a selenium protecting group when attached to selenium;
- each instance of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group, or two $R^B$ groups are taken together with their intervening atoms to form an optionally substituted heterocyclic ring; and
- each instance of $R^C$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

As generally described above, provided herein are compounds of Formula (I):

(I)

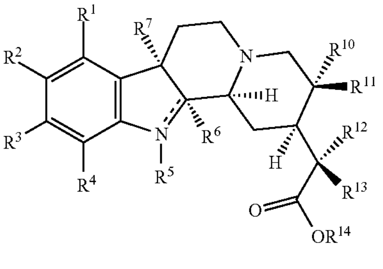

or a pharmaceutically acceptable salt, solvate, hydrate, polymorph, co-crystal, tautomer, stereoisomer, isotopically labeled derivative, or a prodrug thereof, wherein:

- ---- is a single bond or double bond;
- each of $R^1$, $R^2$, $R^3$, and $R^4$ is independently selected from the group consisting of hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$;
- $R^5$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(═O)$R^C$, —C(═O)$OR^A$, —C(═O)$N(R^B)_2$, S(═O)$R^C$, —$SO_2R^C$, —$SO_2N(R^B)_2$, or a nitrogen protecting group;
- $R^6$ is hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, or —$SO_2N(R^B)_2$;
- or $R^5$ and $R^6$ are absent and ---- is a double bond;
- $R^7$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —OC(═O)$R^C$, —C(═O)$R^C$, —C(═O)$OR^A$, —OC(═O)$N(R^B)_2$, —C(═O)$N(R^B)_2$, S(═O)$R^C$, —$SO_2R^C$, —$SO_2N(R^B)_2$, or an oxygen protecting group;
- each of $R^{10}$, $R^{11}$, $R^{12}$, and $R^{13}$ is independently selected from the group consisting of hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, and —$SR^A$;
- or $R^{12}$ and $R^{13}$ taken together with the intervening carbon atom to form optionally substituted alkenyl;
- $R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;
- each instance of $R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a selenium protecting group when attached to selenium;
- each instance of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group, or two $R^B$ groups are taken together with their intervening atoms to form an optionally substituted heterocyclic ring; and
- each instance of $R^C$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and
- provided that when $R^{12}$ and $R^{13}$ are taken together with the intervening carbon atom to form an optionally substituted alkenyl moiety, then $R^2$ is hydrogen, and at least one of $R^1$, $R^3$, and $R^4$ is substituted; and
- provided that when $R^{12}$ and $R^{13}$ are taken together with the intervening carbon atom to form an optionally substituted alkenyl moiety, and $R^2$, $R^3$, and $R^4$ are hydrogen, then $R^1$ is selected from the group consisting of halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$.

Further provided herein is a compound of Formula (II'):

(II')

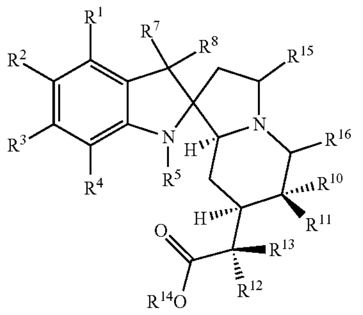

or a pharmaceutically acceptable salt thereof, wherein:

- each of $R^1$, $R^2$, $R^3$, and $R^4$ is independently selected from the group consisting of hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$;

$R^5$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(═O)$R^C$, —C(═O)$OR^A$, —C(═O)$N(R^B)_2$, S(═O)$R^C$, —$SO_2R^C$, —$SO_2N(R^B)_2$, or a nitrogen protecting group;

$R^7$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —OC(═O)$R^C$, —C(═O)$R^C$, —C(═O)$OR^A$, —OC(═O)$N(R^B)_2$, —C(═O)$N(R^B)_2$, S(═O)$R^C$, —$SO_2R^C$, —$SO_2N(R^B)_2$, or an oxygen protecting group;

$R^8$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

or $R^7$ and $R^8$ are taken together to form C═O.

each of $R^{10}$, $R^{11}$, $R^{12}$, and $R^{13}$ is independently selected from the group consisting of hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, and —$SR^A$;

or $R^{12}$ and $R^{13}$ taken together to form an optionally substituted alkenyl moiety;

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of $R^5$ and $R^{16}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N_3$, —$OR^A$, —$N(R^B)_2$, and —$SR^A$;

each instance of $R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a selenium protecting group when attached to selenium;

each instance of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group, or two $R^B$ groups are taken together with their intervening atoms to form an optionally substituted heterocyclic ring; and each instance of $R^C$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl.

Further provided herein is a compound of Formula (II):

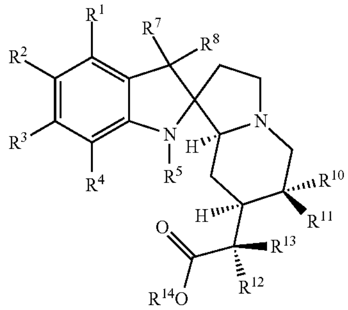

(II)

or a pharmaceutically acceptable salt, solvate, hydrate, polymorph, co-crystal, tautomer, stereoisomer, isotopically labeled derivative, or prodrug thereof, wherein:

each of $R^1$, $R^2$, $R^3$, and $R^4$ is independently selected from the group consisting of hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$;

$R^5$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(═O)$R^C$, —C(═O)$OR^A$, —C(═O)$N(R^B)_2$, S(═O)$R^C$, —$SO_2R^C$, —$SO_2N(R^B)_2$, or a nitrogen protecting group;

$R^7$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —OC(═O)$R^C$, —C(═O)$R^C$, —C(═O)$OR^A$, —OC(═O)$N(R^B)_2$, —C(═O)$N(R^B)_2$, S(═O)$R^C$, —$SO_2R^C$, —$SO_2N(R^B)_2$, or an oxygen protecting group;

$R^8$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

or $R^7$ and $R^8$ taken with the intervening atoms to form C═O;

each of $R^{10}$, $R^{11}$, $R^{12}$, and $R^{13}$ is independently hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, or —$SR^A$;

or $R^{12}$ and $R^{13}$ taken together with the intervening carbon atom to form optionally substituted alkenyl;

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a selenium protecting group when attached to selenium;

each instance of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group, or two $R^B$ groups are taken together with their intervening atoms to form an optionally substituted heterocyclic ring; and each instance of $R^C$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and provided that when $R^{12}$ and $R^{13}$ are taken together with the intervening carbon atom to form an optionally substituted alkenyl moiety, then $R^2$ is hydrogen, and at least one of $R^1$, $R^3$, and $R^4$ is substituted; and provided that when $R^{12}$ and $R^{13}$ are taken together with the intervening carbon atom to form optionally a substituted alkenyl moiety, and $R^2$ and $R^4$ are hydrogen, then $R^1$ is selected from the group consisting of halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$.

As generally defined herein, $R^1$ is hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$. In some embodiments, $R^1$ is hydrogen. In some embodiments, $R^1$ is halogen. In certain embodiments, $R^1$ is F. In certain embodiments, $R^1$ is Cl. In certain embodiments, $R^1$ is Br. In certain embodiments, $R^1$ is I. In certain embodiments, $R^1$ is optionally substituted $C_{1-6}$ alkyl. In certain embodiments, $R^1$ is unsubstituted $C_{1-6}$ alkyl. In certain embodiments, $R^1$ is methyl or ethyl. In certain embodiments, $R^1$ is substituted $C_{1-6}$ alkyl. In certain embodiments, $R^1$ is optionally substituted $C_{1-6}$ haloalkyl. In certain embodiments, $R^1$ is $CH_2F$, $CHF_2$, or $CF_3$. In certain embodiments, $R^1$ is optionally substituted alkenyl$C_{1-6}$alkyl. In certain embodiments, $R^1$ is optionally substituted $C_{2-6}$ alkenyl. In certain embodiments, $R^1$ is allyl. In certain embodiments, $R^1$ is vinyl. In certain embodiments, $R^1$ is optionally substituted carbocyclyl. In certain embodiments, $R^1$ is optionally substituted cyclopropyl. In certain embodiments, $R^1$ is optionally substituted aryl. In certain embodiments, $R^1$ is optionally substituted phenyl. In certain embodiments, $R^1$ is Ph. In some embodiments, $R^1$ is optionally substituted heteroaryl. In some embodiments, $R^1$ is optionally substituted five-membered heteroaryl. In some embodiments, $R^1$ is unsubstituted five-membered heteroaryl. In some embodiments, $R^1$ is substituted five-membered heteroaryl. In some embodiments, $R^1$ is optionally substituted thiophenyl. In some embodiments, $R^1$ is unsubstituted thiophenyl. In some embodiments, $R^1$ is thiophen-2-yl. In some embodiments, $R^1$ is thiophen-3-yl. In some embodiments, $R^1$ is substituted thiophenyl. In some embodiments, $R^1$ is optionally substituted furanyl. In some embodiments, $R^1$ is unsubstituted furanyl. In some embodiments, $R^1$ is furan-2-yl. In some embodiments, $R^1$ is furan-3-yl. In some embodiments, $R^1$ is substituted furanyl. In some embodiments, $R^1$ is optionally substituted pyrrolyl. In some embodiments, $R^1$ is unsubstituted pyrrolyl. In some embodiments, $R^1$ is 1H-pyrrol-2-yl. In some embodiments, $R^1$ is 1H-pyrrol-3-yl. In some embodiments, $R^1$ is substituted pyrrolyl. In certain embodiments, $R^1$ is —$OR^A$, wherein $R^A$ is as generally defined herein. In certain embodiments, $R^1$ is —$OR^A$ and $R^A$ is hydrogen or optionally substituted alkyl. In certain embodiments, $R^1$ is —OH. In certain embodiments, $R^1$ is —$OR^A$ and $R^A$ is optionally substituted $C_{1-6}$ alkyl. In certain embodiments, $R^1$ is —$OR^A$ and $R^A$ is unsubstituted $C_{1-6}$ alkyl. In certain embodiments, $R^1$ is —$OCH_3$. In certain embodiments, $R^1$ is —O(acyl) (e.g., —OAc). In certain embodiments, $R^1$ is —$OR^A$ and $R^A$ is substituted $C_{1-6}$ alkyl. In certain embodiments, $R^1$ is —$OR^A$ and $R^A$ is $C_{1-6}$ haloalkyl. In certain embodiments, $R^1$ is —$OR^A$ and $R^A$ is $CH_2F$, $CHF_2$, or $CF_3$. In certain embodiments, $R^1$ is —$N(R^B)_2$, wherein each instance of $R^B$ is as generally defined herein. In certain embodiments, $R^1$ is —$NHR^B$, wherein $R^B$ is as generally defined herein. In certain embodiments, $R^1$ is —$NHR^B$, wherein $R^B$ is optionally substituted acyl. In certain embodiments, $R^1$ is —$NHR^B$, wherein $R^B$ is acetyl. In certain embodiments, $R^1$ is —CN.

As generally defined herein, $R^2$ is hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$. In some embodiments, $R^2$ is hydrogen. In some embodiments, $R^2$ is halogen. In certain embodiments, $R^2$ is F. In certain embodiments, $R^2$ is Cl. In certain embodiments, $R^2$ is Br. In certain embodiments, $R^2$ is I. In certain embodiments, $R^2$ is optionally substituted $C_{1-6}$ alkyl. In certain embodiments, $R^2$ is unsubstituted $C_{1-6}$ alkyl. In certain embodiments, $R^2$ is methyl or ethyl. In certain embodiments, $R^2$ is optionally substituted aryl. In certain embodiments, $R^2$ is phenyl. In certain embodiments, $R^2$ is optionally substituted heteroaryl. In some embodiments, $R^2$ is unsubstituted five-membered heteroaryl. In some embodiments, $R^2$ is substituted five-membered heteroaryl. In some embodiments, $R^2$ is optionally substituted thiophenyl. In some embodiments, $R^2$ is unsubstituted thiophenyl. In some embodiments, $R^2$ is thiophen-2-yl. In some embodiments, $R^1$ is thiophen-3-yl. In some embodiments, $R^2$ is substituted thiophenyl. In some embodiments, $R^2$ is optionally substituted furanyl. In some embodiments, $R^2$ is unsubstituted furanyl. In some embodiments, $R^2$ is furan-2-yl. In some embodiments, $R^2$ is furan-3-yl. In some embodiments, $R^2$ is substituted furanyl.

As generally defined herein, $R^3$ is hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, and —$SO_2N(R^B)_2$. In some embodiments, $R^3$ is hydrogen. In some embodiments, $R^3$ is halogen. In certain embodiments, $R^3$ is F. In certain embodiments, $R^3$ is Cl. In certain embodiments, $R^3$ is Br. In certain embodiments, $R^3$ is I. In certain embodiments, $R^3$ is optionally substituted $C_{1-6}$ alkyl. In certain embodiments, $R^3$ is unsubstituted $C_{1-6}$ alkyl. In certain embodiments, $R^3$ is methyl or ethyl. In certain embodiments, $R^3$ is substituted $C_{1-6}$ alkyl. In certain embodiments, $R^3$ is optionally substituted $C_{1-6}$ haloalkyl. In certain embodiments, $R^3$ is —$CH_2F$, —$CHF_2$, or —$CF_3$. In certain embodiments, $R^3$ is optionally substituted carbocyclyl. In certain embodiments, $R^3$ is optionally substituted cyclopropyl. In certain embodiments, $R^3$ is optionally substituted aryl. In certain embodiments, $R^3$ is optionally substituted phenyl. In certain embodiments, $R^3$ is Ph. In certain embodiments, $R^3$ is optionally substituted heteroaryl. In certain embodiments, $R^3$ is optionally substituted furanyl, optionally substituted thiophenyl, or optionally substituted pyrrolyl. In certain embodiments, $R^3$ is —$OR^A$, wherein $R^A$ is as generally defined herein. In certain embodiments, $R^3$ is —$OR^A$, and $R^A$ is hydrogen or optionally substituted alkyl. In certain embodiments, $R^3$ is —OH. In certain embodiments, $R^3$ is —$OR^A$, and $R^A$ is optionally substituted $C_{1-6}$ alkyl. In certain embodiments, $R^3$ is —$OR^A$, and $R^A$ is unsubstituted $C_{1-6}$ alkyl. In certain embodiments, $R^3$ is —$OCH_3$. In certain embodiments, $R^3$ is —$OR^A$, and $R^A$ is substituted $C_{1-6}$ alkyl. In certain embodiments, $R^3$ is —$OR^A$ and $R^A$ is $C_{1-6}$ haloalkyl. In certain embodiments, $R^3$ is —$OR^A$, and $R^A$ is $CH_2F$, $CHF_2$, or $CF_3$. In certain embodiments, $R^3$ is —$N(R^B)_2$, wherein each instance of $R^B$ is as generally defined herein. In certain embodiments, $R^3$ is —$NHR^B$, wherein $R^B$ is as generally defined herein. In certain embodiments, $R^3$ is —$NHR^B$, wherein $R^B$ is optionally substituted acyl. In certain embodiments, $R^3$ is —$NHR^B$, wherein $R^B$ is acetyl.

As generally defined herein, $R^4$ is hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, S(═O)$R^C$, —$SO_2R^C$, —$NR^BSO_2R^C$, or —$SO_2N(R^B)_2$. In some embodiments, $R^4$ is hydrogen. In some embodiments, $R^4$ is halogen. In certain embodiments, $R^4$ is F. In certain embodiments, $R^4$ is Cl. In certain embodiments, $R^4$ is Br. In certain embodiments, $R^4$ is I. In certain embodiments, $R^4$ is optionally substituted $C_{1-6}$ alkyl. In certain embodiments, $R^4$ is unsubstituted $C_{1-6}$ alkyl. In certain embodiments, $R^4$ is methyl or ethyl. In certain embodiments, $R^4$ is substituted $C_{1-6}$ alkyl. In certain embodiments, $R^4$ is optionally substituted $C_{1-6}$ haloalkyl. In certain embodiments, $R^4$ is $CH_2F$, $CHF_2$, or $CF_3$. In certain embodiments, $R^4$ is optionally substituted carbocyclyl. In certain embodiments, $R^4$ is optionally substituted cyclopropyl. In certain embodiments, $R^4$ is optionally substituted aryl. In certain embodiments, $R^4$ is optionally substituted phenyl. In certain embodiments, $R^4$ is Ph. In certain embodiments, $R^4$ is optionally substituted heteroaryl. In certain embodiments, $R^4$ is optionally substituted furanyl, optionally substituted thiophenyl, or optionally substituted pyrrolyl. In certain embodiments, $R^4$ is optionally substituted heteroaryl. In some embodiments, $R^4$ is unsubstituted five-membered heteroaryl. In some embodiments, $R^4$ is substituted five-membered heteroaryl. In some embodiments, $R^4$ is optionally substituted thiophenyl. In some embodiments, $R^4$ is unsubstituted thiophenyl. In some embodiments, $R^4$ is thiophen-2-yl. In some embodiments, $R^4$ is thiophen-3-yl. In some embodiments, $R^4$ is substituted thiophenyl. In some embodiments, $R^4$ is optionally substituted furanyl. In some embodiments, $R^4$ is unsubstituted furanyl. In some embodiments, $R^4$ is furan-2-yl. In some embodiments, $R^4$ is furan-3-yl. In some embodiments, $R^4$ is substituted furanyl.

In certain embodiments, $R^4$ is —$OR^A$, wherein $R^A$ is as generally defined herein. In certain embodiments, $R^4$ is —$OR^A$, and $R^A$ is hydrogen or optionally substituted alkyl. In certain embodiments, $R^4$ is —OH. In certain embodiments, $R^4$ is —$OR^A$, and $R^A$ is optionally substituted $C_{1-6}$ alkyl. In certain embodiments, $R^4$ is —$OR^A$, and $R^A$ is unsubstituted $C_{1-6}$ alkyl. In certain embodiments, $R^4$ is —$OCH_3$. In certain embodiments, $R^4$ is —$OR^A$, and $R^A$ is substituted $C_{1-6}$ alkyl. In certain embodiments, $R^4$ is —$OR^A$, and $R^A$ is $C_{1-6}$ haloalkyl. In certain embodiments, $R^4$ is —$OR^A$, and $R^A$ is —$CH_2F$, —$CHF_2$, or —$CF_3$. In certain embodiments, $R^4$ is —$N(R^B)_2$, wherein each instance of $R^B$ is as generally defined herein. In certain embodiments, $R^4$ is —$NHR^B$, wherein $R^B$ is as generally defined herein. In certain embodiments, $R^4$ is —$NHR^B$, wherein $R^B$ is optionally substituted acyl. In certain embodiments, $R^4$ is —$NHR^B$, wherein $R^B$ is acetyl.

As generally defined herein, $R^5$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(═O)$R^C$, —C(═O)$OR^A$, —C(═O)$N(R^B)_2$, S(═O)$R^C$, —$SO_2R^C$, —$SO_2N(R^B)_2$, or a nitrogen protecting group. In certain embodiments, $R^5$ is hydrogen, optionally substituted $C_{1-6}$ alkyl, or a nitrogen protecting group. In some embodiments, $R^5$ is hydrogen. In some embodiments, $R^5$ is optionally substituted $C_{1-6}$ alkyl. In certain embodiments, $R^5$ is methyl. In certain embodiments, $R^5$ is ethyl. In certain embodiments, $R^5$ is optionally substituted aryl. In certain embodiments, $R^5$ is optionally substituted benzyl. In certain embodiments, $R^5$ is benzyl. In certain embodiments, $R^5$ is a nitrogen protecting group. In certain embodiments, $R^5$ is optionally substituted acyl. In certain embodiments, $R^5$ is $C_2H_5$C(═O)—. In certain embodiments, $R^5$ is $CH_3$C(═O)—.

As generally defined herein, $R^6$ is hydrogen, optionally substituted alkyl, optionally substituted alkenyl, optionally substituted alkynyl, optionally substituted carbocyclyl, optionally substituted aryl, optionally substituted heterocyclyl, optionally substituted heteroaryl, $—OR^A$, $—N(R^B)_2$, $—SR^A$, $—C(=O)R^C$, $—C(=O)OR^A$, $—C(=O)N(R^B)_2$, $—OC(=O)R^C$, $—OC(=O)N(R^B)_2$, $—NR^BC(=O)R^C$, $—NR^BC(=O)OR^A$, $—NR^BC(=O)N(R^B)_2$, $S(=O)R^C$, $—SO_2R^C$, $—NR^BSO_2R^C$, or $—SO_2N(R^B)_2$. In some embodiments, $R^6$ is hydrogen. In some embodiments, $R^6$ is optionally substituted $C_{1-6}$ alkyl. In certain embodiments, $R^6$ is methyl. In certain embodiments, $R^6$ is $—N(R^B)_2$, wherein each instance of $R^B$ is as generally defined herein. In certain embodiments, $R^6$ is $—NHR^B$, wherein $R^B$ is as generally defined herein. In certain embodiments, $R^6$ is $—NHR^B$, wherein $R^B$ is $—C(=O)R^{B6}$, and $R^{B6}$ is optionally substituted alkyl, optionally substituted aryl, optionally substituted carbocyclyl, optionally substituted hetercyclyl, or optionally substituted heteraryl. In certain embodiments, In certain embodiments, $R^6$ is $—NHC(=O)R^{B6}$, wherein $R^{B6}$ is optionally substituted alkyl. In certain embodiments, $R^6$ is $—NHC(=O)R^{B6}$, wherein $R^{B6}$ is unsubstituted alkyl. In certain embodiments, $R^6$ is $—NHC(=O)^tBu$. In certain embodiments, $R^6$ is $—NHC(=O)Bu$.

As generally defined herein, $R^7$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $—OR^A$, $—OC(=O)R^C$, $—C(=O)R^C$, $—C(=O)OR^A$, $—OC(=O)N(R^B)_2$, $—C(=O)N(R^B)_2$, $S(=O)R^C$, $—SO_2R^C$, $—SO_2N(R^B)_2$, or an oxygen protecting group. In certain embodiments, $R^7$ is hydrogen. In certain embodiments, $R^7$ is halogen. In certain embodiments, $R^7$ is F. In certain embodiments, $R^7$ is Cl. In certain embodiments, $R^7$ is Br. In certain embodiments, $R^7$ is I. In certain embodiments, $R^7$ is hydrogen, optionally substituted $C_{1-6}$ alkyl, or a nitrogen protecting group. In some embodiments, $R^7$ is hydrogen. In some embodiments, $R^7$ is optionally substituted $C_{1-6}$ alkyl. In certain embodiments, $R^7$ is methyl. In certain embodiments, $R^7$ is optionally substituted heterocyclyl (e.g., optionally substituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^7$ is optionally substituted piperidine. In certain embodiments, $R^7$ is

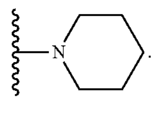 [SMILES: *N1CCCCC1]

In certain embodiments, $R^7$ is —OH. In certain embodiments, $R^7$ is —O(alkyl) (e.g., $—O(C_{1-6}$ alkyl)). In certain embodiments, $R^7$ is —OMe. In certain embodiments, $R^7$ is a oxygen protecting group. In certain embodiments, $R^7$ is optionally substituted acyl. In certain embodiments, $R^7$ is $C_2H_5C(=O)—$. In certain embodiments, $R^7$ is $CH_3C(=O)—$. In certain embodiments, $R^7$ is $—OC(=O)R^C$, wherein $R^C$ is optionally substituted alkyl. In certain embodiments, $R^7$ is $—OC(=O)CH_3$. In certain embodiments, $R^7$ is $—OC(=O)N(R^B)_2$, wherein $R^B$ is hydrogen or optionally substituted alkyl. In certain embodiments, $R^7$ is $—OC(=O)NH_2$. In certain embodiments, $R^7$ is $—OC(=O)NHCH_3$. In certain embodiments, $R^7$ is of the formula $—Y(R^A)$, wherein Y is O, S, Se, or N; and $R^A$ is $—COR^C$, $—COOR^C$, $—SO_2R^C$, $—CO(NH)R^C$, or $—SO_2(NH)R^C$. In certain embodiments, $R^7$ is $—OR^A$. In certain embodiments, $R^7$ is $—SR^A$. In certain embodiments, $R^7$ is $—SeR^A$. In certain embodiments, $R^7$ is $—NR^A$. In certain embodiments, $R^A$ is $—COR^C$. In certain embodiments, $R^A$ is $—COOR^C$. In certain embodiments, $R^A$ is $—SO_2R^C$. In certain embodiments, $R^A$ is $—CO(NH)R^C$. In certain embodiments, $R^A$ is $—SO_2(NH)R^C$.

As generally defined herein, $R^8$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^8$ is hydrogen. In certain embodiments, $R^8$ is halogen. In certain embodiments, $R^8$ is F. In certain embodiments, $R^8$ is Cl. In certain embodiments, $R^8$ is Br. In certain embodiments, $R^8$ is I. In certain embodiments, $R^8$ is hydrogen, optionally substituted $C_{1-6}$ alkyl, or a nitrogen protecting group. In some embodiments, $R^8$ is hydrogen. In some embodiments, $R^8$ is optionally substituted $C_{1-6}$ alkyl. In certain embodiments, $R^8$ is methyl. In certain embodiments, $R^8$ is ethyl.

In certain embodiments of Formula (II), $OR^7$ and $R^8$ are taken together to form C=O.

As generally described above, $R^{10}$ is hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, $—OR^A$, $—N(R^B)_2$, or $—SR^A$. In certain embodiments, $R^{10}$ is hydrogen. In some embodiments, $R^{10}$ is optionally substituted $C_{1-6}$ alkyl. In certain embodiments, $R^{10}$ is methyl.

As generally described above, $R^{11}$ is hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, $—OR^A$, $—N(R^B)_2$, or $—SR^A$. In certain embodiments, $R^{11}$ is hydrogen, optionally substituted alkyl, optionally substituted alkenyl, optionally substituted alkynyl, or optionally substituted phenyl. In certain embodiments, $R^{11}$ is hydrogen. In some embodiments, $R^{11}$ is optionally substituted $C_{1-6}$ alkyl. In some embodiments, $R^{11}$ is unsubstituted alkyl. In some embodiments, $R^{11}$ is methyl or ethyl. In certain embodiments, $R^{11}$ is ethyl. In some embodiments, $R^{11}$ is substituted alkyl. In some embodiments, $R^{11}$ is optionally substituted carbocyclylalkyl, optionally substituted haloalkyl, or optionally substituted alkoxyl.

As generally described above, $R^{12}$ is hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, $—OR^A$, $—N(R^B)_2$, or $—SR^A$. In certain embodiments, $R^{12}$ is hydrogen. In some embodiments, $R^{12}$ is optionally substituted $C_{1-6}$ alkyl. In certain embodiments, $R^{12}$ is methyl. In certain embodiments, $R^{12}$ is ethyl.

As generally described above, $R^{13}$ is hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, $—OR^A$, $—N(R^B)_2$, or $—SR^A$. In certain embodiments, $R^{13}$ is hydrogen. In some embodiments, $R^{13}$ is optionally substituted $C_{1-6}$ alkyl. In certain embodiments, $R^{13}$ is methyl.

In certain embodiments, $R^{12}$ and $R^{13}$ are taken together to form an optionally substituted alkenyl moiety of Formula (i):

(i)

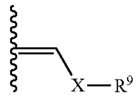

wherein:

X is a bond, S, Se, or O; $R^9$ is hydrogen, optionally substituted alkyl, optionally substituted alkenyl, optionally substituted aryl, optionally substituted heterocyclyl, or optionally substituted heteroaryl. In certain embodiments, $R^{12}$ and $R^{13}$ are taken together to form an optionally substituted alkenyl moiety of Formula (i-a):

(i-a)

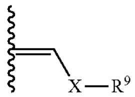

wherein:

X is a bond, S, Se, NH, or O;

$R^9$ is hydrogen, optionally substituted alkyl, optionally substituted alkenyl, optionally substituted aryl, optionally substituted heterocyclyl, or optionally substituted heteroaryl. In some embodiments, $R^9$ is hydrogen. In some embodiments, $R^9$ is optionally substituted $C_{1-6}$ alkyl. In certain embodiments, $R^9$ is unsubstituted $C_{1-6}$ alkyl. In certain embodiments, $R^9$ is methyl or ethyl. In certain embodiments, $R^9$ is substituted $C_{1-6}$ alkyl. In certain embodiments, $R^9$ is optionally substituted $C_{1-6}$ haloalkyl. In certain embodiments, $R^9$ is —$CH_2F$, —$CHF_2$, or —$CF_3$. In certain embodiments, $R^9$ is optionally substituted alkenyl$C_{1-6}$ alkyl. In certain embodiments, $R^9$ is allyl. In certain embodiments, $R^9$ is optionally substituted carbocyclyl. In certain embodiments, $R^9$ is optionally substituted cyclopropyl. In certain embodiments, $R^9$ is optionally substituted aryl. In certain embodiments, $R^9$ is optionally substituted phenyl. In certain embodiments, $R^9$ is Ph.

In certain embodiments, X is a bond. In certain embodiments, $R^{12}$ and $R^{13}$ are taken together to form

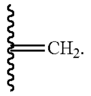

In certain embodiments, X is —NH—. In certain embodiments, X is O. In certain embodiments, X is S. In certain embodiments, X is Se.

In certain embodiments, the optionally substituted alkenyl moiety of Formula (i) is of Formula (i-1):

(i-1)

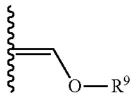

wherein $R^9$ is hydrogen, substituted alkyl, optionally substituted alkenyl, optionally substituted aryl, optionally substituted heterocyclyl, or optionally substituted heteroaryl. In certain embodiments, $R^9$ is substituted $C_{1-6}$ alkyl. In certain embodiments, $R^9$ is optionally substituted $C_{1-6}$ haloalkyl. In certain embodiments, $R^9$ is —$CH_2F$, —$CHF_2$, or —$CF_3$. In certain embodiments, the optionally substituted alkenyl moiety of Formula (i) is

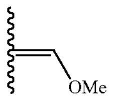 [SMILES: *=COC]

In certain embodiments, the optionally substituted alkenyl moiety of Formula (i) is of Formula (i-2):

(i-2)

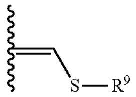

wherein $R^9$ is hydrogen, optionally substituted alkyl, optionally substituted alkenyl, optionally substituted aryl, optionally substituted heterocyclyl, or optionally substituted heteroaryl. In certain embodiments, $R^9$ is optionally substituted $C_{1-6}$ alkyl. In certain embodiments, $R^9$ is unsubstituted $C_{1-6}$ alkyl. In certain embodiments, $R^9$ is methyl or ethyl. In certain embodiments, $R^9$ is substituted $C_{1-6}$ alkyl. In certain embodiments, $R^9$ is optionally substituted $C_{1-6}$ haloalkyl. In certain embodiments, $R^9$ is —$CH_2F$, —$CHF_2$, or —$CF_3$.

In certain embodiments, the optionally substituted alkenyl moiety of Formula (i) is of Formula (i-3):

(i-3)

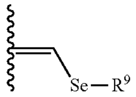

wherein $R^9$ is hydrogen, optionally substituted alkyl, optionally substituted alkenyl, optionally substituted aryl, optionally substituted heterocyclyl, or optionally substituted heteroaryl. In certain embodiments, $R^9$ is optionally substituted $C_{1-6}$ alkyl. In certain embodiments, $R^9$ is unsubstituted $C_{1-6}$ alkyl. In certain embodiments, $R^9$ is methyl or ethyl. In certain embodiments, $R^9$ is substituted $C_{1-6}$ alkyl. In certain embodiments, $R^9$ is optionally substituted $C_{1-6}$ haloalkyl. In certain embodiments, $R^9$ is —$CH_2F$, —$CHF_2$, or —$CF_3$. In certain embodiments, the optionally substituted alkenyl moiety of Formula (i) is of Formula (i-4):

(i-4)

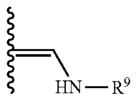

wherein $R^9$ is hydrogen, optionally substituted alkyl, optionally substituted alkenyl, optionally substituted aryl, optionally substituted heterocyclyl, or optionally substituted heteroaryl. In certain embodiments, $R^9$ is optionally substituted $C_{1-6}$ alkyl. In certain embodiments, $R^9$ is unsubstituted $C_{1-6}$ alkyl. In certain embodiments, $R^9$ is methyl or ethyl. In certain embodiments, $R^9$ is substituted $C_{1-6}$ alkyl. In certain embodiments, $R^9$ is optionally substituted $C_{1-6}$ haloalkyl. In certain embodiments, $R^9$ is —$CH_2F$, —$CHF_2$, or —$CF_3$. As generally described above, $R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^{14}$ is hydrogen. In some embodiments, $R^{14}$ is optionally substituted $C_{1-6}$ alkyl. In certain embodiments, $R^{14}$ is methyl. In some embodiments, $R^{14}$ is an oxygen protecting group. In some embodiments, $R^{14}$ is optionally substituted acyl. In some embodiments, $R^{14}$ is optionally substituted acetyl.

In certain embodiments, when $R^{12}$ and $R^{13}$ are taken together to form an optionally substituted alkenyl moeity, $R^2$ is hydrogen, and at least one of $R^1$, $R^3$, and $R^4$ is substituted. In certain embodiments, when $R^{12}$ and $R^{13}$ are taken together to form a substituted alkenyl moeity, $R^2$ is hydrogen, and at least one of $R^1$, $R^3$, and $R^4$ is substituted. In certain embodiments, when $R^{12}$ and $R^{13}$ are taken together to form an optionally substituted alkenyl moiety, $R^2$, $R^3$, and $R^4$ are hydrogen, $R^1$ is selected from the group consisting of halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$N(R^B)_2$, —$SR^A$, —$SeR^A$, —$C(=O)R^C$, —$C(=O)OR^A$, —$C(=O)N(R^B)_2$, —$OC(=O)R^C$, —$OC(=O)N(R^B)_2$, —$NR^BC(=O)R^C$, —$NR^BC(=O)OR^A$, —$NR^BC(=O)N(R^B)_2$, $S(=O)R^C$, —$SO_2R^C$, —$NR^BSO_2R^C$, and —$SO_2N(R^B)_2$. In certain embodiments, when $R^{12}$ and $R^{13}$ are taken together to form a substituted alkenyl moiety, $R^2$, $R^3$, and $R^4$ are hydrogen, $R^1$ is selected from the group consisting of halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$N(R^B)_2$, —$SR^A$, —$SeR^A$, —$C(=O)R^C$, —$C(=O)OR^A$, —$C(=O)N(R^B)_2$, —$OC(=O)R^C$, —$OC(=O)N(R^B)_2$, —$NR^BC(=O)R^C$, —$NR^BC(=O)OR^A$, —$NR^BC(=O)N(R^B)_2$, $S(=O)R^C$, —$SO_2R^C$, —$NR^BSO_2R^C$, and —$SO_2N(R^B)_2$. In certain embodiments, when $R^{12}$ and $R^{13}$ are taken together to form an optionally substituted alkenyl moiety, $R^1$ and $R^2$ are hydrogen, and at least one of $R^3$ and $R^4$ is substituted. In certain embodiments, when $R^{12}$ and $R^{13}$ are taken together to form an optionally substituted alkenyl moiety, $R^1$ and $R^2$ are hydrogen, and one of $R^3$ and $R^4$ is substituted. In certain embodiments, when $R^{12}$ and $R^{13}$ are taken together to form an optionally substituted alkenyl moiety, $R^1$ and $R^2$ are hydrogen, and both of $R^3$ and $R^4$ are substituted. In certain embodiments, when $R^{12}$ and $R^{13}$ are taken together to form an optionally substituted alkenyl moiety, $R^2$ and $R^3$ are hydrogen, and $R^1$ and $R^4$ are substituted. In certain embodiments, when $R^{12}$ and $R^{13}$ are taken together to form an optionally substituted alkenyl moiety, $R^2$ and $R^4$ are hydrogen, and $R^1$ and $R^3$ are substituted. In certain embodiments, when $R^{12}$ and $R^{13}$ are taken together to form an optionally substituted alkenyl moiety, $R^2$ is hydrogen, and $R^1$, $R^2$, and $R^4$ are substituted.

In certain embodiments, $R^1$ is —$OR^A$, wherein $R^A$ is as generally defined herein; and $R^{11}$ is optionally substituted alkyl. In certain embodiments, $R^1$ is —$OR^A$, wherein $R^A$ is hydrogen or optionally substituted alkyl; and $R^{11}$ is optionally substituted alkyl. In certain embodiments, $R^1$ is —$OR^A$, wherein $R^A$ is as generally defined herein; and $R^{11}$ is optionally substituted alkyl. In certain embodiments, $R^1$ is —$OCH_3$; and $R^{11}$ is unsubstituted alkyl (e.g. methyl or ethyl).

In certain embodiments, $R^1$ is —$OR^A$, wherein $R^A$ is as generally defined herein; $R^{11}$ is optionally substituted alkyl; and $R^6$ is hydrogen. In certain embodiments, $R^1$ is —$OR^A$, wherein $R^A$ is hydrogen or optionally substituted alkyl; $R^{11}$ is optionally substituted alkyl; and $R^6$ is hydrogen. In certain embodiments, $R^1$ is —$OR^A$, wherein $R^A$ is as generally defined herein; $R^{11}$ is optionally substituted alkyl; and $R^6$ is hydrogen. In certain embodiments, $R^1$ is —$OCH_3$; and $R^{11}$ is unsubstituted alkyl (e.g. methyl or ethyl); and $R^6$ is hydrogen.

As generally described above, $R^{15}$ is hydrogen, halogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N_3$, —$OR^A$, —$N(R^B)_2$, or —SRA. In certain embodiments, $R^{15}$ is hydrogen. In certain embodiments, $R^{15}$ is halogen (e.g., F, Cl, Br, or I). In certain embodiments, $R^{15}$ is optionally substituted acyl (e.g., acetyl, —$COR^A$, or —$CON(R^B)_2$). In certain embodiments, $R^{15}$ is —COMe. In certain embodiments, $R^{15}$ is —$CON(Me)_2$. In certain embodiments, $R^{15}$ is optionally substituted alkyl (e.g., optionally substituted $C_{1-6}$ alkyl). In certain embodiments, $R^{15}$ is methyl. In certain embodiments, $R^{15}$ is optionally substituted alkenyl (e.g., optionally substituted $C_{2-6}$ alkenyl). In certain embodiments $R^{15}$ is optionally substituted alkynyl (e.g., optionally substituted $C_{2-6}$ alkynyl). In certain embodiments, $R^{15}$ is optionally substituted carbocyclyl (e.g., optionally substituted, 3- to 7-membered, monocyclic carbocyclyl comprising zero, one, or two double bonds in the carbocyclic ring system). In certain embodiments, $R^{15}$ is optionally substituted heterocyclyl (e.g., optionally substituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{15}$ is optionally substituted aryl (e.g., optionally substituted, 6- to 10-membered aryl). In certain embodiments, $R^{15}$ is optionally substituted heteroaryl (e.g., optionally substituted, 5- to 6-membered, monocyclic heteroaryl, wherein one, two, three, or four atoms in the heteroaryl ring system are independently nitrogen, oxygen, or sulfur, or optionally substituted, 9- to 10-membered, bicyclic heteroaryl, wherein one, two, three, or four atoms in the heteroaryl ring system are independently nitrogen, oxygen, or sulfur). In certain embodiments, $R^{15}$ is —$OR^A$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, $R^{15}$ is —$SR^A$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{15}$ is —$N(R^B)_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{15}$ is —CN. In certain embodiments, $R^{15}$ is —$N_3$.

As generally described above, $R^{16}$ is hydrogen, halogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N_3$, —$OR^A$, —$N(R^B)_2$, or —$SR^A$. In certain embodiments, $R^{16}$ is hydrogen. In certain embodiments, $R^{16}$ is halogen (e.g., F, Cl, Br, or I). In certain embodiments, $R^{16}$ is optionally substituted acyl (e.g., acetyl, —$COR^A$, or —$CON(R^B)_2$). In certain embodiments, $R^{16}$ is —COMe. In certain embodiments, $R^{16}$ is —$CON(Me)_2$. In certain embodiments, $R^{16}$ is optionally substituted alkyl (e.g., optionally substituted $C_{1-6}$ alkyl). In certain embodiments, $R^{16}$ is methyl. In certain embodiments, $R^{16}$ is optionally substituted alkenyl (e.g., optionally substituted $C_{2-6}$ alkenyl). In certain embodiments $R^{16}$ is optionally substituted alkynyl (e.g., optionally substituted $C_{2-6}$ alkynyl). In certain embodiments, $R^{16}$ is optionally substituted carbocyclyl (e.g., optionally substituted, 3- to 7-membered, monocyclic carbocyclyl comprising zero, one, or two double bonds in the carbocyclic ring system). In certain embodiments, $R^{16}$ is optionally substituted heterocyclyl (e.g., optionally substituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{16}$ is optionally substituted aryl (e.g., optionally substituted, 6- to 10-membered aryl). In certain embodiments, $R^{16}$ is optionally substituted heteroaryl (e.g., optionally substituted, 5- to 6-membered, monocyclic heteroaryl, wherein one, two, three, or four atoms in the heteroaryl ring system are independently nitrogen, oxygen, or sulfur, or optionally substituted, 9- to 10-membered, bicyclic heteroaryl, wherein one, two, three, or four atoms in the heteroaryl ring system are independently nitrogen, oxygen, or sulfur). In certain embodiments, $R^{16}$ is —$OR^A$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, $R^{16}$ is —$SR^A$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{16}$ is —$N(R^B)_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{16}$ is —CN. In certain embodiments, $R^{16}$ is —$N_3$.

As generally described above, $R^{17}$ is hydrogen, halogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, or —SRA. In certain embodiments, $R^{17}$ is hydrogen. In certain embodiments, $R^{17}$ is halogen (e.g., F, Cl, Br, or I). In certain embodiments, $R^{17}$ is optionally substituted acyl (e.g., acetyl). In certain embodiments, $R^{17}$ is optionally substituted alkyl (e.g., optionally substituted $C_{1-6}$ alkyl). In certain embodiments, $R^{17}$ is methyl. In certain embodiments, $R^{17}$ is optionally substituted alkenyl (e.g., optionally substituted $C_{2-6}$ alkenyl). In certain embodiments $R^{17}$ is optionally substituted alkynyl (e.g., optionally substituted $C_{2-6}$ alkynyl). In certain embodiments, $R^{17}$ is optionally substituted carbocyclyl (e.g., optionally substituted, 3- to 7-membered, monocyclic carbocyclyl comprising zero, one, or two double bonds in the carbocyclic ring system). In certain embodiments, $R^{17}$ is optionally substituted heterocyclyl (e.g., optionally substituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{17}$ is optionally substituted aryl (e.g., optionally substituted, 6- to 10-membered aryl). In certain embodiments, $R^{17}$ is optionally substituted heteroaryl (e.g., optionally substituted, 5- to 6-membered, monocyclic heteroaryl, wherein one, two, three, or four atoms in the heteroaryl ring system are independently nitrogen, oxygen, or sulfur, or optionally substituted, 9- to 10-membered, bicyclic heteroaryl, wherein one, two, three, or four atoms in the heteroaryl ring system are independently nitrogen, oxygen, or sulfur). In certain embodiments, $R^{17}$ is —$OR^A$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, $R^{17}$ is —$SR^A$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{17}$ is —$N(R^B)_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)).

As generally described above, $R^{18}$ is hydrogen, halogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, or —SRA. In certain embodiments, $R^{18}$ is hydrogen. In certain embodiments, $R^{18}$ is halogen (e.g., F, Cl, Br, or I). In certain embodiments, $R^{17}$ is optionally substituted acyl (e.g., acetyl). In certain embodiments, $R^{18}$ is optionally substituted alkyl (e.g., optionally substituted $C_{1-6}$ alkyl). In certain embodiments, $R^{18}$ is methyl. In certain embodiments, $R^{18}$ is optionally substituted alkenyl (e.g., optionally substituted $C_{2-6}$ alkenyl). In certain embodiments $R^{18}$ is optionally substituted alkynyl (e.g., optionally substituted $C_{2-6}$ alkynyl). In certain embodiments, $R^{18}$ is optionally substituted carbocyclyl (e.g., optionally substituted, 3- to 7-membered, monocyclic carbocyclyl comprising zero, one, or two double bonds in the carbocyclic ring system). In certain embodiments, $R^{18}$ is optionally substituted heterocyclyl (e.g., optionally substituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{18}$ is optionally substituted aryl (e.g., optionally substituted, 6- to 10-membered aryl). In certain embodiments, $R^{18}$ is optionally substituted heteroaryl (e.g., optionally substituted, 5- to 6-membered, monocyclic heteroaryl, wherein one, two, three, or four atoms in the heteroaryl ring system are independently nitrogen, oxygen, or sulfur, or optionally substituted, 9- to 10-membered, bicyclic heteroaryl, wherein one, two, three, or four atoms in the heteroaryl ring system are independently nitrogen, oxygen, or sulfur). In certain embodiments, $R^{18}$ is —$OR^A$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, $R^{17}$ is —$SR^A$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{18}$ is —$N(R^B)_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{17}$ and $R^{18}$ are the same. In certain embodiments, $R^{17}$ and $R^{18}$ are different from each other. In certain embodiments, $R^{17}$ and $R^{18}$ are both H. In certain embodiments, $R^{17}$ and $R^{18}$ are taken together to form

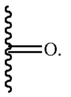 [SMILES: *=O]

In certain embodiments, provided herein are the isotopically labeled derivatives of any one of Formulae (I')-(II'). In certain embodiments, provided herein are the isotopically labeled derivatives of any one of Formulae (I)-(II). As used herein, and unless otherwise specified, the atoms of the compounds provided herein are meant to represent any stable or radioactive isotope of that atom. In certain embodiments, a compound provided herein encompasses all possible isotopic variants of that compound. For example, as used herein, and unless otherwise specified, hydrogen encompasses proton ($^1H$), deuterium ($^2H$), tritium ($^3H$), and/or mixtures thereof. In one embodiment, when a position is designated as “H” or “hydrogen”, the position is understood to have hydrogen at its natural isotopic composition. In one embodiment, when a position is designated as “H” or “hydrogen”, the position is understood to have hydrogen at an isotopically enriched composition, i.e., an isotopic composition other than the natural isotopic composition of that atom. In one embodiment, the compounds provided herein optionally comprise deuterium at one or more positions where hydrogen atoms are present, and wherein the deuterium composition of the atom or atoms is other than the natural isotopic composition. In one embodiment, the compounds provided herein optionally comprise isotopes for other elements at one or more positions, including but not limited to, $^{11}C$, $^{13}C$, $^{14}C$, $^{33}S$, $^{34}S$, $^{36}S$, $^{15}N$, $^{17}O$, and/or $^{18}O$, and wherein the isotopic composition of the atom or atoms is other than the natural isotopic composition. In certain embodiments, the provided compounds are isotopic labeled with one or more isotopes selected from the group consisted of $^3H$, $^{14}C$, $^{11}C$, $^{13}N$, $^{15}O$, and $^{18}F$. In certain embodiments, the provided compounds are isotopic labeled with $^3H$. In certain embodiments, the provided compounds are isotopic labeled with $^{14}C$.

As used herein, and unless otherwise specified, the term “isotopically labeled derivative” refers to a compound that contains an unnatural proportion of an isotope at one or more of the atoms that constitute such a compound. In certain embodiments, an “isotopic derivative” of a compound contains unnatural proportions of one or more isotopes, including, but not limited to, hydrogen ($^1H$), deuterium ($^2H$), tritium ($^3H$), carbon 11 ($^{11}C$), carbon 12 ($^{12}C$), carbon 13 ($^{13}C$), carbon-14, ($^{14}O$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$) iodine-125 ($^{125}I$), iodine-127 ($^{127}I$), iodine-129 ($^{129}I$), and iodine-131 ($^{131}I$). In certain embodiments, an “isotopic derivative” of a compound is in a stable form, that is, non-radioactive. In certain embodiments, an “isotopic derivative” of a compound contains unnatural proportions of one or more isotopes, including, but not limited to, hydrogen ($^1H$), deuterium ($^2H$), tritium ($^3H$), carbon 11 ($^{11}C$), carbon 12 ($^{12}C$), carbon 13 ($^{13}C$), carbon-14, ($^{14}O$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an “isotopic derivative” of a compound is in an unstable form, that is, radioactive. In certain embodiments, an “isotopic derivative” of a compound contains unnatural proportions of one or more isotopes, including, but not limited to, hydrogen ($^1H$), deuterium ($^2H$), tritium ($^3H$), carbon 11 ($^{11}C$), carbon 12 ($^{12}C$), carbon 13 ($^{13}C$), carbon-14, ($^{14}O$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). It will be understood that, in a compound as provided herein, any hydrogen can be $^3H$, for example, or any carbon can be $^{13}C$, for example, or any nitrogen can be $^{15}N$, for example, or any oxygen can be $^{18}O$, for example, where feasible according to the judgment of one of skill.

In certain embodiments, a compound of Formula (I') is of one of the following formulae:

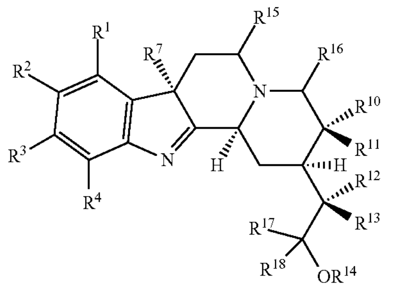

or

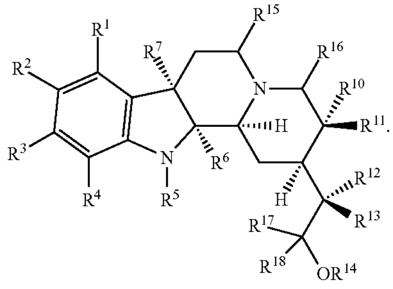

In certain embodiments, a compound of Formula (I') is of one of the following formulae:

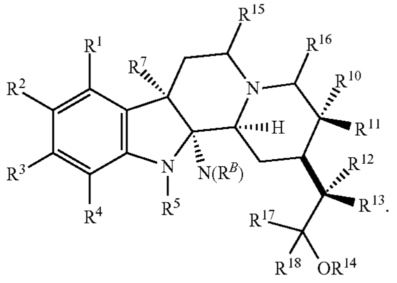

In certain embodiments, a compound of Formula (I) is of one of the following formulae:

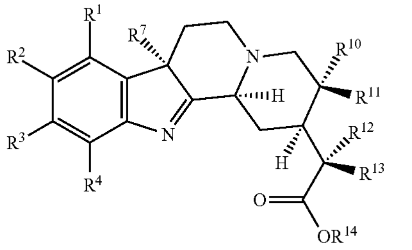

or

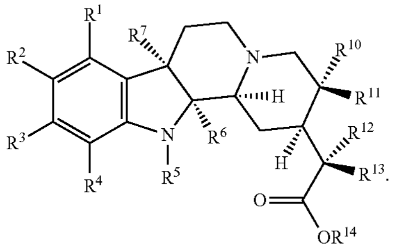

In certain embodiments, a compound of Formula (I) is of the following formulae:

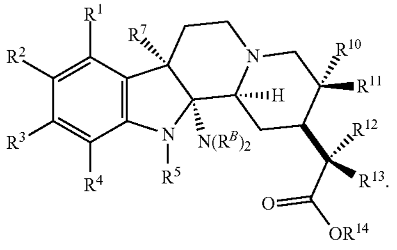

In certain embodiments, a compound of Formula (II') is of one of the following formulae:

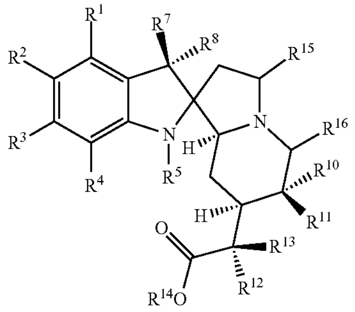

or

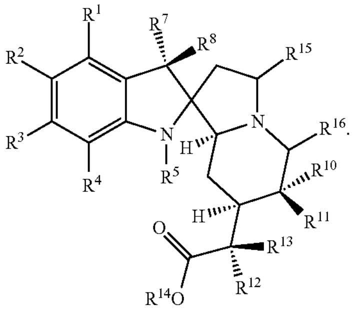

In certain embodiments, a compound of Formula (II) is of one of the following formulae:

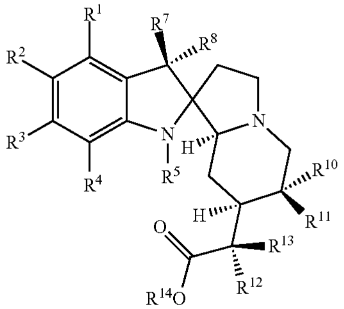

or

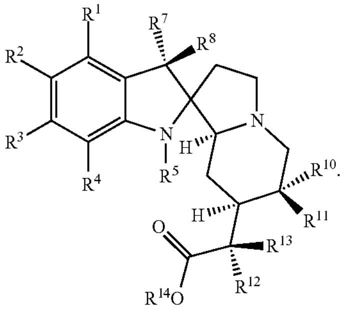

In certain embodiments, a provided compound is of Formula (I-a'):

(I-a')

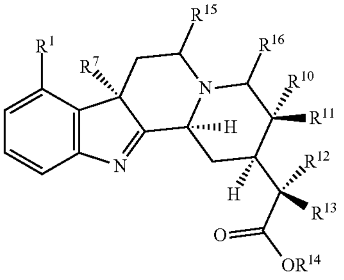

or a pharmaceutically acceptable salt thereof.

In certain embodiments, a provided compound is of Formula (I-a):

(I-a)

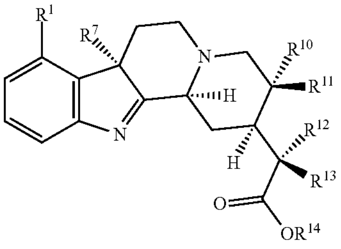

or a pharmaceutically acceptable salt thereof.

In certain embodiments, a provided compound is of Formula (I-b'):

(I-b')

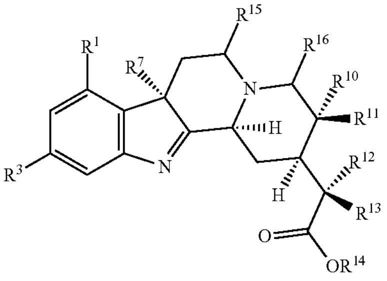

or a pharmaceutically acceptable salt thereof.

In certain embodiments a provided compound is of Formula (I-b):

(I-b)

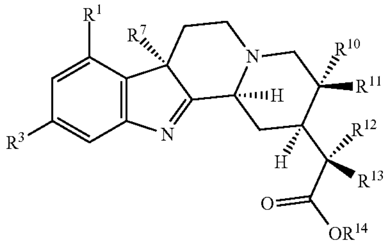

or a pharmaceutically acceptable salt thereof.

In certain embodiments, a provided compound is of Formula (I-c'):

(I-c')

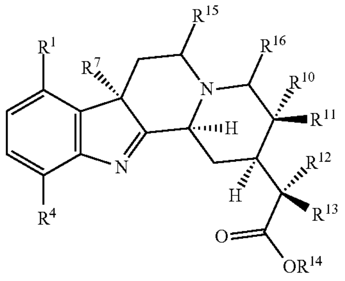

or a pharmaceutically acceptable salt thereof.

In certain embodiments, a provided compound is of Formula (I-c):

(I-c)

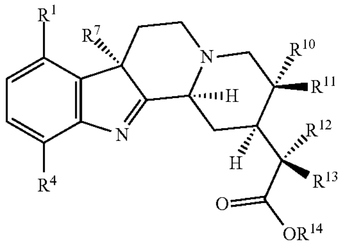

or a pharmaceutically acceptable salt thereof.

In certain embodiments, a provided compound is of Formula (I-d'):

(I-d')

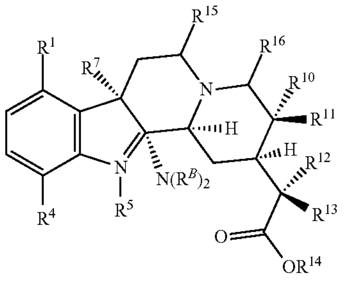

or a pharmaceutically acceptable salt thereof.

In certain embodiments, a provided compound is of Formula (I-d):

(I-d)

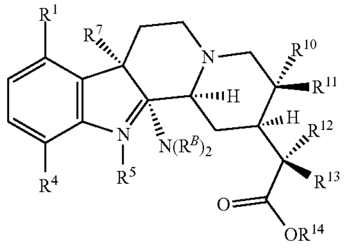

or a pharmaceutically acceptable salt thereof.

In certain embodiments, a provided compound is of Formula (II-a'):

(II-a')

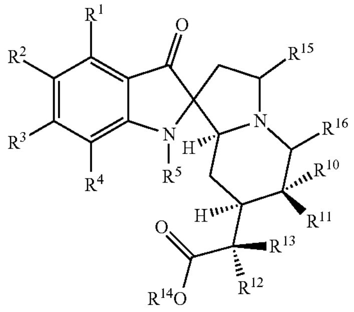

or a pharmaceutically acceptable salt thereof.

In certain embodiments, a provided compound is of Formula (II-a):

(II-a)

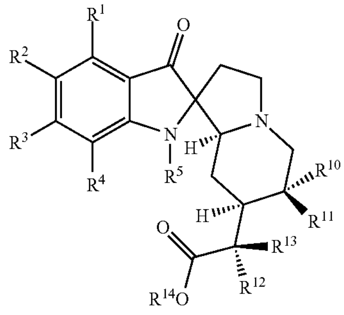

or a pharmaceutically acceptable salt thereof.

In certain embodiments, a provided compound is of Formula (II-a-i'):

(II-a-i')

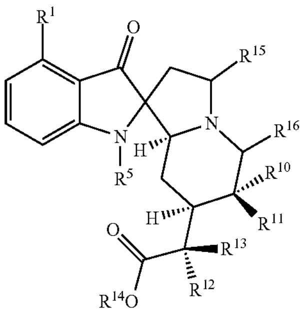

or a pharmaceutically acceptable salt thereof.

In certain embodiments, a provided compound is of Formula (II-a-i):

(II-a-i)

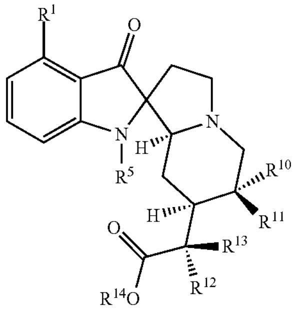

or a pharmaceutically acceptable salt thereof.

In certain embodiments, a provided compound is of Formula (II-a-ii'):

(II-a-ii')

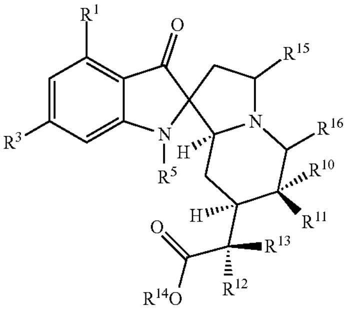

or a pharmaceutically acceptable salt thereof.

In certain embodiments, a provided compound is of Formula (II-a-ii):

(II-a-ii)

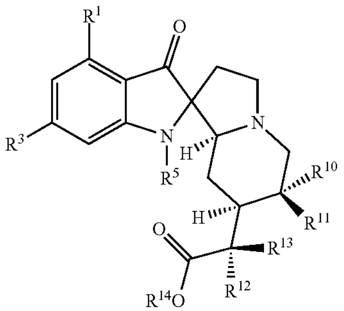

or a pharmaceutically acceptable salt thereof.

In certain embodiments, a provided compound is of Formula (II-a-iii'):

(II-a-iii')

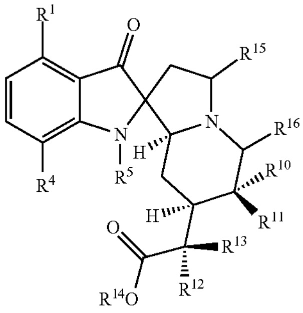

or a pharmaceutically acceptable salt thereof.

In certain embodiments, a provided compound is of Formula (II-a-iii):

(II-a-iii)

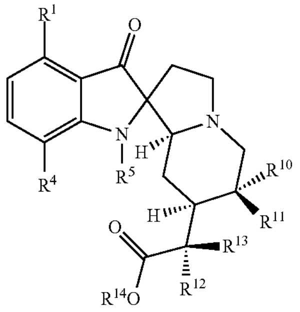

or a pharmaceutically acceptable salt thereof.

In certain embodiments, a provided compound is of Formula (II-b'):

(II-b')

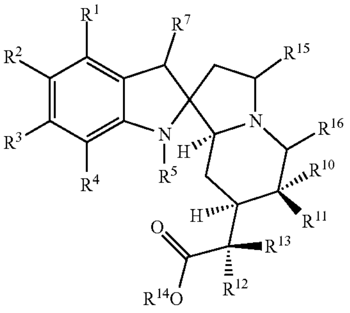

or a pharmaceutically acceptable salt thereof.

In certain embodiments, a provided compound is of Formula (II-b):

(II-b)

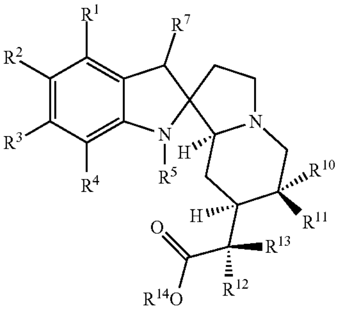

or a pharmaceutically acceptable salt thereof.

In certain embodiments, a provided compound is of one of the following formulae:

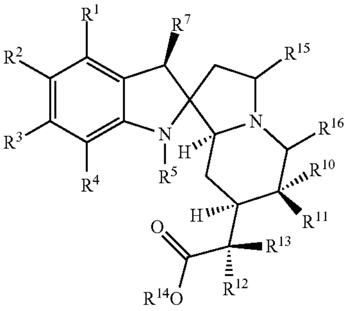

or

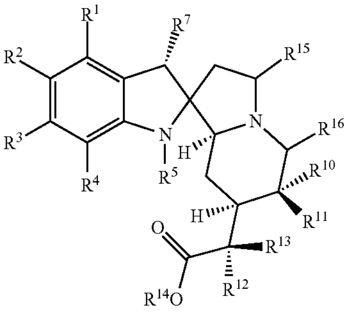

or a pharmaceutically acceptable salt thereof.

In certain embodiments, a provided compound is of one of the following formulae:

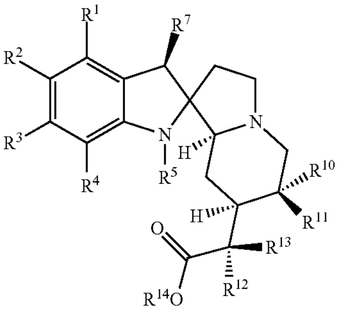

or

-continued

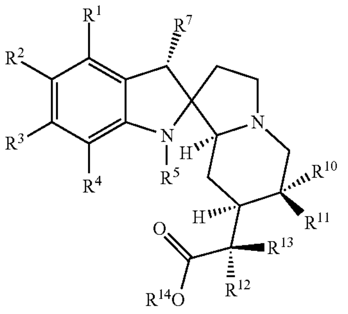

or a pharmaceutically acceptable salt thereof.

In certain embodiments, a provided compound is of Formula (II-b-i'):

(II-b-i')

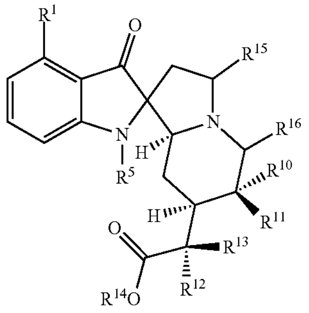

or a pharmaceutically acceptable salt thereof.

In certain embodiments, a provided compound is of Formula (II-b-i):

(II-b-i)

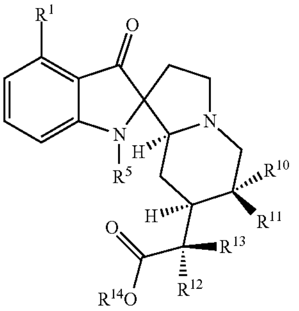

or a pharmaceutically acceptable salt thereof.

In certain embodiments, a provided compound is of one of the following formulae:

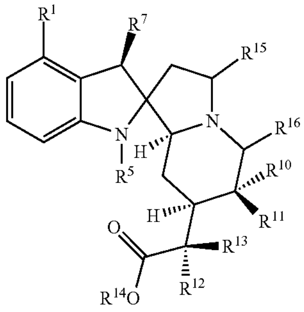

or

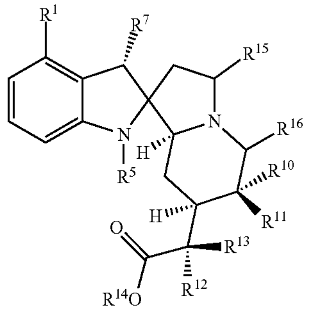

or a pharmaceutically acceptable salt thereof.

In certain embodiments, a provided compound is of one of the following formulae:

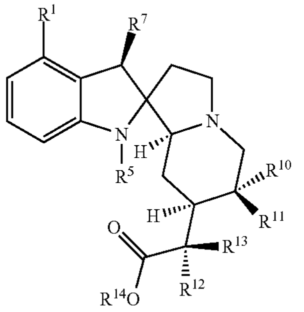

or

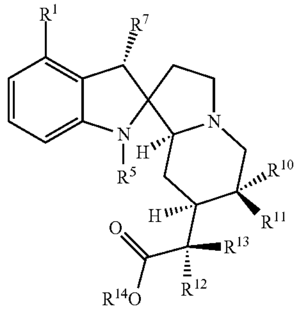

or a pharmaceutically acceptable salt thereof.

In certain embodiments, an exemplary compound of Formula (I') is of the following formula:

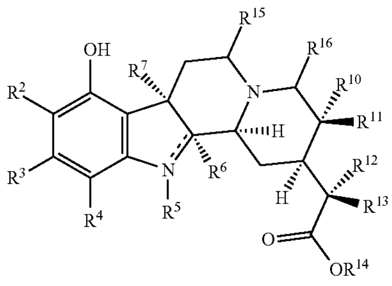
or a pharmaceutically acceptable salt thereof.
In certain embodiments, an exemplary compound of Formula (I) is of the following formula:
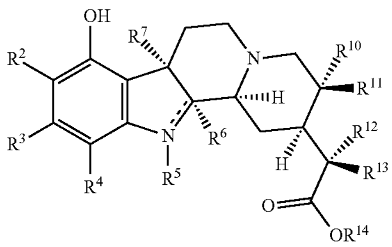
or a pharmaceutically acceptable salt thereof.
In certain embodiments, an exemplary compound of Formula (I') is:
(VM1500)
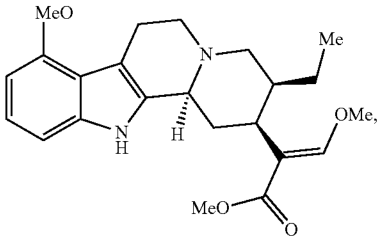
(VM1501)
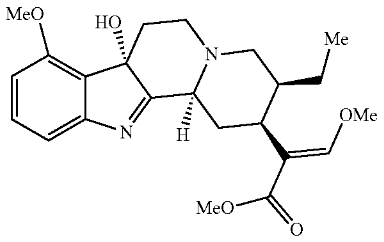
(VM1517)
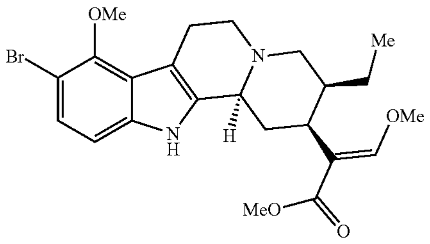
-continued
(VM1518)
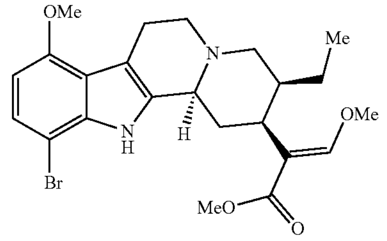
(VM1519)
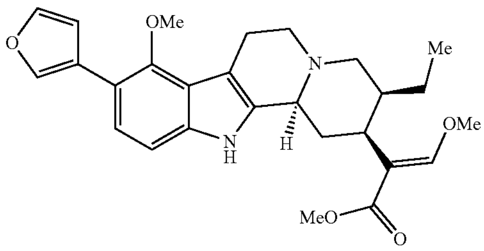
(VM1520)
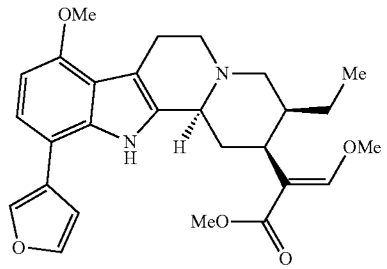
(VM1521)
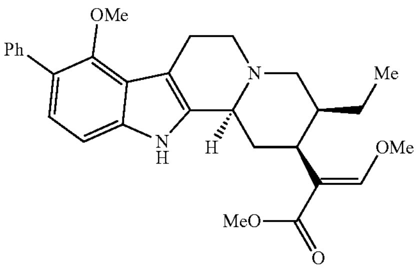
(VM1532)
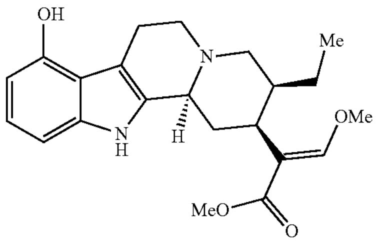
(VM1533)
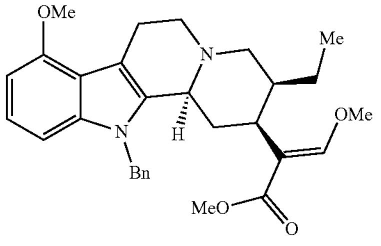

-continued
(VM1539)
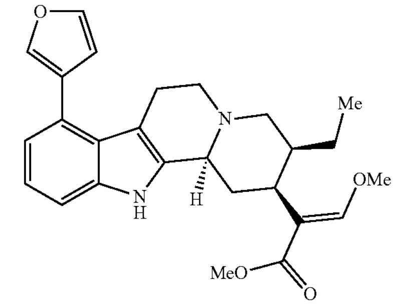
(VM1540)
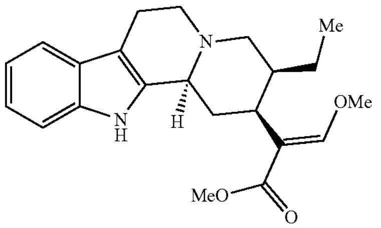
(VM1541)
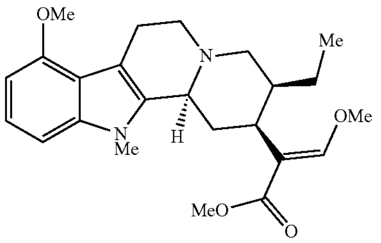
(VM1542)
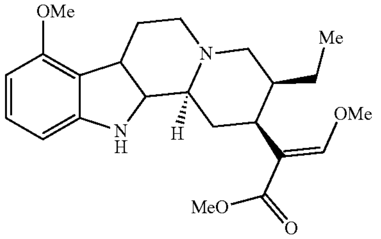
(VM1522)
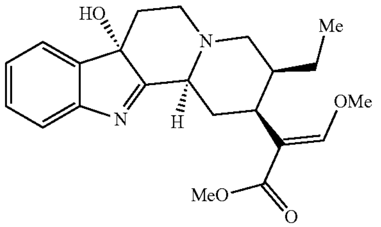
(VM1523)
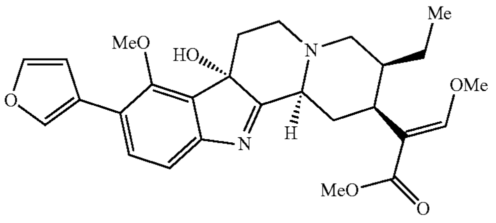
-continued
(VM1524)
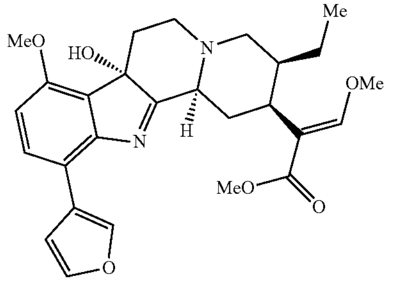
(VM1525)
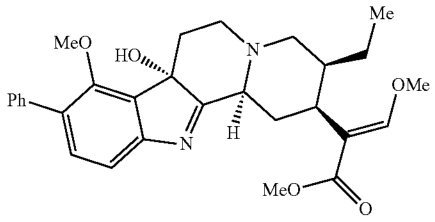
(VM1526)
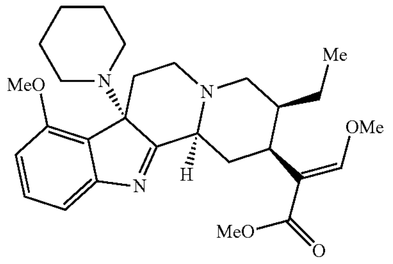
(VM1537)
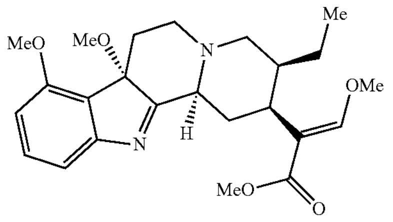
(VM1538)
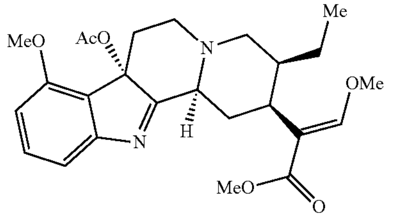
(VM1527)
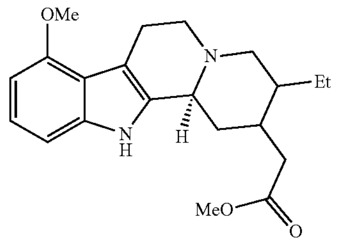

-continued (VM1528)

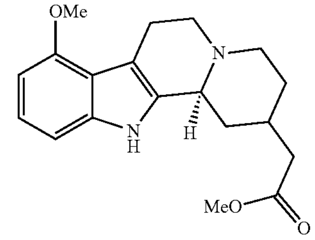

(VM1529)

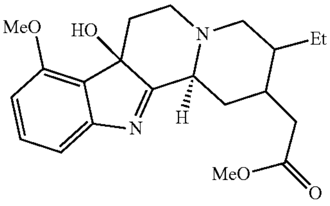

(VM1531)

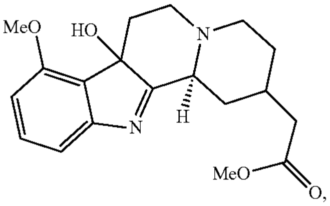

(VM1534)

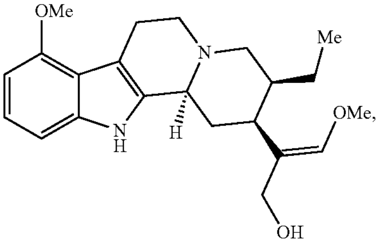

(VM1535)

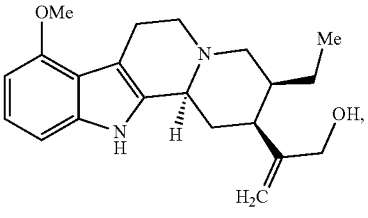

(VM1536)

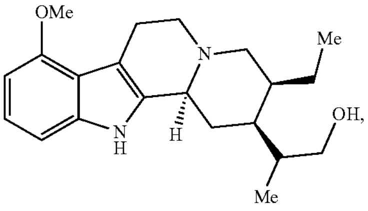

or a pharmaceutically acceptable salt thereof.

In certain embodiments, an exemplary compound of Formula (I) is:

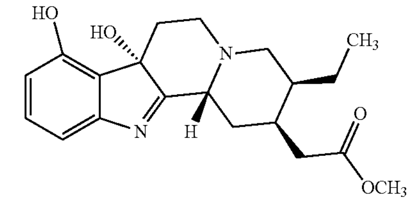

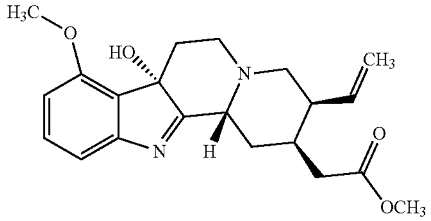

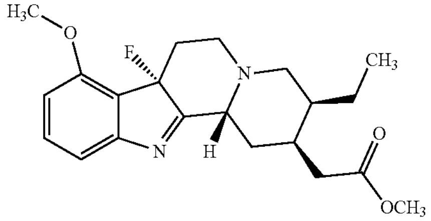

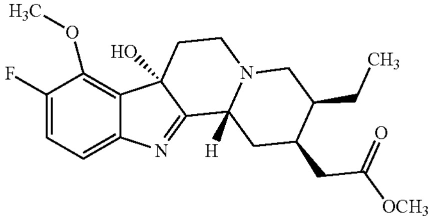

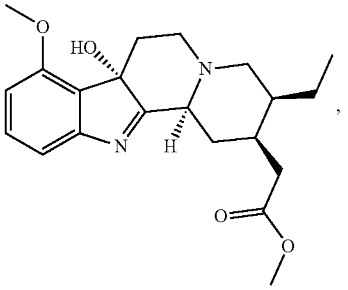

or a pharmaceutically acceptable salt thereof.

In certain embodiments, an exemplary compound of Formula (II') is of the following formula:

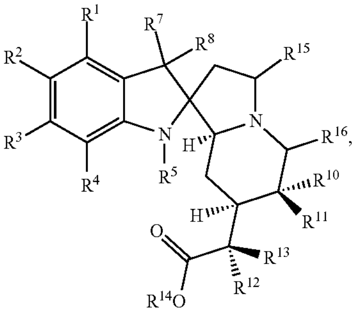

or a pharmaceutically acceptable salt thereof.

In certain embodiments, an exemplary compound of Formula (II) is of the following formula:

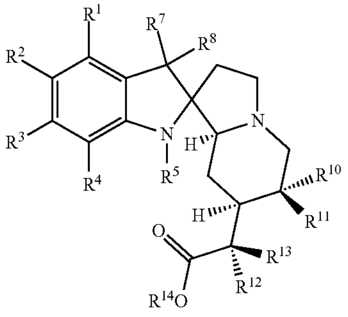
or a pharmaceutically acceptable salt thereof.
In certain embodiments, an exemplary compound of Formula (II') is of the following formula:
(VM1502)
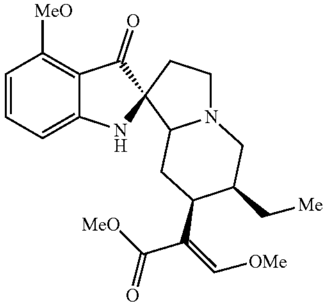
(VM1507)
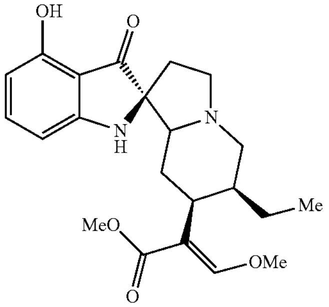
(VM1503)
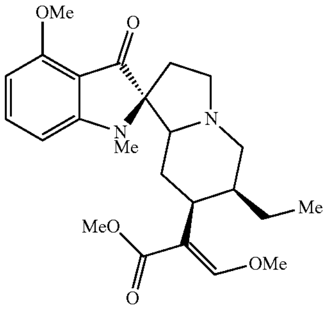
-continued
(VM1505)
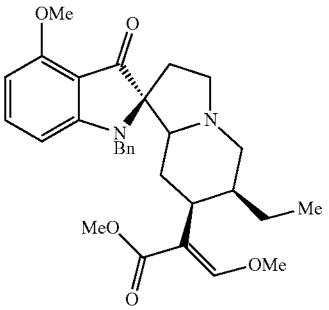
(VM1506)
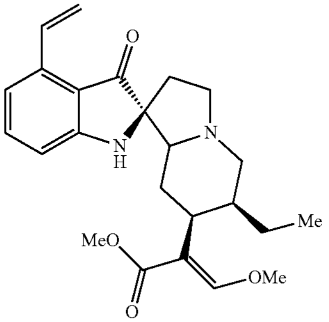
(VM1508)
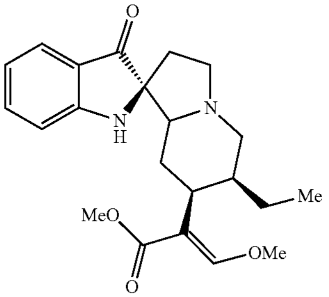
(VM1509)
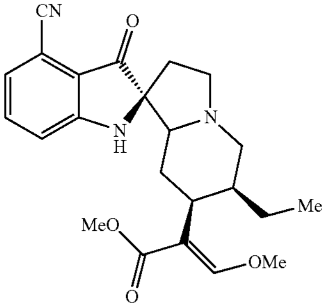
(VM1510)
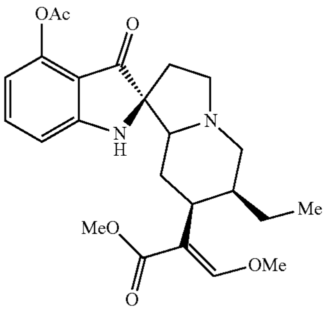

-continued
(VM1511)
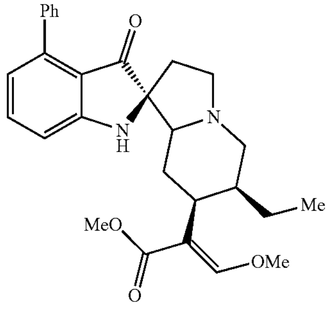
(VM1512)
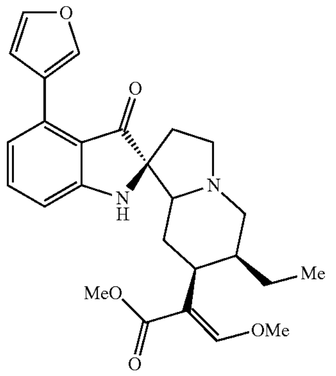
(VM1513)
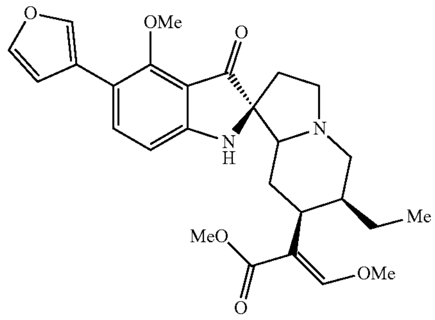
(VM1514)
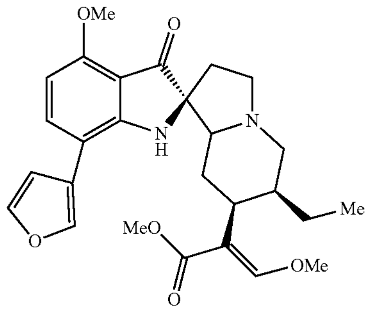
(VM1515)
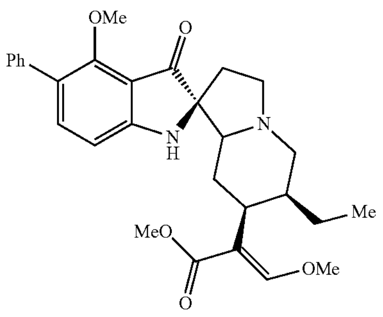
-continued
(VM1516)
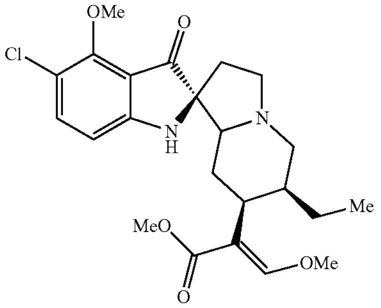
(VM1530)
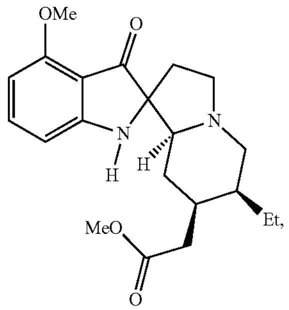
or a pharmaceutically acceptable salt thereof.
In certain embodiments, an exemplary compound of Formula (II) is:
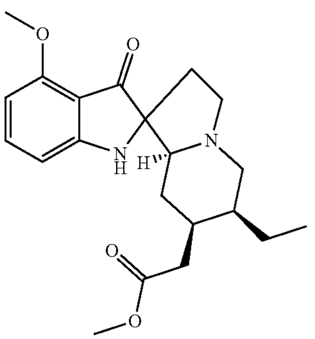
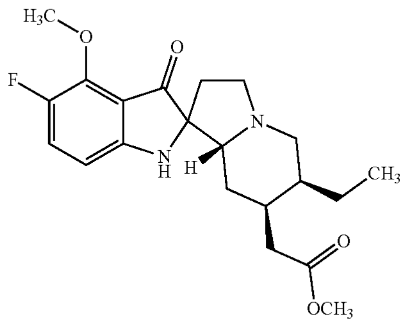

-continued

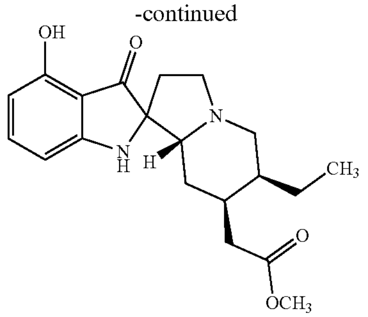

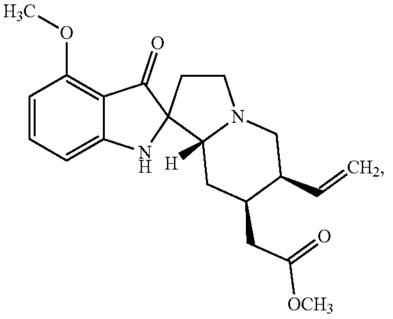

or a pharmaceutically acceptable salt thereof.

Method of Synthesis

The present invention also provides methods of preparing compounds of Formulae (I') and (II'). The present invention also provides methods of preparing compounds of Formulae (I) and (II). The provided methods involve the late-stage introduction of stereocenters and easily accessible initial building blocks.

Figure 4A:
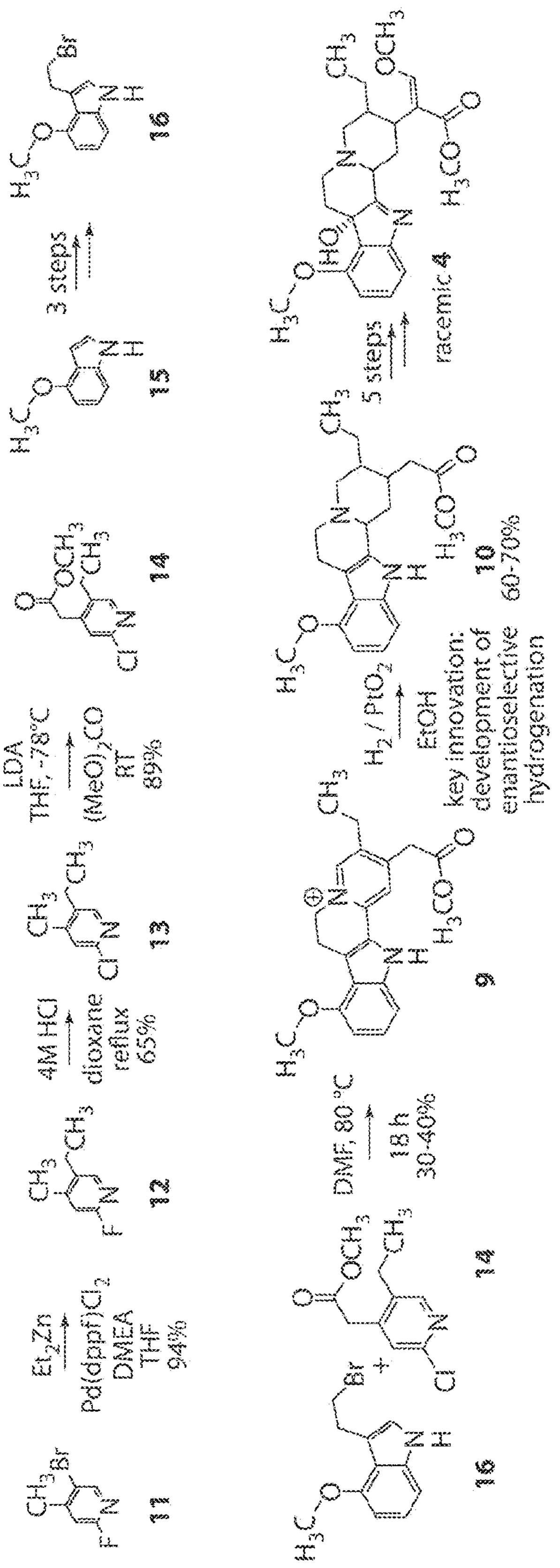
FIG. 4A shows the synthetic scheme to prepare racemic 7-hydroxymitragynine 4.
Figure 4B:
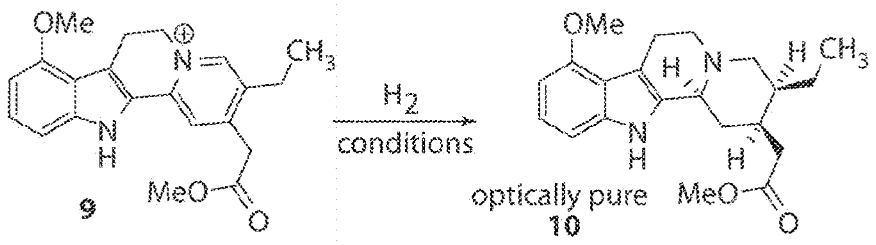
FIG. 4B shows screening of enantioselective hydrogenation conditions to prepare compound 10.
Figure 4C:
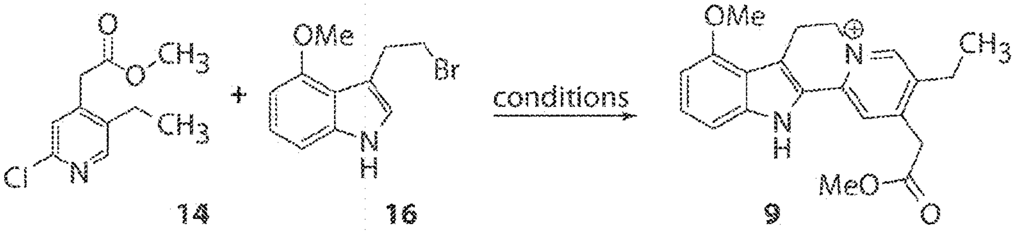
FIG. 4C shows optimization of the condensation reaction to prepare compound 9.

In certain embodiments, racemic synthesis of 7-hydroxymitragynine (4) starts from pyridine and indole building blocks (FIG. 4). Compound 16 was prepared from 15 according to the published procedure (Kuzmin et al. *Eur. J Pharmacol.,* 1998, 358(3), 197-202). Compound 14 was synthesized from 11 in 94% yield. Ethylation of Compound 11 and subsequent fluorine-chlorine halogen exchange yielded Compound 13. Compound 13 was treated with lithium diisopropylamide and dimethylcarbonate to give Compound 14 in 14% yield. Compounds 14 and 16 were then condensed in DMF to yield Compound 9 in 30-40% yield. Racemic form of Compound 4 can then be prepared from Compound 10 according to Takayama's method (Takayama et al., *J. Med. Chem.,* 2002, 45(9), 1949-1956; Takayama et al., *Tetrahedron Lett.,* 1995, 36(51), 9337-9340). Enantioselective hydrogenation of Compound 9 would generate optically pure compound 10. This approach can quickly generate different 3-(2-bromoethyl) derivatives from the commercially available indole and pyridine building blocks. Further, diversification of the pyridine derivatives can be accomplished by cross-coupling with different alkylating agents. Further, this approach provides a route for synthesis of compounds of Formula (II'), e.g. by ring rearrangement under the basic condition. Further, this approach provides a route for synthesis of compounds of Formula (II), e.g. by ring rearrangement under the basic condition.

Figure 5A:
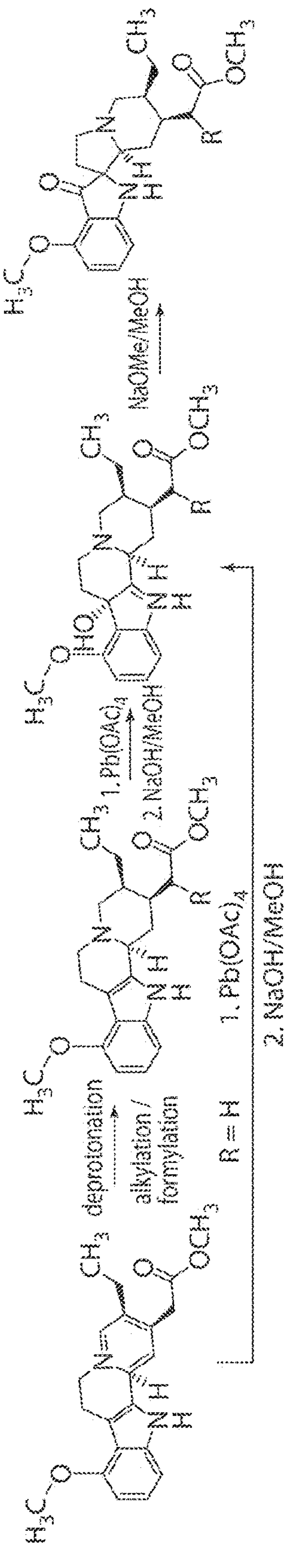
FIG. 5A shows a synthetic scheme for preparing C-16 analogs of mitragynine alkaloids.

In certain embodiments, the compounds of Formula (I') or (II') can be synthesized from Compound 10 (FIG. 5A). In certain embodiments, the compounds of Formula (I) or (II) can be synthesized from Compound 10 (FIG. 5A). Two mitragynine analogs were synthesized with methyl enol ether moiety absent or modified, Compounds 17 (16-desmethoxymethylene-7-hydroxymitragynine, 7ODMG) and 18 (16-desmethoxymethylene mitragynine pseudoindoxyl, DMP) in racemic form (FIG. 2). This approach provides access to diversified C-16 mitragynine analogs.

Figure 5B:
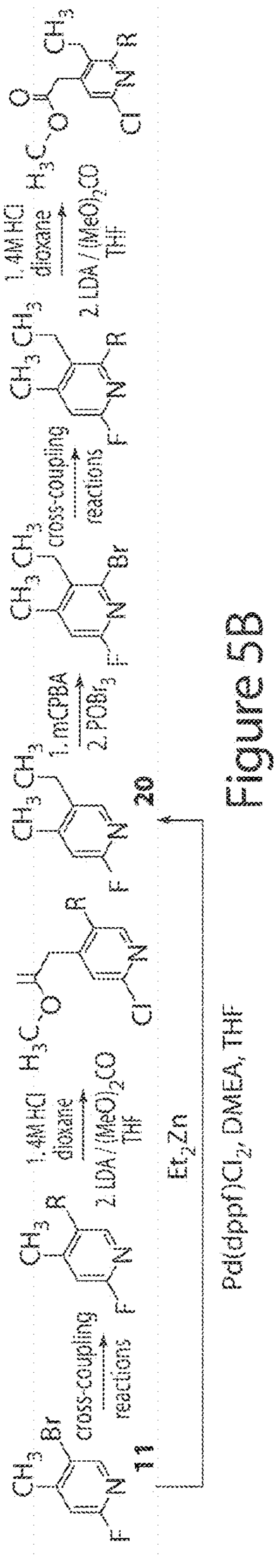
FIG. 5B shows a synthetic scheme for preparing pyridine precursors for the synthesis of C-20 and C-21 analogs of mitragynine alkaloids.

In certain embodiments, the compounds of Formula (I') or (II') can be synthesized from different pyridine building blocks to prepare diversified C-20 and C-21 mitragynine analogs (FIG. 5B). In certain embodiments, the compounds of Formula (I) or (II) can be synthesized from different pyridine building blocks to prepare diversified C-20 and C-21 mitragynine analogs (FIG. 5B).

Figure 5C:
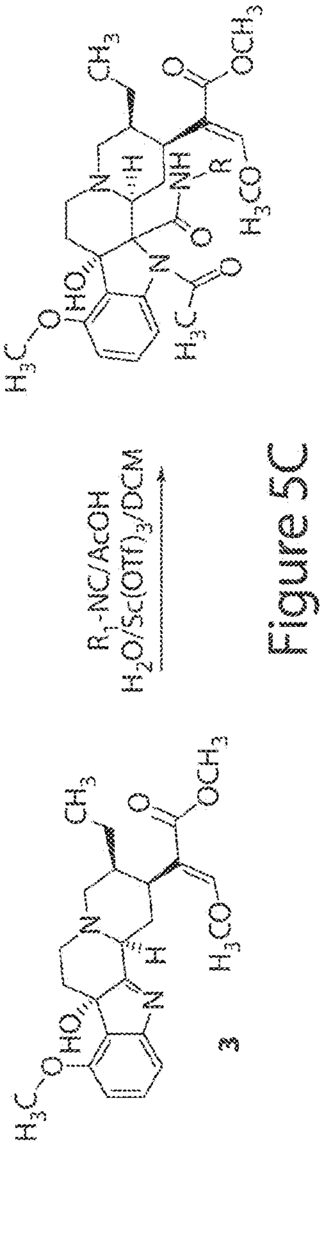
FIG. 5C shows a synthetic scheme for preparing Ugi analogs of mitragynine alkaloids.

In certain embodiments, the compounds of Formula (I') or (II') can be synthesized from Compound 3 by Ugi reactions (FIG. 5C) (Dömling, *Angew. Chem. Int. Ed.,* 2000, 39(18), 3168-3210; Dömling et al., *Chem. Rev.,* 2012, 112(6), 3083-3135). In certain embodiments, the compounds of Formula (I) or (II) can be synthesized from Compound 3 by Ugi reactions (FIG. 5C) (Dömling, *Angew. Chem. Int. Ed.,* 2000, 39(18), 3168-3210; Dömling et al., *Chem. Rev.,* 2012, 112 (6), 3083-3135). This approach provides access to diversified N-1 and C-2 mitragynine analogs.

Figure 5D:
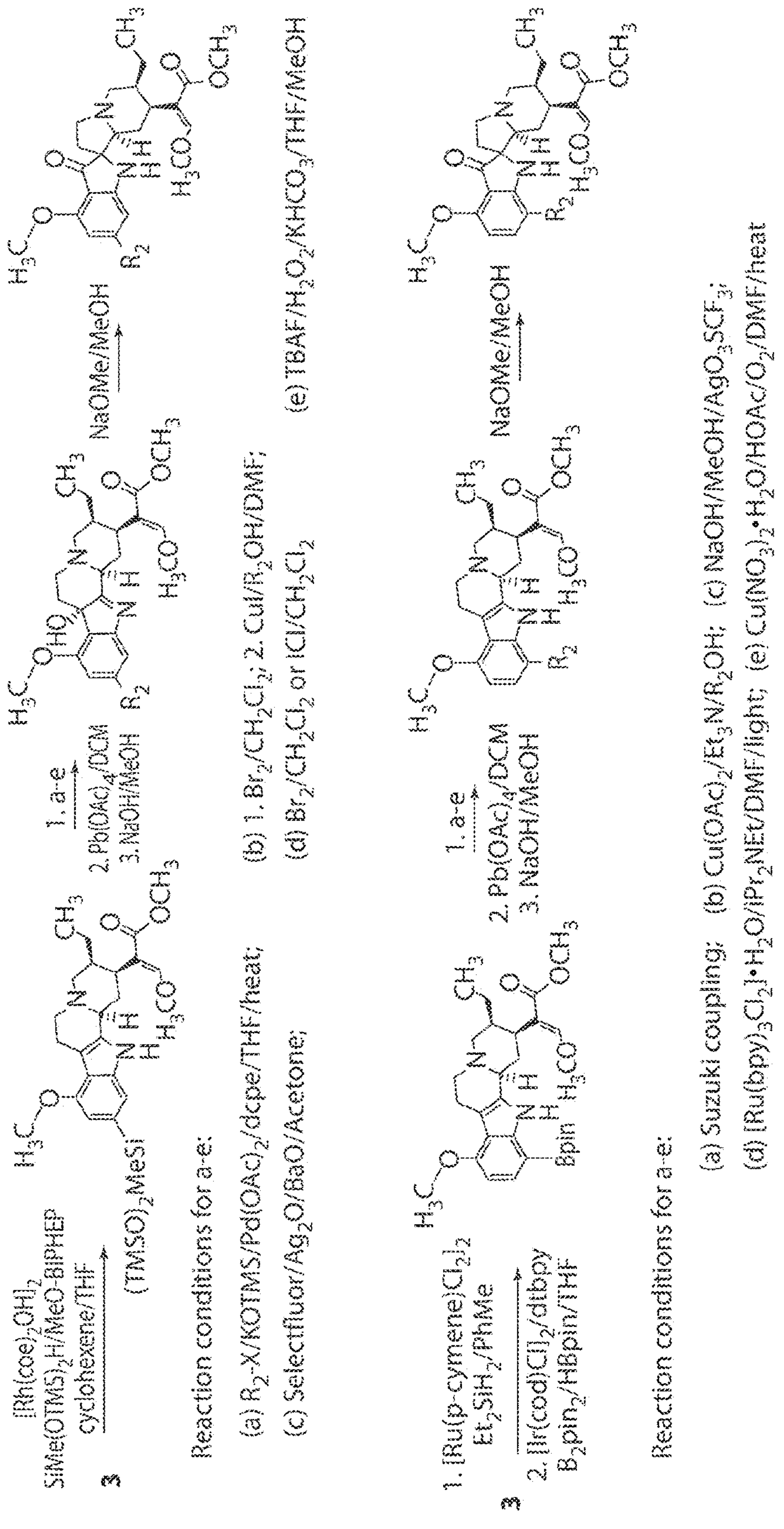
FIG. 5D shows synthetic schemes for preparing C-11 and C-12 analogs of mitragynine alkaloids.

In certain embodiments, the compounds of Formula (I') or (II') can be synthesized from Compound 3 by silylation and borylation reactions from Compound 3 (FIG. 5D) (Cheng et al., Science, 2014, 343(6173), 853-857; Kim et al., *J. Am. Chem. Soc.,* 2012, 134(5), 2528-2531; Zou et al., *Angew. Chem. Int. Ed.,* 2012, 51(3), 784-788). In certain embodiments, the compounds of Formula (I) or (II) can be synthesized from Compound 3 by silylation and borylation reactions from Compound 3 (FIG. 5D) (Cheng et al., *Science,* 2014, 343(6173), 853-857; Kim et al., *J. Am. Chem. Soc.,* 2012, 134(5), 2528-2531; Zou et al., *Angew. Chem. Int. Ed.,* 2012, 51(3), 784-788). This approach provides access to diversified C-11 and C-12 mitragynine analogs.

In certain aspects, the present invention provides a method of preparing a compound of Formula (I) or (II), comprising coupling a compound of Formula (r-1) with a compound of Formula (r-2), as depicted below. In certain aspects, the present invention provides a method of preparing a compound of Formula (I') or (II'), comprising coupling a compound of Formula (r-1) with a compound of Formula (r-2), as depicted below. In certain aspect, the present invention provides a method of preparing a compound of Formula (I) or (II) comprising coupling a compound of Formula (r-1):

(r-1)

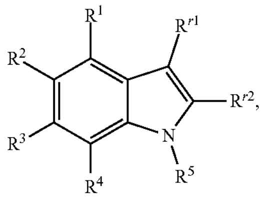

with a compound of Formula (r-2):

(r-2)

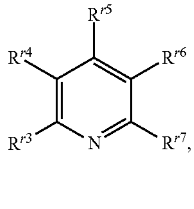

wherein $R^1$, $R^2$, $R^3$, $R^4$, $R^5$ are as defined herein;

each of $R^{r1}$, $R^{r2}$, $R^{r3}$, $R^{r4}$, $R^{r5}$, $R^{r6}$, and $R^{r7}$ is independently selected from the group consisting of hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$SeR^A$, —$C(=O)R^C$, —$C(=O)OR^A$, —$C(=O)N(R^B)_2$, —$OC(=O)R^C$, —$OC(=O)N(R^B)_2$, —$NR^BC(=O)R^C$, —$NR^BC(=O)OR^A$, —$NR^BC(=O)N(R^B)_2$, $S(=O)R^C$, —$SO_2R^C$, —$NR^BSO_2R^C$, and —$SO_2N(R^B)_2$, wherein $R^A$, $R^B$, and $R^C$ are as defined herein. In certain aspect, the present invention provides a method of preparing a compound of Formula (I') or (II') comprising coupling a compound of Formula (r-1) with a compound of Formula (r-2), wherein Formula (r-1), Formula (r-2), $R^1$, $R^2$, $R^3$, $R^4$, $R^5$, $R^{r1}$, $R^{r2}$, $R^{r3}$, $R^{r4}$, $R^{r5}$, $R^{r6}$, and $R^{r7}$ are as defined above. In some embodiments, $R^{r1}$ is hydrogen. In some embodiments, $R^{r1}$ is halogen. In certain embodiments, $R^{r1}$ is F. In certain embodiments, $R^{r1}$ is Cl. In certain embodiments, $R^{r1}$ is Br. In certain embodiments, $R^{r1}$ is I. In certain embodiments, $R^{r1}$ is optionally substituted $C_{1-6}$ alkyl. In certain embodiments, $R^{r1}$ is unsubstituted $C_{1-6}$ alkyl. In certain embodiments, $R^{r1}$ is methyl or ethyl. In certain embodiments, $R^{r1}$ is substituted $C_{1-6}$ alkyl. In certain embodiments, $R^{r1}$ is optionally substituted $C_{1-6}$ haloalkyl. In certain embodiments, $R^{r1}$ is $CH_3CH_2Br$. In certain embodiments, $R^{r1}$ is —$OR^A$, wherein $R^A$ is as generally defined herein. In certain embodiments, $R^{r1}$ is —$OR^A$ and $R^A$ is hydrogen or optionally substituted alkyl. In certain embodiments, $R^{r1}$ is —OH. In certain embodiments, $R^{r1}$ is —$OR^A$ and $R^A$ is optionally substituted $C_{1-6}$ alkyl. In certain embodiments, $R^{r1}$ is —$OR^A$ and $R^A$ is unsubstituted $C_{1-6}$ alkyl. In certain embodiments, $R^{r1}$ is —$OCH_3$ or —$OC_2H_4$.

In some embodiments, $R^2$ is hydrogen. In some embodiments, $R^2$ is halogen. In certain embodiments, $R^2$ is F. In certain embodiments, $R^2$ is Cl. In certain embodiments, $R^2$ is Br. In certain embodiments, $R^2$ is I. In certain embodiments, $R^2$ is optionally substituted $C_{1-6}$ alkyl. In certain embodiments, $R^2$ is unsubstituted $C_{1-6}$ alkyl. In certain embodiments, $R^2$ is methyl or ethyl. In certain embodiments, $R^2$ is substituted $C_{1-6}$ alkyl. In certain embodiments, $R^2$ is optionally substituted $C_{1-6}$ haloalkyl. In certain embodiments, $R^2$ is $CH_2F$, $CHF_2$, $CF_3$, or $CH_3CH_2Br$. In certain embodiments, $R^2$ is —$OR^A$, wherein $R^A$ is as generally defined herein. In certain embodiments, $R^d$ is —$OR^A$ and $R^A$ is hydrogen or optionally substituted alkyl. In certain embodiments, $R^1$ is —OH. In certain embodiments, $R^2$ is —$OR^A$ and $R^A$ is optionally substituted $C_{1-6}$ alkyl. In certain embodiments, $R^2$ is —$OR^A$ and $R^A$ is unsubstituted $C_{1-6}$ alkyl. In certain embodiments, $R^2$ is —$OCH_3$ or —$OC_2H_4$.

In some embodiments, $Rr^3$ is hydrogen. In some embodiments, $Rr^3$ is halogen. In certain embodiments, $Rr^3$ is F. In certain embodiments, $Rr^3$ is Cl. In certain embodiments, $Rr^3$ is Br. In certain embodiments, $Rr^3$ is I. In certain embodiments, $Rr^3$ is optionally substituted $C_{1-6}$ alkyl. In certain embodiments, $Rr^3$ is unsubstituted $C_{1-6}$ alkyl. In certain embodiments, $Rr^3$ is methyl or ethyl. In certain embodiments, $Rr^3$ is substituted $C_{1-6}$ alkyl. In certain embodiments, $Rr^3$ is optionally substituted $C_{1-6}$ haloalkyl. In certain embodiments, $Rr^3$ is $CH_2F$, $CHF_2$, $CF_3$, or $CH_3CH_2Br$. In certain embodiments, $Rr^3$ is —$OR^A$, wherein $R^A$ is as generally defined herein. In certain embodiments, $Rr^3$ is —$OR^A$ and $R^A$ is hydrogen or optionally substituted alkyl. In certain embodiments, $Rr^3$ is —OH. In certain embodiments, $Rr^3$ is —$OR^A$ and $R^A$ is optionally substituted $C_{1-6}$ alkyl. In certain embodiments, $Rr^3$ is —$OR^A$ and $R^A$ is unsubstituted $C_{1-6}$ alkyl. In certain embodiments, $Rr^3$ is —$OCH_3$ or —$OC_2H_4$.

In some embodiments, $R^4$ is hydrogen. In some embodiments, $R^4$ is halogen. In certain embodiments, $R^4$ is F. In certain embodiments, $R^4$ is Cl. In certain embodiments, $R^4$ is Br. In certain embodiments, $R^4$ is I. In certain embodiments, $R^4$ is optionally substituted $C_{1-6}$ alkyl. In certain embodiments, $R^4$ is unsubstituted $C_{1-6}$ alkyl. In certain embodiments, $R^4$ is methyl or ethyl. In certain embodiments, $R^4$ is substituted $C_{1-6}$ alkyl. In certain embodiments, $R^4$ is optionally substituted $C_{1-6}$ haloalkyl. In certain embodiments, $R^4$ is $CH_2F$, $CHF_2$, $CF_3$, or $CH_3CH_2Br$. In certain embodiments, $R^4$ is —$OR^A$, wherein $R^A$ is as generally defined herein. In certain embodiments, $R^d$ is —$OR^A$ and $R^A$ is hydrogen or optionally substituted alkyl. In certain embodiments, $R^4$ is —OH. In certain embodiments, $R^4$ is —$OR^A$ and $R^A$ is optionally substituted $C_{1-6}$ alkyl. In certain embodiments, $R^4$ is —$OR^A$ and $R^A$ is unsubstituted $C_{1-6}$ alkyl. In certain embodiments, $R^4$ is —$OCH_3$ or —$OC_2H_4$.

In some embodiments, $R^{r5}$ is hydrogen. In some embodiments, $R^{r5}$ is halogen. In certain embodiments, $R^{r5}$ is F. In certain embodiments, $R^{r5}$ is Cl. In certain embodiments, $R^{r5}$ is Br. In certain embodiments, $R^{r5}$ is I. In certain embodiments, $R^{r5}$ is optionally substituted $C_{1-6}$ alkyl. In certain embodiments, $R^{r5}$ is unsubstituted $C_{1-6}$ alkyl. In certain embodiments, $R^{r5}$ is methyl or ethyl. In certain embodiments, $R^{r5}$ is substituted $C_{1-6}$ alkyl. In certain embodiments, $R^{r5}$ is optionally substituted $C_{1-6}$ haloalkyl. In certain embodiments, $R^r$ is $CH_2F$, $CHF_2$, $CF_3$, or $CH_3CH_2Br$. In certain embodiments, $R^{r5}$ is —$OR^A$, wherein $R^A$ is as generally defined herein. In certain embodiments, $R^{r5}$ is —$OR^A$ and $R^A$ is hydrogen or optionally substituted alkyl. In certain embodiments, $R^{r5}$ is —OH. In certain embodiments, $R^{r5}$ is —$OR^A$ and $R^A$ is optionally substituted $C_{1-6}$ alkyl. In certain embodiments, $R^{r5}$ is —$OR^A$ and $R^A$ is unsubstituted $C_{1-6}$ alkyl. In certain embodiments, $R^{r5}$ is —$OCH_3$ or —$OC_2H_4$.

In some embodiments, $R^{r6}$ is hydrogen. In some embodiments, $R^{r6}$ is halogen. In certain embodiments, $R^{r6}$ is F. In certain embodiments, $R^{r6}$ is Cl. In certain embodiments, $R^{r6}$ is Br. In certain embodiments, $R^{r6}$ is I. In certain embodiments, $R^{r6}$ is optionally substituted $C_{1-6}$ alkyl. In certain embodiments, $R^{r6}$ is unsubstituted $C_{1-6}$ alkyl. In certain embodiments, $R^{r6}$ is methyl or ethyl. In certain embodiments, $R^{r6}$ is substituted $C_{1-6}$ alkyl. In certain embodiments, $R^{r6}$ is optionally substituted $C_{1-6}$ haloalkyl. In certain embodiments, $R^{r6}$ is $CH_2F$, $CHF_2$, $CF_3$, or $CH_3CH_2Br$. In certain embodiments, $R^{r6}$ is —$OR^A$, wherein $R^A$ is as generally defined herein. In certain embodiments, $R^{r6}$ is —$OR^A$ and $R^A$ is hydrogen or optionally substituted alkyl. In certain embodiments, $R^{r6}$ is —OH. In certain embodiments, $R^{r6}$ is —$OR^A$ and $R^A$ is optionally substituted $C_{1-6}$ alkyl. In certain embodiments, $R^{r6}$ is —$OR^A$ and $R^A$ is unsubstituted $C_{1-6}$ alkyl. In certain embodiments, $R^{r6}$ is —$OCH_3$ or —$OC_2H_4$.

In some embodiments, $R^{r7}$ is hydrogen. In some embodiments, $R^{r7}$ is halogen. In certain embodiments, $R^{r7}$ is F. In certain embodiments, $R^{r7}$ is Cl. In certain embodiments, $R^{r7}$ is Br. In certain embodiments, $R^{r7}$ is I. In certain embodiments, $R^{r7}$ is optionally substituted $C_{1-6}$ alkyl. In certain embodiments, $R^{r7}$ is unsubstituted $C_{1-6}$ alkyl. In certain embodiments, $R^{r7}$ is methyl or ethyl. In certain embodiments, $R^{r7}$ is substituted $C_{1-6}$ alkyl. In certain embodiments, $R^{r7}$ is optionally substituted $C_{1-6}$ haloalkyl. In certain embodiments, $R^{r7}$ is $CH_2F$, $CHF_2$, $CF_3$, or $CH_3CH_2Br$. In certain embodiments, $R^{r7}$ is $—OR^A$, wherein $R^A$ is as generally defined herein. In certain embodiments, $R^{r7}$ is $—OR^A$ and $R^A$ is hydrogen or optionally substituted alkyl. In certain embodiments, $R^{r7}$ is —OH. In certain embodiments, $R^{r7}$ is $—OR^A$ and $R^A$ is optionally substituted $C_{1-6}$ alkyl. In certain embodiments, $R^{r7}$ is $—OR^A$ and $R^A$ is unsubstituted $C_{1-6}$ alkyl. In certain embodiments, $R^{r7}$ is $—OCH_3$ or $—OC_2H_4$.

In certain embodiments, at least one of $R^1$, $R^2$, $R^3$, and $R^4$ is not hydrogen, and $R^{r2}$ is hydrogen. In certain embodiments, one of $R^1$, $R^2$, $R^3$, and $R^4$ is hydrogen, and $R^{r2}$ is hydrogen. In certain embodiments, two of $R^1$, $R^2$, $R^3$, and $R^4$ are hydrogen, and $R^{r2}$ is hydrogen. In certain embodiments, three of $R^1$, $R^2$, $R^3$, and $R^4$ are hydrogen, and $R^{r2}$ is hydrogen. In certain embodiments, $R^2$, $R^3$, and $R^4$ are hydrogen, and $R^{r2}$ is hydrogen. In certain embodiments, $R^1$ is halogen, —CN, $—NO_2$, $—N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, $—OR^A$, $—N(R^B)_2$, $—SR^A$, $—SeR^A$, $—C(=O)R^C$, $—C(=O)OR^A$, $—C(=O)N(R^B)_2$, $—OC(=O)R^C$, $—OC(=O)N(R^B)_2$, $—NR^BC(=O)R^C$, $—NR^BC(=O)OR^A$, $—NR^BC(=O)N(R^B)_2$, $S(=O)R^C$, $—SO_2R^C$, $—NR^BSO_2R^C$, or $—SO_2N(R^B)_2$; and $R^{r2}$ is hydrogen. In certain embodiments, $R^1$ is $—OR^A$; and $R^2$ is hydrogen.

In certain embodiments, $R^{r1}$ is substituted $C_{1-6}$ alkyl; at least one of $R^1$, $R^2$, $R^3$, and $R^4$ is not hydrogen; and $R^{r2}$ is hydrogen. In certain embodiments, $R^{r1}$ is optionally substituted $C_{1-6}$ haloalkyl; $R^1$ is halogen, —CN, $—NO_2$, $—N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, $—OR^A$, $—N(R^B)_2$, $—SR^A$, $—SeR^A$, $—C(=O)R^C$, $—C(=O)OR^A$, $—C(=O)N(R^B)_2$, $—OC(=O)R^C$, $—OC(=O)N(R^B)_2$, $—NR^BC(=O)R^C$, $—NR^BC(=O)OR^A$, $—NR^BC(=O)N(R^B)_2$, $S(=O)R^C$, $—SO_2R^C$, $—NR^BSO_2R^C$, or $—SO_2N(R^B)_2$; and $R^{r2}$ is hydrogen. In certain embodiments, $R^{r1}$ is $CH_3CH_2Br$; $R^1$ is $—OR^A$; and $R^{r2}$ is hydrogen.

In certain embodiments, $R^{r4}$ and $R^{r7}$ are hydrogen. In certain embodiments, $R^{r4}$ and $R^{r7}$ are hydrogen; and $R^{r3}$ is halogen. In certain embodiments, $R^{r4}$ and $R^{r7}$ are hydrogen; and $R^{r3}$ is F. In certain embodiments, $R^{r4}$ and $R^{r7}$ are hydrogen; and $R^{r3}$ is Cl. In certain embodiments, $R^{r4}$ and $R^{r7}$ are hydrogen; and $R^{r3}$ is Br. In certain embodiments, $R^{r4}$ and $R^{r7}$ are hydrogen; and $R^{r3}$ is I.

In certain embodiments, the coupling reaction is carried out at an elevated temperature. In certain embodiments, the coupling reaction is carried out at a temperature from about 30° C. to about 150° C. In certain embodiments, the coupling reaction is carried out at a temperature from about 50° C. to about 120° C. In certain embodiments, the coupling reaction is carried out at a temperature from about 60° C. to about 100° C. In certain embodiments, the coupling reaction is carried out at about 80° C.

A solvent can be used in the coupling reaction. Any solvent not interfering with the reaction can be included. In some embodiments, the solvent is a polar aprotic solvent. Exemplary solvents suitable for the coupling reaction include, but are not limited to, dichloromethane, tetrahydrofuran (THF), ethyl acetate, acetonitrile, dimethylformamide (DMF), dimethyl sulfoxide (DMSO), acetone, and hexamethylphosphoric triamide (HMPT). In certain embodiments, the solvent is DMF.

Pharmaceutical Compositions

The present invention provides pharmaceutical compositions comprising a compound described herein, e.g., a compound of Formulae (I')-(II'), a compound of Formulae (I)-(II), or a pharmaceutically acceptable form thereof, as described herein, and a pharmaceutically acceptable excipient. The present invention also provides pharmaceutical compositions for use in pain treatment. The provided pharmaceutical compositions are also useful for inducing analgesic effect in a subject. The provided pharmaceutical compositions are further useful in treating a neurological disease (e.g. addiction or depression). In addition, the provided pharmaceutical compositions are useful for modulating activities of opioid receptors. In certain embodiments, a provided pharmaceutical composition comprises two or more compounds described herein. In certain embodiments, a provided pharmaceutical composition further comprises a second therapeutic agent. In certain embodiments, a compound described herein, or a pharmaceutically acceptable salt thereof, is provided in an effective amount in the pharmaceutical composition.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner.

Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Also encompassed by the invention are kits (e.g., pharmaceutical packs) to treat or prevent bacterial infections. The kits provided may comprise an inventive pharmaceutical composition or compound and a container (e.g., a vial, ampule, bottle, syringe, and/or dispenser package, or other suitable container). The kits provided may comprise an additional therapeutically active agents include, but are not limited to, antibiotics, anti-viral agents, anesthetics, anticoagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, prostaglandins, etc. In some embodiments, provided kits may optionally further include a second container comprising a pharmaceutical excipient for dilution or suspension of an inventive pharmaceutical composition or compound. In some embodiments, the inventive pharmaceutical composition or compound provided in the container, and the second container are combined to form one unit dosage form.

Method of Use and Treatment

The present invention provides methods for modulating activities of one or more opioid receptors in a subject comprising administering an effective amount of a compound described herein (e.g., a compound of Formulae (I')-(II'), a compound of Formulae (I)-(II)), or a pharmaceutically acceptable salt, solvate, hydrate, polymorph, co-crystal, tautomer, stereoisomer, isotopically labeled derivative, or a prodrug to the subject in need thereof.

In another aspect, the present invention provides methods for modulating activities of one or more opioid receptors in a subject comprising administering an effective amount of a compound described herein (e.g., a compound of Formulae (I')-(II')), or a pharmaceutically acceptable salt thereof), to a biological sample. In another aspect, the present invention provides methods for modulating activities of one or more opioid receptors in a subject comprising administering an effective amount of a compound described herein (e.g., a compound of Formulae (I)-(II)), or a pharmaceutically acceptable salt thereof), to a biological sample.

In some embodiments, the provided compounds exhibit partial or full opioid receptor agonistic activity, i.e., the inventive compounds bind to an opioid receptor, activate the opioid receptor, and increase opioid receptor-mediated activity. In some embodiments, the provided compounds exhibit partial or full opioid receptor antagonistic activity on one or more of MOR, KOR, and DOR. In some embodiments, the provided compounds exhibit partial or full opioid receptor antagonistic activity, i.e. the inventive compounds bind to an opioid receptor, inhibit the opioid receptor, and reduce opioid receptor-mediated activity. In some embodiments, the provided compounds exhibit partial or full opioid receptor antagonistic activity on one or more of MOR, KOR, and DOR. In some embodiments, the provided compounds exhibit dual agonistic and antagonistic effects on one or more of MOR, KOR, and DOR. In some embodiments, the provided compounds exhibit agonistic effect on MOR. In some embodiments, the provided compounds exhibit agonistic effect on KOR. In some embodiments, the provided compounds exhibit agonistic effect on DOR. In some embodiments, the provided compounds exhibit agonistic effect on MOR and antagonistic effect on KOR. In some embodiments, the provided compounds exhibit agonistic effect on MOR and antagonistic effect on DOR. In some embodiments, the provided compounds exhibit agonistic effect on MOR and antagonistic effect on KOR and DOR. In some embodiments, the provided compounds exhibit antagonistic effect on MOR. In some embodiments, the provided compounds exhibit antagonistic effect on KOR. In some embodiments, the provided compounds exhibit antagonistic effect on DOR. In some embodiments, the provided compounds exhibit antagonistic effect on MOR and KOR. In some embodiments, the provided compounds exhibit agonistic antagonistic effect on MOR and DOR. In some embodiments, the provided compounds exhibit antagonistic effect on MOR, KOR, and DOR.

As used herein, the p-opioid receptors (MORs) refer to a class of opioid receptors with high affinity for enkephalins and beta-endorphin but low affinity for dynorphins. The prototypical p receptor agonist is morphine. The term MORs encompass all subtypes generated by alternative splicing (e.g., MOR1, MOR2, and MOR3). In certain embodiments, the MOR protein is encoded by the p-opioid receptor gene, Oprm1 (Gene ID: 4988), which in some embodiments is referred to as Mop, Mor, Lmor, Mor1, Oprm, or M-or-1 (Xu et al., J. Biol. Chem., 2013, 288(29), 21211-21227). The mRNA encoded by Oprm1 can undergo alternative pre-mRNA splicing, which may generate splice variants by 5' and/or 3' alternative splicing. Accordingly, in certain embodiments, the MOR protein is encoded by an Oprm1 splice variant. et al. In certain embodiments, the MOR protein is encoded by an Oprm1 3'-splice variant. In certain embodiments, MOR protein is encoded by an Oprm1 5'-splice variant. In certain embodiments, the MOR protein is encoded by a truncated Oprm1 splice variant. In certain embodiments, the MOR protein is encoded by an Oprm1 splice variant that has been generated by exon skipping or insertion.

Three general classes of MOR proteins include, (1) variants that differ in the intracellular C-terminus but contain all seven transmembrane domains, (2) variants that contain only six transmembrane domains (6-TM) due to the absence of exon 1, and (3) variants that are generated through exon skipping or insertion (Xu et al., *J. Biol. Chem.,* 2013, 288(29), 21211-21227). Accordingly, in certain embodiments, the Oprm1 splice variant contains at least exons 1, 2, and 3, which encodes a MOR protein with all seven transmembrane domains. In certain embodiments, the Oprm1 splice variant lacks at least exon 1, and encodes a MOR protein that lacks the first transmembrane domain (TM1) but contains six transmembrane domains (6-TM). In certain embodiments, the MOR protein is encoded by an Oprm1 6-TM exon-11 associated splice variant (6TM/E11) (Pan, *Gene,* 2002, 295, 97-108; Xu et al., Mol. Biol., 2006, 7, 41; Xu et al., Molecular Pain, 2011, 7, 9). In certain embodiments, the Oprm1 splice variant encodes a MOR protein comprising a single transmembrane domain (TM1) encoded by exon 1. Additional exemplary splice variants are known in the art and have been described previously (see e.g., Pan et al. *Neuroscience,* 2005, 133 (1), 209-220; Eisenberg, Pharmacol. Biochem. Behav., 1994, 47 (4), 943-946; Cadet et al., *J. Immunol.,* 2003, 170 (10), 5118-5123; Xu et al., *J. Biol. Chem.,* 2013, 288(29), 21211-21227; each of which are hereby incorporated by reference). It should be appreciated that the MOR variants, described herein, are merely exemplary and are not meant to be limiting.

As used herein, the κ-opioid receptors (KOR) refer to a class of proteins that in humans are encoded by the Oprk1 gene. KORs bind the opioid peptide dynorphin as the primary endogenous ligand. The term KORs encompass subtypes $KOR_1$, $KOR_2$, and $KOR_3$.

As used herein, the δ-opioid receptors (DOR) refer to a class of proteins that prefer enkephalins as endogenous ligands. The term DORs encompass subtypes $DOR_1$ and $DOR_2$.

In another aspect, the present invention provides methods for treating a painful condition in a subject comprising administering to the subject an effective amount of a compound described herein (e.g., a compound of Formulae (I')-(II')), or a pharmaceutically acceptable salt thereof), or a pharmaceutical composition thereof. In another aspect, the present invention provides methods for treating a painful condition in a subject comprising administering to the subject an effective amount of a compound described herein (e.g., a compound of Formulae (I)-(II)), or a pharmaceutically acceptable salt thereof), or a pharmaceutical composition thereof. In certain embodiments, the present invention provides methods for managing pain in a subject comprising administering to the subject an effective amount of a compound described herein (e.g., a compound of Formulae (I')-(II')), or a pharmaceutically acceptable salt thereof), or a pharmaceutical composition thereof. In certain embodiments, the present invention provides methods for managing pain in a subject comprising administering to the subject an effective amount of a compound described herein (e.g., a compound of Formulae (I)-(II)), or a pharmaceutically acceptable salt thereof), or a pharmaceutical composition thereof.

In another aspect, the present invention provides methods for inducing analgestic effect in a subject comprising administering to the subject an effective amount of a compound described herein (e.g., a compound of Formulae (I')-(II')), or a pharmaceutically acceptable salt thereof), or a pharmaceutical composition thereof. In another aspect, the present invention provides methods for inducing analgestic effect in a subject comprising administering to the subject an effective amount of a compound described herein (e.g., a compound of Formulae (I)-(II)), or a pharmaceutically acceptable salt thereof), or a pharmaceutical composition thereof.

In another aspect, the present invention provides methods for treating a neurological or psychiatric condition disease in a subject comprising administering to the subject an effective amount of a compound described herein (e.g., a compound of Formulae (I')-(II')), or a pharmaceutically acceptable salt thereof), or a pharmaceutical composition thereof. In another aspect, the present invention provides methods for treating a neurological or psychiatric condition disease in a subject comprising administering to the subject an effective amount of a compound described herein (e.g., a compound of Formulae (I)-(II)), or a pharmaceutically acceptable salt thereof), or a pharmaceutical composition thereof.

The term "neurological disease" refers to any disease of the nervous system, including diseases that involve the central nervous system (e.g., brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

In certain embodiments, the neurological disease is depression. The term "depression" includes, but is not limited to, depressive disorders or conditions, such as, for example, major depressive disorders (e.g., unipolar depression), dysthymic disorders (e.g., chronic, mild depression), bipolar disorders (e.g., manic-depression), seasonal affective disorder, and/or depression associated with drug addiction (e.g., withdrawal). The depression can be clinical or subclinical depression. The depression can be associated with one or more opioid receptors.

In certain embodiments, the neurological disease is addiction. In certain embodiments, the neurological disease is drug abuse. In certain embodiments, the neurological disease is an addiction to one or more substances selected from the group consisting of opioids, nicotine, cocaine, psychostimulants, or alcohol.

In another aspect, the present invention provides methods for treating an inflammatory disease in a subject comprising administering to the subject an effective amount of a compound described herein (e.g., a compound of Formulae (I)-(II)), or a pharmaceutically acceptable salt thereof), or a pharmaceutical composition thereof.

The term "inflammatory disease" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

In certain embodiments, the inflammatory disease is diarrhea. In certain embodiments, the inflammatory disease is irritable bowel syndrome.

In certain embodiments, the effective amount is a therapeutically effective amount. In certain embodiments, the effective amount is a therapeutically effective amount. In certain embodiments, the effective amount is an amount effective for treating a painful condition. In certain embodiments, the effective amount is an amount effective for managing pain. In certain embodiments, the effective amount is an amount effective for preventing pain. In certain embodiments, the effective amount is an amount effective for preventing the recurrence of pain In certain embodiments, the effective amount is an amount effective for inducing analgesia in a subject. In certain embodiments, the effective amount is an amount effective for modulating one or more opioid receptors in a subject or a biological sample. In certain embodiments, the effective amount is an amount effective for agonizing one or more opioid receptors in a subject or a biological sample. In certain embodiments, the effective amount is an amount effective for antagonizing one or more opioid receptors in a subject or a biological sample. In certain embodiments, the effective amount is a prophylactically effective amount.

As used herein, the term "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis, or Reiter's arthritis), lumbosacral pain, musculo-skeletal pain, headache, migraine, muscle ache, lower back pain, neck pain, toothache, dental/maxillofacial pain, visceral pain, and the like.

One or more of the painful conditions contemplated herein can comprise mixtures of various types of pain described herein (e.g. nociceptive pain, inflammatory pain, neuropathic pain, etc.). In some embodiments, a particular pain can dominate. In other embodiments, the painful condition comprises two or more types of pain without one dominating. A clinician can determine the dosage to achieve a therapeutically effective amount for a particular subject based on the painful condition.

In certain embodiments, the painful condition is neuropathic pain. The term "neuropathic pain" refers to pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years, even after the original injury has healed. Neuronal injury may occur in the peripheral nerves, dorsal roots, spinal cord or certain regions in the brain. Neuropathic pain conditions include, but are not limited to, diabetic neuropathy (e.g., peripheral diabetic neuropathy); sciatica; non-specific lower back pain; multiple sclerosis pain; carpal tunnel syndrome, fibromyalgia; HIV-related neuropathy; neuralgia (e.g., post-herpetic neuralgia, trigeminal neuralgia); pain resulting from physical trauma (e.g., amputation; surgery, invasive medical procedures, toxins, burns, infection), pain resulting from cancer or chemotherapy (e.g., chemotherapy-induced pain such as chemotherapy-induced peripheral neuropathy), and pain resulting from an inflammatory condition (e.g., a chronic inflammatory condition). Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus, or cortex; or trauma to the brainstem, thalamus, or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

In certain embodiments, the painful condition is non-inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric subjects (e.g., pain where no physical cause may exist), and wandering pain (e.g., wherein the pain repeatedly changes location in the body).

In certain embodiments, the painful condition is inflammatory pain. In certain embodiments, the painful condition (e.g., inflammatory pain) is associated with an inflammatory condition and/or an immune disorder.

In certain embodiments, the pain is acute. In certain embodiments, the pain is chronic.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of the provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound be administered concurrently with, prior to, or subsequent to, one or more additional therapeutically active agents. The provided pharmaceutical composition may comprise a second therapeutically active agents. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In certain embodiments, the additional therapeutically active agent is an analgesic. In certain embodiments, the additional therapeutically active agent is an opioid analgesic. In certain embodiments, the additional therapeutically active agent is a non-opioid (e.g., nonsteroidal anti-inflammatory drug (NSAID) or antidepressant). In certain embodiments, the additional therapeutically active agent is a NSAID. In certain embodiments, the additional therapeutically active agent is an antidepressant. In certain embodiments, the opioid analgesic is one or more agents selected from the group consisting of alfentanil, allylprodine, alphaprodine, anileridine, benzylmorphine, bezitramide, buprenorphine, butorphanol, clonitazene, cyclazocine, desomorphine, dextromoramide, dezocine, diampromide, diamorphone, dihydrocodeine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene fentanyl, heroin, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene, sufentanil, tilidine, tramadol, and pharmaceutical acceptable salts thereof.

Examples

In order that the invention described herein may be more fully understood, the following examples are set forth. It should be understood that these examples are for illustrative purposes only and are not to be construed as limiting this invention in any manner.

Chemical Syntheses

In order that the invention described herein may be more fully understood, the following examples are set forth. It should be understood that these examples are for illustrative purposes only and are not to be construed as limiting this invention in any manner.

List of Abbreviations

DCM dichloromethane

DMSO dimethylsulfoxide

EtOAc ethyl acetate
hr hours
MeOH methanol
mL millilitre
mmol millimole
NMR nuclear magnetic resonance
s singlet
d doublet
m multiplet
t triplet
μL microlitre Preparation and Characterization of the Compounds Described Herein Preparation of the Compounds The compounds provided herein can be prepared from readily available starting materials using methods known in the art, such as the methods described in Mauger et al., *Eur. Pat. Appl.,* 1746097, 24 Jan. 2007, and the methods described in Nitsche et al., *Journal of Medicinal Chemistry,* 56(21), 8389-8403; 2013. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Scheme 1: Preparation of Exemplary Compounds of Formula (I') and Formula (II')

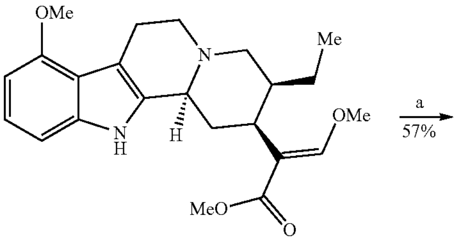

VM1500
mitragynine

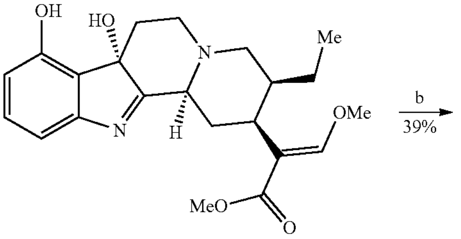

VM1501
7-OH mitragynine

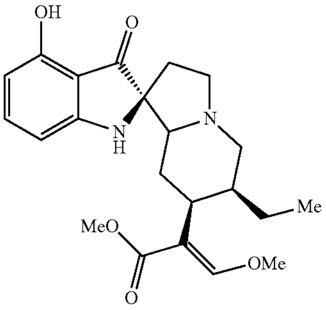

VM1502
mitragynine pseudoindoxyl

-continued

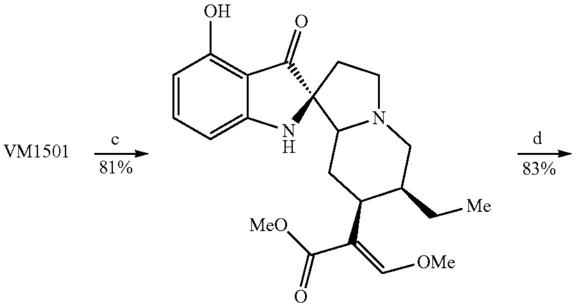

VM1507

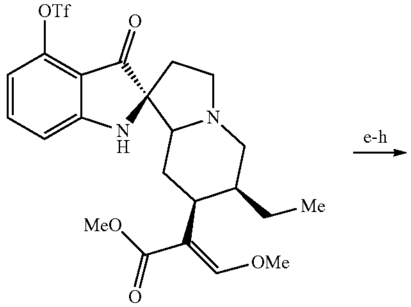

VM1504

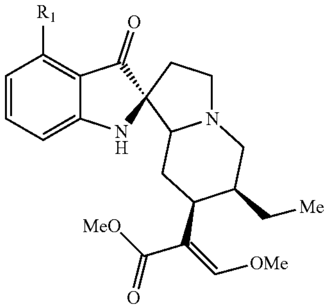

$R_1$
VM1506: -vinyl 81%
VM1508: —H 57%
VM1509: —CN 23%
VM1511: —Ph 38%
VM1512: furan-3-yl 81%

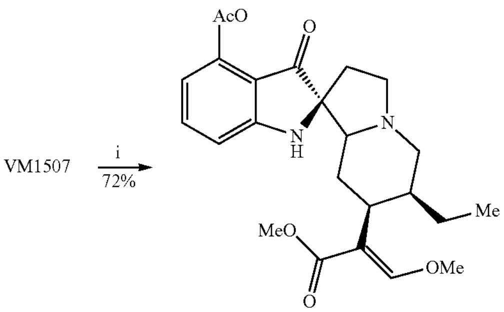

VM1510

-continued
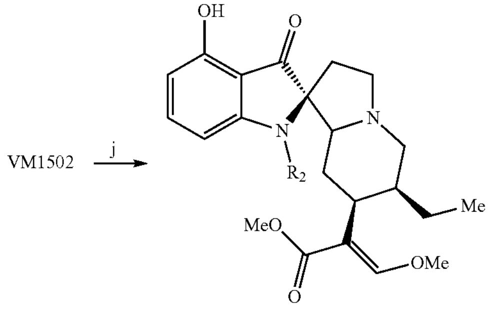
R2
VM1503: —Me 58%
VM1505: -benzyl 81%
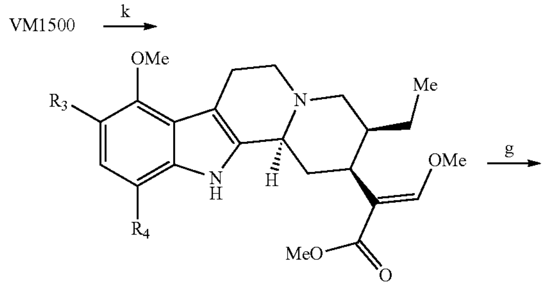
VM1517: R3 = Br, R4 = H 71%
VM1518: R3 = H, R4 = Br 12%
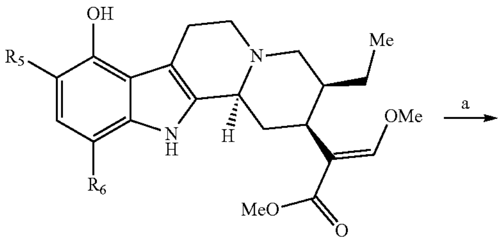
VM1519: R5 = furan-3-yl, R6 = H 57%
VM1520: R5 = H, R6 = furan-3-yl 70%
VM1521: R5 = phenyl, R6 = H 67%
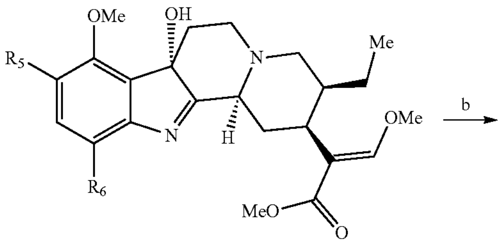
VM1523: R5 = furan-3-yl, R6 = H 15%
VM1524: R5 = H, R6 = furan-3-yl 38%
VM1525: R5 = phenyl, R6 = H 18%
-continued
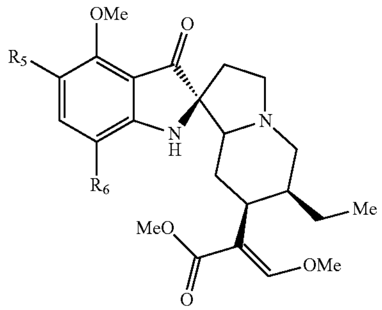
VM1513: R5 = furan-3-yl, R6 = H
VM1514: R5 = H, R6 = furan-3-yl 38%
VM1515: R5 = phenyl,R6 = H
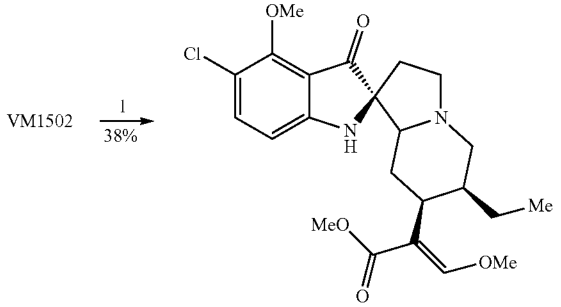
VM1516
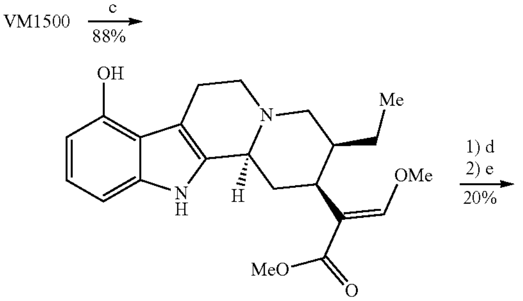
VM1532
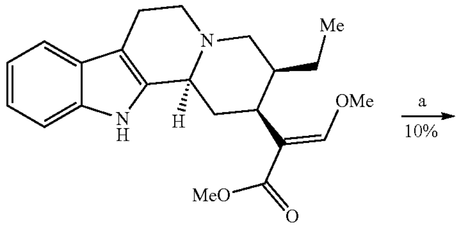
VM1540
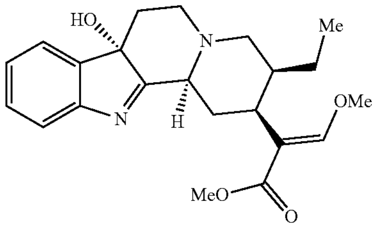
VM1522
VM1500
l -continued

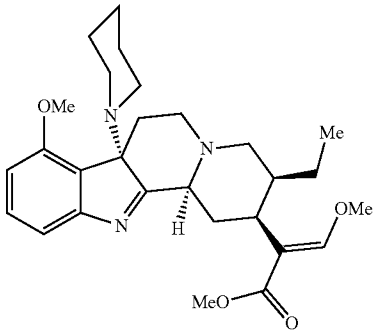

VM1500 m

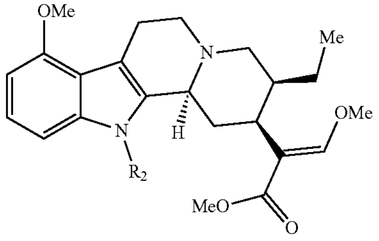

$R_2$
VM1541: —Me
VM1533: -benzyl

VM1500 n

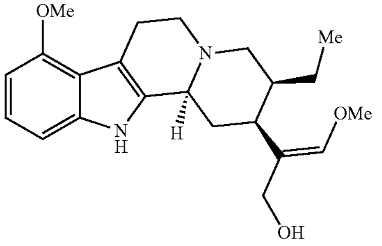

\+

VM1534

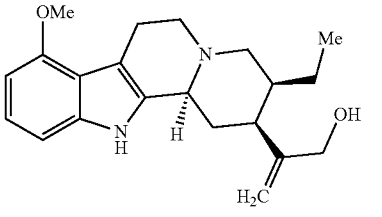

\+

VM1535

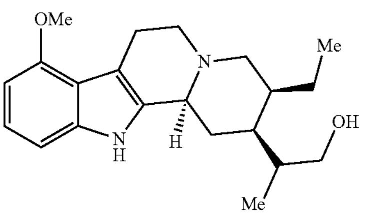

VM1536

VM1500 o 26%

-continued

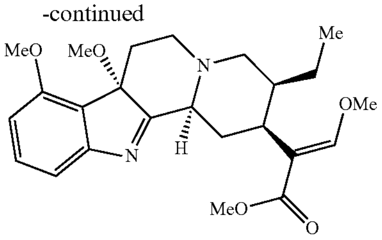

VM1537

VM1500 p 31%

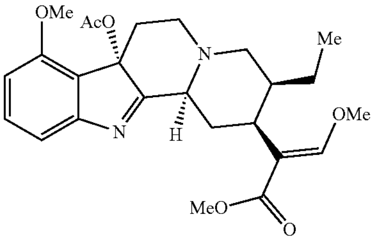

VM1538

VM1500 q

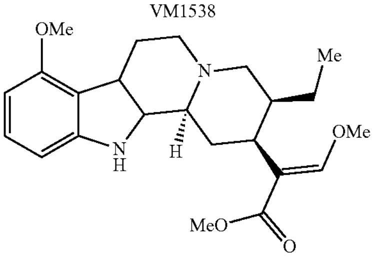

VM1542

Reagents and conditions: (a) PIFA, $H_2O$, acetonitrile, 0° C., 1 h; (b) $Zn(OTf)_2$, toluene, 110° C., 2 h; (c) $AlCl_3$, EtSH, DCM, 0° C., 5 h; (d) $Tf_2O$, pyridine, DCM, −40° C., 1 h; (e, yielding VM1508) $Pd(OAc)_2$, dppp, HCOOH, DMF, 60° C., 1 h; (f, yielding VM1509) $Zn(CN)_2$, $Pd(PPh_3)_4$, DMF, 80° C., 2 h; (g, yielding VM1511 and VM1512) phenylboronic acid (VM1511) or 3-furanylboronic acid (VM1512), $Pd(PPh_3)_4$, $K_2CO_3$, MeOH, toluene, 80° C., 2 h; (h, yielding VM1506) tributylvinyl tin, LiCl, BHT, dioxane, 80° C., 2 h, then TBAF, pyridine, rt, 16 h (i) $Ac_2O$, pyridine, rt, 1 h; (j, yielding VM1503 and VM1505) benzyl bromide (VM1505) or iodomethane (VM1503), NaH, acetonitrile, rt, 2 h; (k) N—Br-succinimide, acetic acid, rt, 4 h; (l) N—Cl-succinimide, acetic acid, rt, 4 h; (m, yielding VM1533 and VM1541) benzyl bromide (VM1533) or iodomethane (VM1541), NaH, DMF, 0° C., 1 h then rt, 3 h; (n, yielding VM1534-VM1536) $LiAlH_4$, diethyl ether, rt, 5 h; (o) PIFA, MeOH, 0° C., 1 h; (p) $Pb(OAc)_4$, DCM, 0° C., 4 h; (q) $H_2$, $PtO_2$, rt.

7,9-dihydroxycorynantheidine

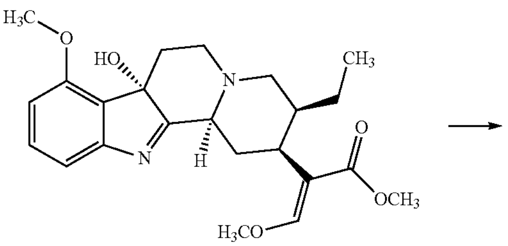

-continued

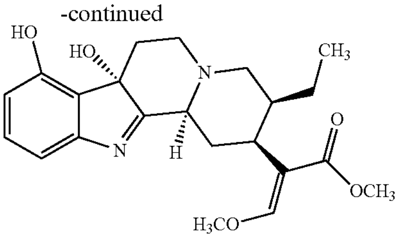

To a stirred solution of 7-OH-mitragynine (2.0 mg, 4.825 μmol) in dry DCM (50 μL) was added followed by $AlCl_3$ (1.93 mg, 14.47 μmol, 3 eq.) and EtSH (7 μL, 94.57 μmol, 19.6 eq.) at 0° C. under argon. The reaction was stirred at room temperature under argon for 5 hr. Removed the solvent under reduced pressure. Purified by basic alumina TLC plate (2% MeOH in DCM). Yield: 0.80 mg, 41.4%.

16-desmethoxymethylene-mitragynine

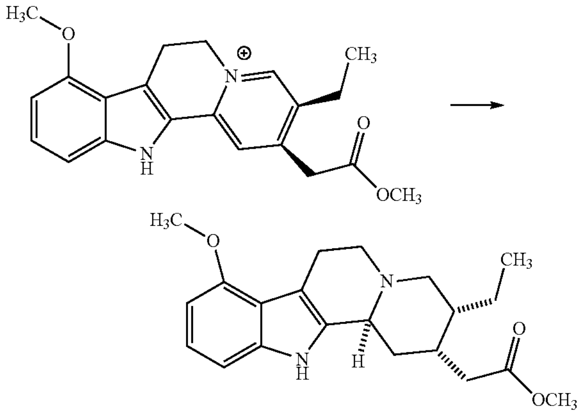

3-ethyl-8-methoxy-2-(2-methoxy-2-oxoethyl)-7,12-dihydro-6H-indolo[2,3-a]quinolizin-5-ium (38 mg, 0.108 mmol) was dissolved in 20 mL EtOH. 10 mg PtO2 was added and stirred under hydrogen atmosphere for 16 hours at rt at atmospheric pressure. The catalyst was filtered and the solvent was evaporated at reduced pressure. Purified using Flash column chromatography using 0-5% MeOH in DCM gradient. The procedure yields the racemic mixture of two enantiomers. Yield: 17 mg, 44%. $^1H$ NMR (600 MHz, $CDCl_3$) δ 7.74 (s, 1H), 7.00 (t, J=7.9 Hz, 1H), 6.89 (d, J=8.1 Hz, 1H), 6.46 (d, J=7.8 Hz, 1H), 3.87 (s, 3H), 3.72 (s, 4H), 3.16-3.05 (m, 2H), 3.03-2.88 (m, 3H), 2.65-2.51 (m, 1H), 2.45-2.32 (m, 2H), 2.32-2.22 (m, 2H), 1.90 (d, J=11.7 Hz, 1H), 1.64 (s, 1H), 1.59-1.43 (m, 2H), 0.96-0.87 (m, 3H).

7-hydroxy-16-desmethoxymethylene Mitragynine

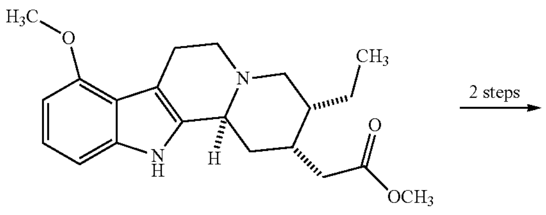

-continued

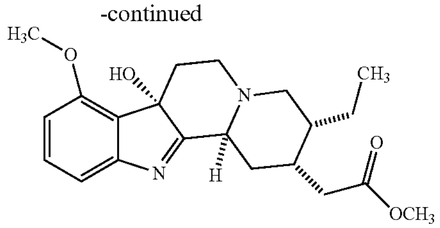

Dissolved racemic 16-desmethoxymethylene-mitragynine (14.9 mg, 0.0418 mmol) in dry DCM (2.2 mL) and cooled to 0° C. Added $Pb(OAc)_4$ (95%, 39.6 mg, 0.0849 mmol, 2.03 eq.) at 0° C. under argon and stirred for 2 hr. The reaction mixture was poured into cold water and extracted with DCM (5 mL×5). The organic layer was washed with brine, dried over $Na_2SO_4$ and concentrated. Purified by Alumina basic TLC plate (50% EtOAc in Hexanes). Collected the major band. 11.0 mg, light yellow amorphous solid (7-acetoxy-16-desmethoxymethylene-mitragynine), 64% yield.

7-Acetoxy-16-desmethoxymethylene-mitragynine (11 mg, 0.0265 mmol) was dissolved in the solution of MeOH (350 μL) and aq. 15% NaOH (50 μL) and stirred at 0° C. for 2 hr. The reaction was poured into cold water (1 mL) and was extracted with DCM (1 mL×5). The organic layer was dried over $Na_2SO_4$, filtered, and concentrated to give light yellow solid. Purified by alumina basic TLC (60% EtOAc in Hexanes). Collecting the major band yielded 4.0 mg, 40% of 7-hydroxy-16-desmethoxymethylene-mitragynine (2 diastereomers).

16-desmethoxymethylene Mitragynine Pseudoindoxyl

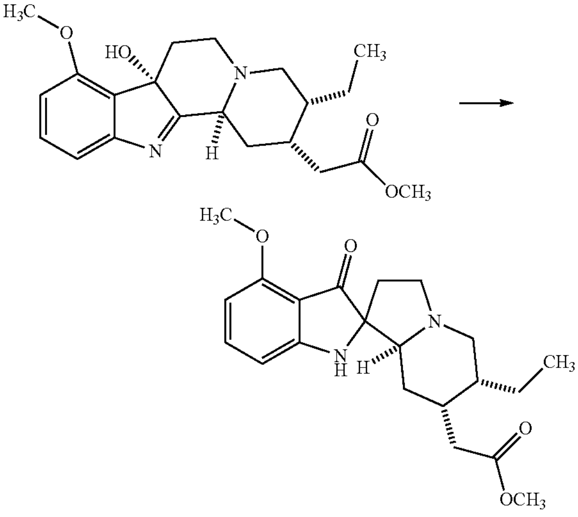

Dissolved 7-hydroxy-16-desmethoxymethylene-mitragynine (4 mg, 0.0107 mmol) and NaOMe (95%, 1.34 mg, 0.0234 mmol, 2.2 eq.) in dry MeOH (0.4 mL) and refluxed overnight. Added water, extracted with DCM and washed with brine. Purified using alumina prep TLC, 2% MeOH in DCM. Yield: 0.64 mg (16%). $^1H$ NMR (600 MHz, $CDCl_3$+MeOD) δ 7.44 (s, 1H), 7.27 (td, J=8.1, 4.0 Hz, 1H), 6.31 (d, J=8.2 Hz, 1H), 6.08-6.02 (m, 1H), 3.80 (s, 3H), 3.26 (dt, J=3.2, 1.6 Hz, 3H), 3.14 (d, J=10.1 Hz, 1H), 3.10-3.05 (m, 1H), 2.40-2.28 (m, 2H), 2.27-2.12 (m, 4H), 2.08 (m, 1H), 2.01 (t, J=12.5 Hz, 1H), 1.98-1.79 (m, 3H), 1.58-1.38 (m, 2H), 1.29-1.12 (m, 3H), 0.85 (t, J=7.2 Hz, 3H).

t-Butyl Ugi Product

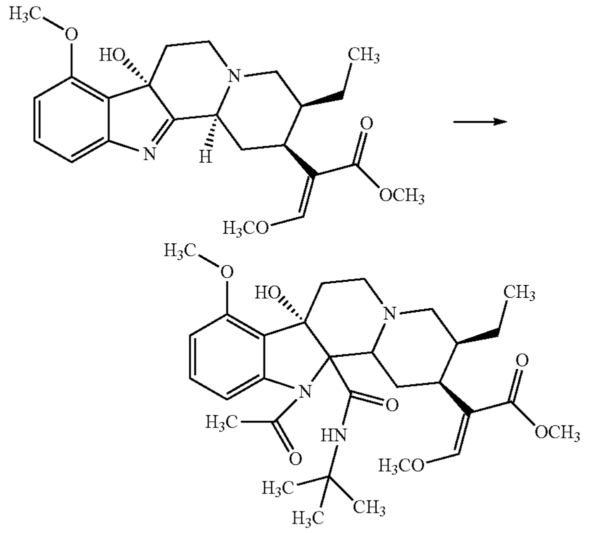

Mitragynine (0.01982 mmol) was added to DCM at 0° C., followed by $Pb(OAc)_4$ (2 eq.), and stirred at 0° C. for 4 h. After 4 hr at 0° C., t-butyl isocyanide (9 μL, 4 eq.), $H_2O$ (11 eq.), acetic acid (1 eq.), and scandium triflate (0.1 eq.) were added, and reaction was stirred at 40° C. overnight. Purified with preparative TLC, basic alumina plate, 3% MeOH in DCM. Yield: (1.6 mg, 15%).

20-desethyl-16-desmethxymethylene Mitragynine

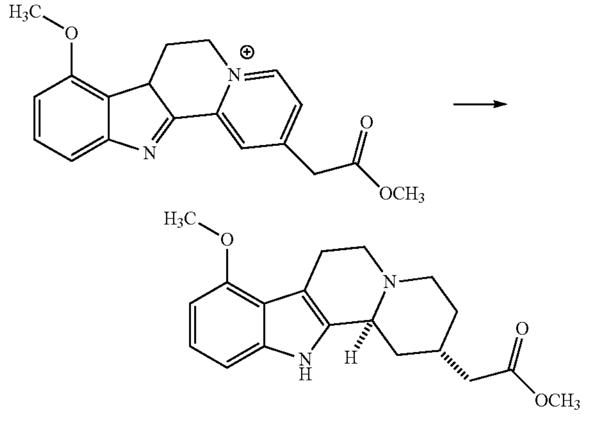

8-methoxy-2-(2-methoxy-2-oxoethyl)-7,7a-dihydro-6H-indolo[2,3-a]quinolizin-5-ium (84 mg, 0.26 mmol) was dissolved in EtOH (20 mL) and 10 mg PtO2 was added. The mixture was stirred under hydrogen atmosphere at atmospheric pressure for 24 h at rt. Solvent was evaporated under reduced pressure and the residue purified using silica gel Flash chromatography (0-5% MeOH in DCM gradient). Yield: 22 mg (26%) racemic product. $^1H$ NMR (600 MHz, $CDCl_3$) δ 7.81 (s, 1H), 7.00 (t, J=7.9 Hz, 1H), 6.90 (d, J=8.1 Hz, 1H), 6.46 (d, J=7.8 Hz, 1H), 3.87 (s, 3H), 3.71 (s, 3H), 3.23 (t, J=15.9 Hz, 1H), 3.20-3.09 (m, 1H), 3.09-2.97 (m, 2H), 2.62-2.54 (m, 1H), 2.41 (ddd, J=27.5, 13.7, 3.8 Hz, 1H), 2.31 (ddd, J=23.2, 15.5, 7.1 Hz, 2H), 2.15 (dd, J=19.2, 8.8 Hz, 1H), 2.07 (dd, J=9.5, 6.0 Hz, 1H), 1.79 (dd, J=12.9, 1.3 Hz, 1H), 1.78 (dt, J=16.2, 8.2 Hz, 1H), 1.59-1.48 (m, 1H), 1.31 (dd, J=23.8, 11.9 Hz, 1H).

Isolation of Mitragynine (1) from *Mitragyna speciosa* (Kratom):

Kratom "Red Indonesian Micro Powder" was purchased from Moon Kratom (Austin, TX.). Mitragynine (1) was extracted from the powdered leaves by a modified method from that reported by Ponglux et al.[16] Kratom powder (450 g) was extracted by refluxing with MeOH (5×500 mL) for 40 min. The suspension was filtered after each extraction and the solvent evaporated. The residue was resuspended in 20% acetic acid solution (2 L) and rinsed with petroleum ether (3×500 mL). The aqueous layer was then cooled on ice bath and basified (pH~9) with 50% aqueous NaOH solution. The basified suspension was extracted with DCM (4×1 L). The combined organic layers were dried over $Na_2SO_4$ and filtered. The solvent was evaporated and the residue purified using flash column chromatography (gradient: 0-50% EtOAc in hexanes). The major constituent was 1 (yield 5.59±0.59 g, 1.24%); smaller quantities of speciogynine and paynantheine were also isolated.

(E)-Methyl-2-((2S,3S,12bS)-3-ethyl-8-methoxy-1,2,3,4,6,7,12,12b-octahydroindolo[2,3-a]quinolizin-2-yl)-3-methoxyacrylate (Mitragynine, VM1500)

IR (NaCl): 3363, 2950, 2796, 1698, 1643, 1570, 1508, 1435, 1310, 1275, 1255, 1148, 1106, 769, 734. $^1H$ NMR (600 MHz, Chloroform-d) δ 7.74 (s, 1H), 7.43 (s, 1H), 6.99 (t, J=7.9 Hz, 1H), 6.90 (d, J=8.0 Hz, 1H), 6.45 (d, J=7.7 Hz, 1H), 3.87 (s, 3H), 3.72 (s, 3H), 3.71 (s, 3H), 3.18-3.08 (m, 2H), 3.06-2.99 (m, 2H), 3.00-2.93 (m, 1H), 2.94-2.90 (m, 1H), 2.57-2.42 (m, 3H), 1.83-1.75 (m, 2H), 1.62 (dt, J=11.5, 3.2 Hz, 1H), 1.24-1.16 (m, 1H), 0.87 (t, J=7.4 Hz, 3H). $^{13}C$ NMR (151 MHz, $CDCl_3$) δ 169.45, 160.75, 154.69, 137.41, 133.90, 121.98, 117.82, 111.67, 108.03, 104.37, 99.91, 61.74, 61.46, 57.94, 55.52, 53.98, 51.57, 40.87, 40.12, 30.14, 24.14, 19.28, 13.07. HRMS calcd for $C_{23}H_{30}N_2O_4$ (MH+), 399.2284. found 399.2285.

(E)-methyl-2-((2S,3S,7aS)-3-ethyl-7a-hydroxy-8-methoxy-1,2,3,4,6,7,7a,12b-octahydroindolo[2,3-a]quinolizin-2-yl)-3-methoxyacrylate (7-OH Mitragynine, VM1501)

Mitragynine (VM1500, 2.00 g, 5.02 mmol) was dissolved in acetonitrile (150 mL), then water (50 mL) was added. The resulting suspension was cooled to 0° C., and the following solution was added slowly over the course of several minutes: PIFA (2.16 g, 1.1 equiv) in 22 mL acetonitrile. The reaction mixture was stirred at 0° C. for 1 hour, then saturated aqueous $NaHCO_3$ solution was added and the mixture extracted with EtOAc. The organic phase was rinsed with brine (60 mL), dried over anhydrous $Na_2SO_4$, and then it was evaporated under reduced pressure. The residue was dissolved in DCM and purified using flash column chromatography (gradient: 0-75% EtOAc in hexanes). The fractions containing the product were evaporated to yield 1075 mg (57%) of 2 as a light brown amorphous powder. IR (NaCl): 3436, 2952, 1702, 1645, 1599, 1487, 1461, 1436, 1270, 1246, 1145, 1078, 795, 738. $^1H$ NMR (600 MHz, Chloroform-d) δ 7.44 (s, 1H), 7.34 (t, J=8.0 Hz, 1H), 7.24 (d, J=7.6 Hz, 1H), 6.78 (d, J=8.3 Hz, 1H), 3.91 (s, 3H), 3.80 (s, 3H), 3.70 (s, 3H), 3.31 (dd, J=11.1, 2.6 Hz, 1H), 3.03 (ddt, J=11.5, 5.5, 2.8 Hz, 2H), 2.84-2.75 (m, 3H), 2.67 (ddd, J=12.3, 4.3, 2.6 Hz, 1H), 2.53-2.46 (m, 1H), 1.98-1.93 (m, 1H), 1.87 (ddd, J=14.6, 12.2, 4.3 Hz, 1H), 1.70-1.54 (m, 3H), 1.26-1.23 (m, 1H), 0.81 (t, J=7.3 Hz, 3H). $^{13}$C NMR (151 MHz, $CDCl_3$) δ 181.25, 169.44, 160.94, 156.02, 154.67, 131.50, 126.24, 114.46, 111.38, 109.65, 69.62, 62.00, 60.73, 58.32, 55.92, 51.54, 50.39, 40.67, 39.32, 36.22, 26.38, 19.10, 13.02. HRMS calcd for $C_{23}H_{30}N_2O_5$ (MH+), 415.2233. found 415.2248.

(E)-methyl 2-((1'S,6'S,7'S)-6'-ethyl-4-methoxy-3-oxo-3',5',6',7',8',8a'-hexahydro-2'H-spiro[indoline-2,1'-indolizine]-7'-yl)-3-methoxyacrylate (Mitragynine Pseudoindoxyl, VM1502)

7-OH-mitragynine (VM1501, 200 mg, 0.48 mmol) was dissolved in dry toluene (6 mL) and $Zn(OTf)_2$ (350 mg, 2 equiv) was added. The reaction was stirred in a sealed tube for 2 hrs at 110° C. To the cooled mixture was added 10 mL sat. aqueous $NaHCO_3$ solution and water (20 mL). Extracted with EtOAc (30 mL). The organic layer was rinsed with brine (20 mL) and dried over anhydrous $Na_2SO_4$. After evaporation of the solvent under reduced pressure, the residue was redissolved in DCM and purified using flash column chromatography (gradient: 1-5% MeOH in DCM) to yield: 78 mg (39%) of VM1502 as a yellow amorphous powder. NMR was identical to that reported in the literature.[17] IR (NaCl): 3350, 2947, 2794, 1687, 1615, 1502, 1343, 1269, 1246, 1148, 1079, 757. $^1$H NMR (600 MHz, Chloroform-d) δ 7.32 (t, J=8.1 Hz, 1H), 7.27 (s, 1H), 6.40 (d, J=8.1 Hz, 1H), 6.13 (d, J=8.1 Hz, 1H), 5.13 (s, 1H), 3.89 (s, 3H), 3.66 (s, 3H), 3.62 (s, 3H), 3.15-3.07 (m, 2H), 2.76 (dt, J=11.9, 3.5 Hz, 1H), 2.38-2.29 (m, 2H), 2.29-2.18 (m, 1H), 2.14 (dt, J=10.2, 6.3 Hz, 1H), 1.93-1.84 (m, 1H), 1.63 (dt, J=11.3, 6.8 Hz, 1H), 1.49 (d, J=11.3 Hz, 1H), 1.18 (ddd, J=13.2, 7.8, 2.9 Hz, 1H), 1.11 (dd, J=11.3, 3.6 Hz, 1H), 0.84 (t, J=7.4 Hz, 3H). $^{13}$C NMR (151 MHz, $CDCl_3$) δ 199.73, 169.05, 162.27, 160.40, 158.74, 138.85, 111.85, 109.96, 103.95, 99.21, 75.37, 73.38, 61.61, 55.86, 54.96, 53.35, 51.36, 40.28, 38.57, 35.25, 23.95, 19.47, 13.11. HRMS calcd for $C_{23}H_{30}N_2O_5$ (MH+), 415.2233. found 415.2216.

(E)-methyl 2-((1'S,6'S,7'S)-6'-ethyl-4-hydroxy-3-oxo-3',5',6',7',8',8a'-hexahydro-2'H-spiro[indoline-2,1'-indolizine]-7'-yl)-3-methoxyacrylate (9-OH Corynantheidine Pseudoindoxyl, VM1507)

7-OH mitragynine (VM1501, 400 mg, 0.97 mmol) was dissolved in dry DCM (20 mL), then $AlCl_3$ (1.29 g, 10 equiv) was added. The mixture was cooled to ° 0 C and ethanethiol (1.39 mL, 20 equiv) was added. The mixture was stirred at rt for 5 hr. Water (30 mL) was slowly added, then it was separated from the organic layer. The organic layer was rinsed with brine (30 mL), then separated and dried over $Na_2SO_4$. Evaporated under reduced pressure. The residue was redissolved in DCM and purified using flash column chromatography (gradient: 1-3% MeOH in DCM) to yield 342 mg (89%) of VM1507 as a bright yellow amorphous powder. IR (NaCl): 3211, 2945, 1697, 1628, 1513, 1451, 1348, 1247, 1148, 1120, 1082, 744. $^1$H NMR (600 MHz, CDCl3) δ 7.29 (m, 2H), 6.30 (d, J=8.1 Hz, 1H), 6.15 (d, J=8.0 Hz, 1H), 5.12 (s, 1H), 3.67 (s, 3H), 3.63 (s, 3H), 3.17-3.11 (m, 2H), 2.83-2.75 (m, 1H), 2.36-2.29 (m, 2H), 2.26-2.20 (m, 2H), 2.14 (dd, J=11.2, 2.8 Hz, 1H), 1.98-1.90 (m, 1H), 1.69-1.57 (m, 2H), 1.51 (d, J=11.2 Hz, 1H), 1.24-1.16 (m, 1H), 1.14-1.08 (m, 1H), 0.86 (t, J=7.4 Hz, 3H). $^{13}$C NMR (151 MHz, $CDCl_3$) δ 203.60, 169.03, 160.52, 160.05, 157.31, 140.24, 111.63, 108.97, 103.68, 102.27, 75.49, 72.99, 61.69, 54.93, 53.32, 51.41, 40.21, 38.63, 34.79, 23.97, 19.43, 13.07. HRMS calcd for $C_{22}H_{28}N_2O_5$ (MH+), 401.2076. found 401.2068.

(E)-methyl 2-((1'S,6'S,7'S)-6'-ethyl-3-oxo-4-(trifluoromethylsulfonyloxy)-3',5',6',7',8',8a'-hexahydro-2'H-spiro[indoline-2,1'-indolizine]-7'-yl)-3-methoxyacrylate (9-O-trifluoromethanesulfonyl Corynantheidine Pseudoindoxyl, VM1504)

VM1507 (200 mg, 0.5 mmol) was dissolved in dry DCM (15 mL) and pyridine (647 uL, 16 equiv) was added. Then the solution was cooled to −40° C. on a dry ice acetone bath, and the following solution was slowly added over 2-3 minutes: 5 mL DCM and triflic anhydride (340 uL, 4 equiv). The reaction was stirred for 1 h at −40° C. After warming up to rt, the solution was purified using flash column chromatography without immediately (gradient: 20-75% EtOAc in hexanes) to yield 233 mg (83%) of VM1504 as a brown amorphous solid. $^1$H NMR (600 MHz, $CDCl_3$) δ 7.41 (t, J=8.1 Hz, 1H), 7.29 (s, 1H), 6.84 (d, J=8.3 Hz, 1H), 6.52 (d, J=7.9 Hz, 1H), 5.58 (s, 1H), 3.68 (s, 3H), 3.63 (s, 3H), 3.15 (d, J=9.7 Hz, 2H), 2.80 (dd, J=12.5, 3.5 Hz, 1H), 2.35 (d, J=7.4 Hz, 2H), 2.27 (d, J=8.8 Hz, 2H), 2.18-2.13 (m, 1H), 1.66-1.58 (m, 1H), 1.52 (d, J=10.9 Hz, 1H), 1.22-1.16 (m, 2H), 0.85 (t, J=7.3 Hz, 4H). $^{13}$C NMR (151 MHz, $CDCl_3$) δ 198.15, 171.40, 168.92, 161.46, 160.55, 145.34, 138.13, 111.73, 110.01, 73.58, 61.69, 60.62, 54.84, 53.65, 53.33, 51.38, 40.14, 38.33, 35.12, 23.84, 21.28, 19.41, 14.41, 13.00. HRMS calcd for $C_{23}H_{27}F_3N_2O_7S$ (MH+), 533.1569. found 533.1547.

(E)-methyl 2-((1'S,6'S,7'S)-6'-ethyl-3-oxo-3',5',6',7',8',8a'-hexahydro-2'H-spiro[indoline-2,1'-indolizine]-7'-yl)-3-methoxyacrylate (Corynantheidine Pseudoindoxyl, VM1508)

VM1504 (10 mg, 0.019 mmol) was dissolved in dry DMF (500 uL) in a sealed tube and the following reagents were added: $Pd(OAc)_2$ (1.4 mg, 0.3 equiv), dppp (4 mg, 0.5 equiv), triethylamine (52.4 uL, 20 equiv) and formic acid (1 uL, 1.8 equiv). The mixture was stirred at 60° C. for 1 h. The reaction mixture was diluted with EtOAc (10 mL) and washed with brine (5 mL) 5 times. The organic layer was dried over $Na_2SO_4$ and evaporated under reduced pressure. The residue was redissolved in DCM and purified using preparative TLC (75% EtOAc in hexanes) to yield 4 mg (57%) of VM1508 as an amorphous solid. IR (NaCl): 3286, 2927, 2360, 1676, 1620, 1437, 1248, 1200, 1138, 755. $^1$H NMR (600 MHz, $CDCl_3$) δ 7.55 (d, J=7.7 Hz, 1H), 7.43-7.38 (m, 1H), 7.27 (d, J=6.7 Hz, 1H), 6.85 (d, J=8.3 Hz, 1H), 6.77-6.72 (m, 1H), 5.20 (s, 1H), 3.66 (s, 3H), 3.62 (s, 3H), 3.20-3.12 (m, 2H), 2.82-2.76 (m, 1H), 2.38-2.29 (m, 2H), 2.25 (s, 2H), 2.20-2.13 (m, 1H), 1.97-1.89 (m, 1H), 1.69-1.61 (m, 1H), 1.55-1.48 (m, 1H), 1.23-1.17 (m, 1H), 1.05 (s, 1H), 0.86 (t, J=7.4 Hz, 3H). $^{13}$C NMR (151 MHz, CDCl3) δ 202.60, 169.02, 160.95, 160.51, 137.30, 124.61, 118.30, 111.85, 111.68, 75.22, 73.52, 61.67, 54.94, 53.42, 51.40, 40.20, 38.59, 35.13, 23.92, 21.29, 19.41, 13.06. HRMS calcd for $C_{22}H_{28}N_2O_4$ (MH+), 385.2127. found 385.2120.

(E)-methyl 2-((1'S,6'S,7'S)-4-cyano-6'-ethyl-3-oxo-3',5',6',7',8',8a'-hexahydro-2'H-spiro[indoline-2,1'-indolizine]-7'-yl)-3-methoxyacrylate (9-cyano corynantheidine pseudoindoxyl, VM1509)

VM1504 (20 mg, 0.038 mmol) was dissolved in dry DMF (500 uL) in a sealed tube, $Pd(PPh_3)_4$ (4.3 mg, 0.1 equiv) and $Zn(CN)_2$ (8.8 mg, 2 equiv) were added. The reaction mixture was stirred at 80° C. for 3 h. After 3 h, the reaction was diluted with EtOAc (20 mL) and washed with brine 5 times. The organic layer was dried over $Na_2SO_4$ and evaporated under reduced pressure. The residue was redissolved in DCM and purified using flash column chromatography (gradient: 20-80% EtOAC in hexanes) to yield 10 mg (65%) of VM1509 as an amorphous brown solid. IR (NaCl): 3355, 2940, 2233, 1699, 1606, 1501, 1438, 1242, 993, 859, 1082, 776. $^1$H NMR (600 MHz, $CDCl_3$) δ 7.47-7.43 (m, 1H), 7.28 (s, 1H), 7.07 (d, J=8.4 Hz, 1H), 7.05 (d, J=7.2 Hz, 1H), 5.43 (s, 1H), 3.68 (s, 3H), 3.62 (s, 3H), 3.15 (t, J=10.1 Hz, 2H), 2.79 (dt, J=12.8, 3.5 Hz, 1H), 2.40-2.33 (m, 2H), 2.31-2.27 (m, 1H), 2.23 (t, J=12.1 Hz, 1H), 2.19-2.13 (m, 1H), 1.96-1.90 (m, 1H), 1.66-1.59 (m, 1H), 1.51 (d, J=11.2 Hz, 1H), 1.23-1.16 (m, 1H), 1.07 (d, J=12.7 Hz, 1H), 0.85 (t, J=7.4 Hz, 3H). $^{13}$C NMR (151 MHz, $CDCl_3$) δ 201.47, 169.06, 162.01, 160.51, 142.35, 137.85, 136.72, 129.43, 128.16, 127.88, 120.06, 111.79, 110.73, 75.10, 73.89, 61.70, 55.07, 53.59, 51.40, 40.28, 38.57, 36.87, 36.86, 35.53, 24.92, 24.08, 19.48, 13.08. HRMS calcd for $C_{23}H_{27}N_3O_4$ (MH+), 410.2080. found 410.2068.

(E)-methyl 2-((1'S,6'S,7'S)-6'-ethyl-3-oxo-4-phenyl-3',5',6',7',8',8a'-hexahydro-2'H-spiro[indoline-2,1'-indolizine]-7'-yl)-3-methoxyacrylate (9-phenyl Corynantheidine Pseudoindoxyl, VM1511)

VM1504 (75 mg, 0.14 mmol) was dissolved in dry toluene (0.5 mL) and the solvent was removed under reduced pressure to ensure azeotropic removal of water residues. Dry methanol (1 mL) and dry toluene (1.5 mL) were added. To the resulting solution were added phenylboronic acid (19 mg, 1.1 equiv), $K_2CO_3$ (38.9 mg, 2 equiv) and $Pd(PPh_3)_4$ (8.1 mg, 0.05 equiv). The mixture was stirred at 80° C. for 2 hrs. The solvent was evaporated under reduced pressure and the residue suspended in DCM, rinsed with water and brine (20 mL), then the organic layer was dried over $Na_2SO_4$ and was evaporated. Purified using flash column chromatography (gradient: 20-50% EtOAc in hexanes) to yield: 21 mg (32%) of VM1511 as a yellow amorphous solid. IR (NaCl): 3364, 2936, 2360, 1698, 1600, 1483, 1436, 1233, 1150, 759. $^1$H NMR (600 MHz, $CDCl_3$) δ 7.52-7.49 (m, 2H), 7.43-7.34 (m, 4H), 7.30 (s, 1H), 6.82 (d, J=8.2 Hz, 1H), 6.68 (d, J=7.3 Hz, 1H), 5.26 (s, 1H), 3.69 (s, 3H), 3.63 (s, 3H), 3.15 (d, J=10.0 Hz, 2H), 2.79 (dt, J=13.0, 3.3 Hz, 1H), 2.34-2.25 (m, 3H), 2.21 (s, 1H), 2.17-2.10 (m, 1H), 1.95-1.88 (m, 1H), 1.69-1.63 (m, 1H), 1.53-1.47 (m, 1H), 1.24-1.18 (m, 1H), 1.14-1.09 (m, 1H), 0.86 (t, J=7.4 Hz, 3H). $^{13}$C NMR (151 MHz, CDCl3) δ 201.47, 169.06, 162.01, 160.51, 142.35, 137.85, 136.72, 129.43, 128.16, 127.88, 120.06, 111.79, 110.73, 75.10, 73.89, 61.70, 55.07, 53.59, 51.40, 40.28, 38.57, 36.87, 36.86, 35.53, 24.92, 24.08, 19.48, 13.08. HRMS calcd for $C_{28}H_{32}N_2O_4$ (MH+), 461.2440. found 461.2422.

(E)-methyl 2-((1'S,6'S,7'S)-6'-ethyl-4-(furan-3-yl)-3-oxo-3',5',6',7',8',8a'-hexahydro-2'H-spiro[indoline-2,1'-indolizine]-7'-yl)-3-methoxyacrylate (9-furyl Corynantheidine Pseudoindoxyl, VM1512)

The procedure described for the synthesis of VM1511 was used. Instead of phenylboronic acid, (furan-3-yl)boronic acid was employed. Yield: 81%. Compound VM1512 is a bright yellow amorphous powder. IR (NaCl): 3358, 2954, 2795, 2360, 2341, 1691, 1604, 1437, 1316, 1238, 1152, 796, 772. $^1$H NMR (600 MHz, Chloroform-d) δ 8.49 (d, J=1.4 Hz, 1H), 7.48 (d, J=1.7 Hz, 1H), 7.40 (t, J=7.8 Hz, 1H), 7.31 (s, 1H), 6.87 (d, J=7.5 Hz, 1H), 6.84 (dd, J=1.9, 0.9 Hz, 1H), 6.77 (d, J=8.1 Hz, 1H), 5.22 (s, 1H), 3.70 (s, 3H), 3.65 (s, 3H), 3.22-3.14 (m, 2H), 2.81 (dt, J=12.6, 3.7 Hz, 1H), 2.40-2.32 (m, 2H), 2.32-2.22 (m, 2H), 2.17 (dd, J=11.5, 3.2 Hz, 1H), 2.00-1.92 (m, 1H), 1.75-1.65 (m, 1H), 1.57-1.51 (m, 1H), 1.23 (dtd, J=15.1, 7.4, 2.7 Hz, 1H), 1.15-1.10 (m, 1H), 0.89 (t, J=7.4 Hz, 3H). $^{13}$C NMR (151 MHz, $CDCl_3$) δ 201.73, 169.03, 162.40, 160.45, 143.85, 142.48, 137.00, 132.42, 122.74, 118.06, 116.66, 111.77, 110.60, 110.18, 75.11, 74.00, 61.65, 55.07, 53.54, 51.38, 40.28, 38.61, 35.68, 24.01, 19.50, 13.11. HRMS calcd for $C_{26}H_{30}N_2O_5$ (MH+), 451.2433. found 451.2215.

(E)-methyl 2-((1'S,6'S,7'S)-4-acetoxy-6'-ethyl-3-oxo-3',5',6',7',8',8a'-hexahydro-2'H-spiro[indoline-2,1'-indolizine]-7'-yl)-3-methoxyacrylate (9-O-acetyl Corynantheidine Pseudoindoxyl, VM1510)

VM1507 (20 mg, 0.05 mmol) was dissolved in pyridine (0.5 mL) and acetic anhydride (80 uL) was added. The mixture was stirred at rt for 2 h. The solution was poured into sat. aqueous $NaHCO_3$ solution and extracted with DCM (30 mL). The organic layer was separated, rinsed with brine (10 mL), dried over $Na_2SO_4$ and evaporated under reduced pressure the residue was redissolved in DCM and purified using flash column chromatography (gradient: 0-5% MeOH in DCM) to yield 13 mg (59%) of VM1510 as a bright yellow amorphous solid. IR (NaCl): 3393, 2956, 2874, 2787, 1761, 1688, 1628, 1503, 1239, 1217, 910, 764. $^1$H NMR (500 MHz, Chloroform-d) δ 7.38 (t, J=8.0 Hz, 1H), 7.28 (s, 1H), 6.71 (d, J=8.2 Hz, 1H), 6.36 (d, J=7.6 Hz, 1H), 5.73 (s, 1H), 3.68 (s, 3H), 3.62 (s, 3H), 3.20 (dd, J=8.6, 3.0 Hz, 2H), 2.79 (dd, J=12.6, 3.9 Hz, 1H), 2.36 (s, 3H), 2.33-2.22 (m, 3H), 2.22-2.14 (m, 1H), 1.95 (dt, J=15.8, 6.3 Hz, 1H), 1.63 (dt, J=13.0, 6.1 Hz, 1H), 1.53 (d, J=11.6 Hz, 1H), 1.30-1.16 (m, 2H), 1.16-1.09 (m, 1H), 0.86 (t, J=7.3 Hz, 3H). $^{13}$C NMR (151 MHz, $CDCl_3$) δ 199.57, 169.14, 168.98, 161.57, 160.47, 148.07, 138.28, 113.07, 111.70, 110.70, 109.35, 75.71, 73.70, 61.67, 55.02, 53.49, 51.38, 40.25, 38.51, 35.16, 23.91, 21.01, 19.49, 13.08. HRMS calcd for $C_{24}H_{30}N_2O_6$ (MH+), 443.2182. found 443.2174.

(E)-methyl 2-((1'S,6'S,7'S)-1-benzyl-6'-ethyl-4-methoxy-3-oxo-3',5',6',7',8',8a'-hexahydro-2'H-spiro[indoline-2,1'-indolizine]-7'-yl)-3-methoxyacrylate (N-benzyl Mitragynine Pseudoindoxyl, VM1505)

Compound VM1502 was dissolved in dry acetonitrile (0.5 mL) and NaH (6 mg, 10 equiv) was added. The resulting suspension was stirred at rt for 30 minutes, during which its color turned red. Benzyl bromide (7.2 uL, 2.5 equiv) was added and the mixture stirred for 2 h at rt. The red color disappeared promptly after the addition of benzyl bromide. After the reaction time, the mixture was carefully poured into cold water (20 mL) and extracted with DCM (30 mL). The organic layer was rinsed with brine (5 mL) separated, dried over $Na_2SO_4$ and evaporated under reduced pressure. The residue was redissolved in DCM and purified using flash column chromatography (gradient: 0-5% MeOH in DCM) to yield: 7.8 mg (64%) of VM1505 as a bright yellow amorphous solid. IR (NaCl): 2940, 2794, 1694, 1610, 1497, 1337, 1265, 1239, 1078, 732. $^1$H NMR (500 MHz, Chloroform-d) δ 7.42-7.28 (multiple overlapping peaks, 5H), 7.25-7.17 (multiple overlapping peaks, 2H), 6.08 (d, J=8.1 Hz, 1H), 6.04 (d, J=8.3 Hz, 1H), 5.35 (d, J=17.4 Hz, 1H), 4.73 (d, J=17.3 Hz, 1H), 3.90 (s, 3H), 3.70 (s, 3H), 3.64 (s, 3H), 3.13 (dd, J=11.1, 2.2 Hz, 1H), 3.02 (t, J=8.1 Hz, 1H), 2.78-2.72 (m, 1H), 2.33-2.18 (m, 4H), 2.09-2.02 (m, 1H), 1.94 (dt, J=13.7, 8.5 Hz, 1H), 1.66 (dt, J=19.2, 6.8 Hz, 1H), 1.50 (d, J=10.9 Hz, 1H), 1.13 (d, J=11.8 Hz, 1H), 0.86 (t, J=7.4 Hz, 3H). $^{13}$C NMR (151 MHz, $CDCl_3$) δ 199.55, 169.06, 161.60, 160.40, 158.81, 138.88, 138.82, 129.25, 129.02, 128.76, 128.64, 126.95, 126.51, 111.99, 108.49, 101.82, 98.07, 61.63, 55.89, 55.23, 53.92, 51.38, 47.61, 40.46, 38.67, 33.80, 32.06, 24.18, 19.82, 13.13. HRMS calcd for $C_{30}H_{36}N_2O_5$ (MH+), 505.2702. found 505.2726.

(E)-methyl 2-((1'S,6'S,7'S)-6'-ethyl-4-methoxy-1-methyl-3-oxo-3',5',6',7',8',8a'-hexahydro-2'H-spiro[indoline-2,1'-indolizine]-7'-yl)-3-methoxyacrylate (N-methyl Mitragynine Pseudoindoxyl, VM1503)

The procedure described for the synthesis of VM1505 was used. Instead of benzyl bromide, iodomethane was employed. Yield: 58%. Compound VM1503 is a bright yellow amorphous powder. IR (NaCl): 2947, 2778, 2361, 1687, 1611, 1500, 1337, 1273. $^1$H NMR (600 MHz, Chloroform-d) δ 7.34 (t, J=8.1 Hz, 1H), 7.28 (s, 1H), 6.25 (d, J=8.2 Hz, 1H), 6.05 (d, J=8.0 Hz, 1H), 3.88 (s, 3H), 3.69 (s, 3H), 3.62 (s, 3H), 3.17 (s, 3H), 3.16-3.10 (m, 2H), 2.74 (dt, J=13.0, 3.7 Hz, 1H), 2.34 (q, J=8.9 Hz, 1H), 2.26 (dd, J=11.3, 2.6 Hz, 1H), 2.21-2.12 (m, 2H), 2.08-2.03 (m, 1H), 1.92 (dt, J=13.8, 8.7 Hz, 1H), 1.69-1.62 (m, 1H), 1.48 (dt, J=11.1, 3.1 Hz, 1H), 1.28-1.23 (m, 1H), 1.20 (ddd, J=13.3, 7.6, 2.8 Hz, 1H), 1.08 (dt, J=13.0, 3.1 Hz, 1H), 0.84 (t, J=7.4 Hz, 3H). $^{13}$C NMR (151 MHz, $CDCl_3$) δ 199.87, 169.08, 162.01, 160.36, 158.90, 139.01, 112.04, 108.08, 100.37, 97.46, 78.27, 74.62, 61.59, 55.86, 55.14, 53.88, 51.34, 40.54, 38.72, 31.99, 30.02, 24.29, 19.71, 13.17. HRMS calcd for $C_{24}H_{32}N_2O_5$ (MH+), 429.2389. found 429.2393.

Methyl (E)-2-((2S,3S)-9-bromo-3-ethyl-8-methoxy-1,2,3,4,6,7,12,12b-octahydroindolo[2,3-a]quinolizin-2-yl)-3-methoxyacrylate (10-bromomitragynine, VM1517)

Mitragynine (VM1500, 600 mg, 1.51 mmol) was dissolved in glacial acetic acid (5 mL) and then N-bromosuccinimide (402 mg, 1.5 equiv) was added. The mixture was stirred for 4 h at rt under Ar. Solution neutralized and basified with sat. aq. $NaHCO_3$ solution, extracted with DCM, dried over $Na_2SO_4$. The residue was redissolved in DCM and purified using flash column chromatography (gradient: 10-25% EtOAc in hexanes) to yield: 510 mg (71%) of VM1517 as a pale brown amorphous solid. $^1$H NMR (500 MHz, Chloroform-d) δ 7.76 (s, 1H), 7.44 (s, 1H), 7.11 (d, J=8.3 Hz, 1H), 6.36 (d, J=8.2 Hz, 1H), 3.86 (s, 3H), 3.75 (s, 3H), 3.71 (s, 3H), 3.22-3.14 (m, 1H), 3.12-2.99 (m, 3H), 2.96-2.89 (m, 3H), 2.57-2.42 (m, 3H), 1.85 (d, J=12.8 Hz, 1H), 1.62 (d, J=11.3 Hz, 1H), 1.57 (s, 2H), 0.87 (t, J=7.3 Hz, 3H). HRMS calcd for $C_{23}H_{30}BrN_2O_4$ (MH+), 477.1389. found 477.1383.

Methyl (E)-2-((2S,3S)-11-bromo-3-ethyl-8-methoxy-1,2,3,4,6,7,12,12b-octahydroindolo[2,3-a]quinolizin-2-yl)-3-methoxyacrylate (12-bromomitragynine, VM1518)

This compound was isolated as a minor product from the reaction leading to VM1517. Yield: 87 mg (12%) of VM1518 as a pale brown amorphous solid. $^1$H NMR (500 MHz, Chloroform-d) δ 7.83 (s, 1H), 7.44 (s, 1H), 7.18 (d, J=8.5 Hz, 1H), 6.95 (d, J=8.5 Hz, 1H), 3.92 (s, 3H), 3.74 (s, 3H), 3.71 (s, 3H), 3.22-2.88 (m, 9H), 2.60-2.42 (m, 4H), 1.86-1.71 (m, 3H), 1.64 (d, J=10.7 Hz, 2H), 0.87 (t, J=7.4 Hz, 3H). HRMS calcd for $C_{23}H_{30}BrN_2O_4$ (MH+), 477.1389. found 477.1383.

Methyl (E)-2-((2S,3S)-3-ethyl-9-(furan-3-yl)-8-methoxy-1,2,3,4,6,7,12,12b-octahydroindolo[2,3-a]quinolizin-2-yl)-3-methoxyacrylate (10-furylmitragynine, VM1519)

The procedure described for the synthesis of VM1511 was used. Instead of phenylboronic acid, (furan-3-yl)boronic acid was employed. Yield: 57%. Compound VM1519 is a pale brown amorphous powder. $^1$H NMR (600 MHz, Chloroform-d) δ 7.77 (s, 1H), 7.69 (t, J=1.1 Hz, 1H), 7.55 (t, J=1.7 Hz, 1H), 7.43 (s, 1H), 7.03 (d, J=7.9 Hz, 1H), 6.70 (d, J=1.0 Hz, 1H), 6.50 (d, J=8.0 Hz, 1H), 3.89 (s, 3H), 3.73 (s, 3H), 3.70 (s, 3H), 3.20-3.08 (m, 2H), 3.08-2.90 (m, 5H), 2.58-2.44 (m, 3H), 1.82-1.75 (m, 2H), 1.61 (dt, J=10.8, 3.3 Hz, 1H), 1.25-1.16 (m, 1H), 0.87 (t, J=7.4 Hz, 3H). $^{13}$C NMR (151 MHz, $CDCl_3$) δ 169.37, 160.77, 154.23, 143.68, 138.40, 135.14, 134.18, 124.01, 121.36, 117.98, 111.61, 110.53, 109.67, 108.98, 100.39, 61.78, 61.56, 57.98, 55.62, 53.90, 51.56, 40.95, 40.05, 30.18, 24.09, 19.34, 13.10. HRMS calcd for $C_{27}H_{32}N_2O_5$ (MH+), 465.2389; found 465.2384.

Methyl (E)-2-((2S,3S)-3-ethyl-11-(furan-3-yl)-8-methoxy-1,2,3,4,6,7,12,12b-octahydroindolo[2,3-a]quinolizin-2-yl)-3-methoxyacrylate (12-furylmitragynine, VM1520)

The procedure described for the synthesis of VM1511 was used. Instead of phenylboronic acid, (furan-3-yl)boronic acid was employed. Yield: 70%. Compound VM1520 is a pale brown amorphous powder. $^1$H NMR (600 MHz, Chloroform-d) δ 7.76 (s, 1H), 7.69 (d, J=1.3 Hz, 1H), 7.55 (d, J=1.7 Hz, 1H), 7.43 (s, 1H), 7.03 (d, J=7.9 Hz, 1H), 6.72-6.67 (m, 1H), 6.50 (d, J=8.0 Hz, 1H), 3.90 (s, 3H), 3.73 (s, 3H), 3.70 (s, 3H), 3.22-3.09 (m, 2H), 3.08-2.91 (m, 4H), 2.58-2.43 (m, 3H), 1.84-1.75 (m, 2H), 1.65-1.59 (m, 1H), 1.21 (m, 1H), 0.87 (t, J=7.4 Hz, 3H). $^{13}$C NMR (151 MHz, $CDCl_3$) δ 169.38, 160.77, 154.24, 143.69, 138.40, 135.15, 134.18, 124.02, 121.37, 117.99, 111.62, 110.53, 109.67, 108.99, 100.40, 61.78, 61.56, 57.99, 55.63, 53.91, 51.57, 40.96, 40.05, 30.19, 24.10, 19.34, 13.10. ESI-MS $C_{27}H_{32}N_2O_5$ (MH+): 465.0.

Methyl (E)-2-((2S,3S)-3-ethyl-9-(phenyl)-8-methoxy-1,2,3,4,6,7,12,12b-octahydroindolo[2,3-a]quinolizin-2-yl)-3-methoxyacrylate (10-phenylmitragynine, VM1521)

The procedure described for the synthesis of VM1511 was used. Yield: 67%. Compound VM1521 is a pale brown amorphous powder. $^1$H NMR (600 MHz, Chloroform-d) δ 7.88 (s, 1H), 7.59 (d, J=8.3 Hz, 1H), 7.48 (t, J=7.5 Hz, 2H), 7.41 (s, OH), 7.35 (t, J=7.4 Hz, 1H), 7.03 (dd, J=8.0, 0.9 Hz, 1H), 6.55 (dd, J=8.0, 0.9 Hz, 1H), 3.91 (s, 2H), 3.71 (s, 2H), 3.69 (s, 2H), 3.21-3.09 (m, 2H), 3.01 (ddd, J=13.9, 10.3, 3.8 Hz, 3H), 2.93 (dd, J=11.3, 5.6 Hz, 1H), 2.55 (td, J=11.6, 4.3 Hz, 1H), 2.46 (dd, J=11.7, 3.1 Hz, 2H), 1.78 (ddd, J=13.7, 11.3, 7.0 Hz, 1H), 1.72 (dt, J=12.9, 3.1 Hz, 1H), 1.60 (dt, J=11.0, 3.2 Hz, 1H), 1.19 (ddd, J=13.5, 7.5, 2.9 Hz, 1H), 0.87 (t, J=7.4 Hz, 3H). $^{13}$C NMR (151 MHz, $CDCl_3$) δ 169.38, 160.75, 154.37, 139.89, 134.90, 134.14, 129.31, 128.21, 126.85, 122.26, 119.02, 117.95, 111.59, 108.76, 100.54, 61.76, 61.61, 60.62, 58.02, 55.62, 53.94, 51.55, 40.97, 40.03, 30.16, 24.13, 21.29, 19.35, 14.42, 13.10. HRMS calcd for $C_{29}H_{34}N_2O_4$ (MH+), 475.2597. found 475.2593.

Methyl (E)-2-((2S,3S,7aS)-3-ethyl-9-(furan-3-yl)-7a-hydroxy-8-methoxy-1,2,3,4,6,7,7a,12b-octahydroindolo[2,3-a]quinolizin-2-yl)-3-methoxyacrylate (7-OH 10-furylmitragynine, VM1523)

The procedure described for the synthesis of VM1501 was used. Compound VM1523 is a pale brown amorphous powder. ESI-MS $C_{27}H_{32}N_2O_6$ (MH+): 481.2.

Methyl (E)-2-((2S,3S,7aS)-3-ethyl-11-(furan-3-yl)-7a-hydroxy-8-methoxy-1,2,3,4,6,7,7a,12b-octahydroindolo[2,3-a]quinolizin-2-yl)-3-methoxyacrylate (7-OH 12-furylmitragynine, VM1524)

The procedure described for the synthesis of VM1501 was used. Yield: 38%. Compound VM1524 is a pale brown amorphous powder. ESI-MS $C_{27}H_{32}N_2O_6$ (MH+): 481.2.

Methyl (E)-2-((2S,3S,7aS)-3-ethyl-9-(phenyl)-7a-hydroxy-8-methoxy-1,2,3,4,6,7,7a,12b-octahydroindolo[2,3-a]quinolizin-2-yl)-3-methoxyacrylate (7-OH 10-phenylmitragynine, VM1525)

The procedure described for the synthesis of VM1501 was used. Yield: 18%. Compound VM1525 is a pale brown amorphous powder. $^1$H NMR (600 MHz, Chloroform-d) δ 7.90-7.86 (m, 2H), 7.48 (d, J=8.6 Hz, 1H), 7.43 (s, 1H), 7.39 (t, J=7.7 Hz, 2H), 7.32-7.27 (m, 1H), 6.82 (d, J=8.6 Hz, 1H), 3.91 (s, 3H), 3.78 (s, 3H), 3.70 (s, 3H), 3.10 (dd, J=11.1, 2.5 Hz, 1H), 3.03 (dd, J=11.4, 2.2 Hz, 1H), 2.97 (dt, J=13.8, 3.6 Hz, 1H), 2.88-2.76 (m, 2H), 2.69-2.61 (m, 2H), 2.48 (dd, J=11.4, 3.0 Hz, 1H), 1.89 (dd, J=13.9, 3.1 Hz, 1H), 1.78-1.65 (m, 2H), 1.63 (dd, J=8.4, 5.6 Hz, 1H), 1.22 (m, 1H), 0.82 (t, J=7.3 Hz, 3H). $^{13}$C NMR (151 MHz, $CDCl_3$) δ 183.63, 169.60, 160.79, 155.29, 152.20, 138.03, 131.06, 129.66, 128.10, 127.47, 127.32, 126.87, 111.72, 109.52, 81.23, 61.70, 61.60, 58.21, 55.77, 51.49, 50.25, 40.56, 39.71, 36.42, 26.30, 19.16, 13.07. ESI-MS $C_{29}H_{34}N_2O_5$(MH+): 491.2.

Methyl (E)-2-((6'S,7'S)-6'-ethyl-5-(furan-3-yl)-4-methoxy-3-oxo-2',3',6',7',8',8a'-hexahydro-5'H-spiro[indoline-2,1'-indolizin]-7'-yl)-3-methoxyacrylate (10-furylmitragynine Pseudoindoxyl, VM1513)

The procedure described for the synthesis of VM1502 was used. Compound VM1513 is a yellow amorphous solid. ESI-MS $C_{27}H_{32}N_2O_6$ (MH+): 481.2.

Methyl (E)-2-((6'S,7'S)-6'-ethyl-7-(furan-3-yl)-4-methoxy-3-oxo-2',3',6',7',8',8a'-hexahydro-5'H-spiro[indoline-2,1'-indolizin]-7'-yl)-3-methoxyacrylate (12-furylmitragynine Pseudoindoxyl, VM1514)

The procedure described for the synthesis of VM1502 was used. Yield: 38%. Compound VM1514 is a yellow amorphous solid. $^1$H NMR (600 MHz, Chloroform-d) δ 7.71 (s, 1H), 7.56 (d, J=1.6 Hz, 1H), 7.37 (d, J=8.2 Hz, 1H), 7.28 (s, 1H), 6.66 (t, J=1.3 Hz, 1H), 6.22 (d, J=8.2 Hz, 1H), 5.34 (s, 1H), 3.92 (s, 3H), 3.62 (s, 3H), 3.59 (s, 3H), 3.18-3.08 (m, 3H), 3.06-2.97 (m, 1H), 2.83-2.76 (m, 2H), 2.68-2.64 (m, 1H), 2.35 (t, J=9.1 Hz, 2H), 2.26 (d, J=9.7 Hz, 2H), 2.15 (d, J=10.9 Hz, 1H), 1.66-1.57 (m, 1H), 0.85 (t, J=7.3 Hz, 4H). ESI-MS $C_{27}H_{32}N_2O_6$ (MH+): 481.2.

Methyl (E)-2-((6'S,7'S)-6'-ethyl-5-(phenyl)-4-methoxy-3-oxo-2',3',6',7',8',8a'-hexahydro-5'H-spiro[indoline-2,1'-indolizin]-7'-yl)-3-methoxyacrylate (10-phenylmitragynine Pseudoindoxyl, VM1515)

The procedure described for the synthesis of VM1502 was used. Compound VM1515 is a yellow amorphous solid.

Methyl (E)-2-((6'S,7'S)-5-chloro-6'-ethyl-4-methoxy-3-oxo-2',3',6',7',8',8a'-hexahydro-5'H-spiro[indoline-2,1'-indolizin]-7'-yl)-3-methoxyacrylate (10-chloromitragynine Pseudoindoxyl, VM1516)

Mitragynine pseudoindoxyl (VM1502, 5 mg, 0.012 mmol) was dissolved in glacial acetic acid (250 μL) and then N-chlorosuccinimide (4 mg, 2.5 equiv) was added. The mixture was stirred for 4 h at rt under Ar. Solution neutralized and basified with sat. aq. $NaHCO_3$ solution, extracted with DCM, dried over $Na_2SO_4$. The residue was redissolved in DCM and purified using preparative TLC (gradient: 10% MeOH in DCM) to yield: 2.1 mg (38%) of VM1516 as a bright yellow amorphous solid. $^1$H NMR (500 MHz, Chloroform-d) δ 7.41-7.35 (m, 2H), 6.51 (d, J=8.7 Hz, 1H), 4.06 (s, 3H), 3.74 (s, 3H), 3.66 (s, 4H), 3.37 (q, J=9.6 Hz, 1H), 3.26 (d, J=10.7 Hz, 1H), 3.19 (dd, J=12.6, 4.9 Hz, 1H), 3.09-2.93 (m, 2H), 2.61-2.45 (m, 2H), 2.29 (s, 1H), 1.84 (s, 1H), 1.33 (t, J=7.3 Hz, 1H), 1.16 (d, J=12.8 Hz, 1H), 1.01-0.94 (m, 3H). HRMS calcd for $C_{23}H_{29}N_2O_5Cl$ (MH+), 449.1843. found 449.1842.

Methyl (E)-2-((2S,3S,12bS)-3-ethyl-8-hydroxy-1,2,3,4,6,7,12,12b-octahydroindolo[2,3-a]quinolizin-2-yl)-3-methoxyacrylate (9-OH Corynantheidine, VM1532)

The compound was prepared from mitragynine (VM1500) using the method described for the synthesis of VM1507. VM1532 is a pale green amorphous powder. Yield: 88%. $^1$H NMR (500 MHz, DMSO-$d_6$) δ 11.00 (s, 1H), 9.72 (s, 1H), 9.45 (s, 1H), 7.58 (s, 1H), 6.81 (dd, J=28.9, 7.8 Hz, 2H), 6.39 (d, J=7.4 Hz, 1H), 4.66 (t, J=10.6 Hz, 1H), 3.84 (s, 3H), 3.75-3.32 (m, 9H), 3.30-3.05 (m, 3H), 2.66-2.53 (m, 1H), 2.44 (d, J=14.4 Hz, 1H), 1.87 (q, J=13.9, 12.3 Hz, 2H), 1.24 (t, J=10.3 Hz, 1H), 0.87 (t, J=7.1 Hz, 3H). HRMS calcd for $C_{22}H_{28}N_2O_4$(MH+), 385.2127. found 385.2114.

Methyl (E)-2-((2S,3S,12bS)-3-ethyl-1,2,3,4,6,7,12,12b-octahydroindolo[2,3-a]quinolizin-2-yl)-3-methoxyacrylate (Corynantheidine, VM1540)

VM1532 was converted to its triflate using the method described for the synthesis of VM1504. Yield: 30%. The triflate ester was converted to VM1540 using the method described for the synthesis of VM1508. VM1540 is an off-white amorphous powder. Yield: 34%. $^1$H NMR (500 MHz, Chloroform-d) δ 7.80 (s, 1H), 7.49-7.45 (m, 1H), 7.44 (s, 1H), 7.29 (dt, J=7.9, 1.0 Hz, 1H), 7.14-7.04 (m, 2H), 3.73 (s, 3H), 3.71 (s, 3H), 3.23-3.11 (m, 1H), 3.09-2.92 (m, 4H), 2.75-2.64 (m, 1H), 2.61-2.44 (m, 3H), 1.88-1.72 (m, 2H), 1.65 (dd, J=9.0, 5.6 Hz, 1H), 1.24-1.17 (m, 1H), 0.88 (t, J=7.4 Hz, 3H). ESI-MS $C_{22}H_{28}N_2O_3$(MH+): 369.0.

Methyl (E)-2-((2S,3S,7aS,12bS)-3-ethyl-7a-hydroxy-1,2,3,4,6,7,7a,12b-octahydroindolo[2,3-a]quinolizin-2-yl)-3-methoxyacrylate (7-OH Corynantheidine, VM1522)

VM1540 was converted to VM1522 using the method described for the synthesis of VM1501. VM1522 is a pale yellow amorphous powder. Yield: 10%. $^1$H NMR (500 MHz, Chloroform-d) δ 7.95 (s, 1H), 7.44 (s, 1H), 7.28 (d, J=8.0 Hz, 1H), 7.07 (t, J=8.0 Hz, 1H), 6.98 (d, J=7.8 Hz, 1H), 3.74 (s, 3H), 3.71 (s, 3H), 3.22-3.09 (m, 2H), 3.09-2.94 (m, 3H), 2.90 (d, J=16.0 Hz, 1H), 2.60-2.50 (m, 2H), 2.46 (d, J=11.9 Hz, 1H), 1.86-1.70 (m, 2H), 1.63 (d, J=11.2 Hz, 1H), 1.24-1.15 (m, 2H), 0.87 (t, J=7.3 Hz, 3H). ESI-MS $C_{22}H_{28}N_2O_4$ (MH+): 385.2.

Methyl (E)-2-((2S,3S,7aS,12bS)-3-ethyl-8-methoxy-7a-(piperidin-1-yl)-1,2,3,4,6,7,7a,12b-octahydroindolo[2,3-a]quinolizin-2-yl)-3-methoxyacrylate (7-(N-piperidinyl) mitragynine, VM1526)

Mitragynine (VM1500, 20 mg, 0.05 mmol) was dissolved in dry DCM under Ar and the solution was cooled to 0° C. PIFA (32 mg, 1.5 equiv) was added and the solution was stirred for 20 mins at 0° C. before the addition of piperidine (15 uL, 3 equiv). The solution was stirred for 1 h at 0° C. The mixture was poured into sat. aq. $NaHCO_3$ solution and extracted with DCM. The organic layer was dried over $Na_2SO_4$ and the solvent was removed under reduced pressure. The crude product was purified using preparative TLC (solvent: 70% EtOAc in hexanes) to yield 4.0 mg (16%) of VM1526 as a pale brown amorphous solid. $^1$H NMR (600 MHz, Chloroform-d) δ 7.44 (d, J=10.9 Hz, 1H), 7.25 (d, J=5.7 Hz, 2H), 6.72 (t, J=4.5 Hz, 1H), 3.81 (d, J=3.7 Hz, 6H), 3.71 (s, 3H), 3.16 (d, J=11.2 Hz, 1H), 3.02 (d, J=12.0 Hz, 2H), 2.87-2.81 (m, 1H), 2.77 (t, J=12.5 Hz, 1H), 2.49 (d, J=11.4 Hz, 2H), 1.83 (d, J=13.6 Hz, 1H), 1.71 (tt, J=14.4, 7.2 Hz, 1H), 1.43 (s, 2H), 1.31-1.19 (m, 5H), 0.82 (t, J=7.5 Hz, 3H). ESI-MS $C_{28}H_{39}N_3O_4$ (MH+): 482.3.

Methyl (E)-2-((2S,3S,12bS)-12-benzyl-3-ethyl-8-methoxy-1,2,3,4,6,7,12,12b-octahydroindolo[2,3-a]quinolizin-2-yl)-3-methoxyacrylate (N-benzyl Mitragynine, VM1533)

To the solution of mitragynine (1 equiv)(VM1500) in DMF was added NaH (1.2 equiv) at 0° C. After stirring at this temperature for 30 min benzyl bromide (1.05 equiv) was added. Reaction mixture was stirred at 0° C. for 1 hour then allowed to warm to ambient temperature and stirred for additional 3 hours. Diluted with EtOAc washed with saturated solution of $NaHCO_3$. EtOAc layer was dried over $MgSO_4$, filtered, concentrated. Crude VM1533 was purified by thin layer chromatography (basic alumina, hexanes: EtOAc). $^1$H NMR (500 MHz, $CDCl_3$) δ 7.25-7.15 (m, 4H), 7.02-6.97 (m, 2H), 6.94 (t, J=8.0 Hz, 1H), 6.64 (d, J=8.2 Hz, 1H), 6.46 (d, J=7.7 Hz, 1H), 5.27 (d, J=17.4 Hz, 1H), 5.19 (d, J=17.3 Hz, 1H), 3.89 (s, 3H), 3.65 (s, 3H), 3.48 (s, 3H), 3.35 (d, J=11.1 Hz, 1H), 3.19-3.09 (m, 1H), 3.08-2.97 (m, 2H), 2.93 (dt, J=13.6, 3.5 Hz, 2H), 2.70-2.55 (m, 2H), 2.35 (q, J=13.0 Hz, 1H), 1.84-1.68 (m, 2H), 1.55 (t, J=13.3 Hz, 1H), 1.17 (dt, J=14.3, 8.8 Hz, 1H), 0.86 (t, J=7.4 Hz, 3H). ESI-MS $C_{30}H_{36}N_2O_4$(MH+): 488.9.

Methyl (E)-2-((2S,3S,12bS)-3-ethyl-8-methoxy-12-methyl-1,2,3,4,6,7,12,12b-octahydroindolo[2,3-a]quinolizin-2-yl)-3-methoxyacrylate (N-methyl Mitragynine, VM1541)

To the solution of mitragynine (1 equiv)(VM1500) in DMF was added NaH (1.2 equiv) at 0° C. After stirring at this temperature for 30 min iodomethane (1.05 equiv) was added. Reaction mixture was stirred at 0° C. for 1 hour then allowed to warm to ambient temperature and stirred for additional 3 hours. Diluted with EtOAc washed with saturated solution of $NaHCO_3$. EtOAc layer was dried over $MgSO_4$, filtered, concentrated. Crude VM1541 was purified by thin layer chromatography (basic alumina, hexanes: EtOAc). $^1$H NMR (600 MHz, $CDCl_3$) δ 7.42 (s, 1H), 7.04 (t, J=8.0 Hz, 1H), 6.85 (d, J=8.2 Hz, 1H), 6.46 (d, J=7.7 Hz, 1H), 3.88 (s, 3H), 3.71 (d, J=0.8 Hz, 6H), 3.62 (s, 3H), 3.42-3.37 (m, 1H), 3.13-3.03 (m, 3H), 2.98-2.87 (m, 2H), 2.74-2.68 (m, 1H), 2.62 (td, J=10.5, 3.7 Hz, 1H), 2.45 (td, J=13.3, 11.0 Hz, 1H), 2.04-1.97 (m, 1H), 1.78 (ddt, J=18.3, 14.3, 7.2 Hz, 1H), 1.56 (m, 1H), 1.25-1.19 (m, 1H), 0.88 (t, J=7.4 Hz, 3H).

LiAlH4 reduction of mitragynine yielding a mixture of (E)-2-((2S,3S,12bS)-3-ethyl-8-methoxy-1,2,3,4,6,7,12,12b-octahydroindolo[2,3-a]quinolizin-2-yl)-3-methoxyprop-2-en-1-ol (VM1534), (2S,3S,12bS)-3-ethyl-8-methoxy-2-(3-methoxyprop-1-en-2-yl)-1,2,3,4,6,7,12,12b-octahydroindolo[2,3-a]quinolizine (VM1535), (2S,3S,12bS)-3-ethyl-8-methoxy-2-((R)-1-methoxypropan-2-yl)-1,2,3,4,6,7,12,12b-octahydroindolo[2,3-a]quinolizine (VM1536): To the solution of mitragynine (1 equiv) (VM1500) in diethyl ether at ambient temperature was added LiAlH4 (1.05 equiv). Reaction mixture was stirred for 5 hours then worked up according to Fieser work-up. Crude product was purified by thin layer chromatography (basic alumina, hexanes:EtOAc) to give 3 products. VM1534: This compound was isolated as a mixture containing compound above. Thus NMR is not available for reporting at his time. ESI-MS $C_{22}H_{30}N_2O_3$ (MH+): 371.0. VM1535: $^1$H NMR (600 MHz, Benzene-$d_6$) δ 7.20 (t, J=7.9 Hz, 1H), 6.89 (d, J=8.0 Hz, 1H), 6.79 (s, 1H), 6.45 (d, J=7.8 Hz, 1H), 5.14 (t, J=1.4 Hz, 1H), 4.70 (s, 1H), 3.85 (s, 3H), 3.51 (s, 3H), 3.44 (dddd, J=15.6, 11.7, 5.8, 2.7 Hz, 1H), 3.29-3.23 (m, 1H), 3.02-2.96 (m, 1H), 2.92 (dd, J=11.4, 2.4 Hz, 1H), 2.83 (ddd, J=11.1, 5.8, 1.3 Hz, 1H), 2.52 (td, J=11.5, 4.1 Hz, 1H), 2.35 (dt, J=12.7, 3.8 Hz, 1H), 2.26 (ddd, J=11.3, 3.0, 1.2 Hz, 1H), 1.76 (ddq, J=14.5, 10.7, 7.3 Hz, 1H), 1.62 (q, J=12.5 Hz, 1H), 1.50 (dt, J=7.4, 3.1 Hz, 1H), 1.45-1.41 (m, 1H), 1.22-1.14 (m, 1H), 0.87 (t, J=7.4 Hz, 3H). ESI-MS $C_{21}H_{28}N_2O_2$ (MH+): 341.1. VM1536: $^1$H NMR (600 MHz, Benzene-$d_6$) δ 7.19 (t, J=8.0 Hz, 1H), 6.84 (d, J=8.1 Hz, 1H), 6.75 (s, 1H), 6.45 (d, J=7.8 Hz, 1H), 3.51 (s, 3H), 3.44 (dddd, J=17.9, 11.8, 5.9, 2.7 Hz, 1H), 3.38 (dd, J=10.3, 3.5 Hz, 1H), 3.28-3.22 (m, 2H), 2.97 (dt, J=11.5, 2.4 Hz, 1H), 2.92 (dd, J=11.4, 2.4 Hz, 1H), 2.84 (ddd, J=11.2, 5.9, 1.3 Hz, 1H), 2.52 (td, J=11.5, 4.1 Hz, 1H), 2.20 (ddd, J=11.4, 2.7, 1.2 Hz, 1H), 1.85 (ddq, J=14.4, 10.4, 7.3 Hz, 1H), 1.58-1.53 (m, 1H), 1.50-1.41 (m, 2H), 1.36 (ddp, J=9.4, 6.3, 3.2 Hz, 1H), 1.22 (q, J=13.0, 12.5 Hz, 1H), 1.16 (ddd, J=9.5, 4.8, 2.0 Hz, 1H), 1.00 (d, J=6.6 Hz, 3H), 0.94 (t, J=7.4 Hz, 3H). ESI-MS $C_{21}H_{30}N_2O_2$ (MH+): 343.2.

Methyl (E)-2-((2S,3S,12bS)-3-ethyl-8-methoxy-1,2,3,4,6,7,7a,12,12a,12b-decahydroindolo[2,3-a]quinolizin-2-yl)-3-methoxyacrylate (VM1542)

To the solution of mitragynine (1.0 equiv)(VM1500) in MeOH at ambient temperature was added catalyst (Pd/C or PtO2, 0.2 equiv). Reaction atmosphere was replaced with $H_2$ and stirred at ambient temperature until TLC (basic alumina) indicated complete conversion. Reaction mixture was then filtered through plug of celite and concentrated. $^1$H NMR (500 MHz, Benzene-$d_6$) δ 7.41 (s, 1H), 7.11 (t, J=8.0 Hz, 1H), 6.31 (d, J=7.8 Hz, 1H), 6.28 (d, J=8.2 Hz, 1H), 3.61 (s, 3H), 3.53 (s, 3H), 3.42 (dd, J=6.8, 3.1 Hz, 1H), 3.31-3.22 (m, 2H), 3.09 (s, 3H), 3.03 (dd, J=11.5, 2.3 Hz, 1H), 2.87 (td, J=13.1, 11.6 Hz, 1H), 2.65-2.59 (m, 1H), 2.33 (ddt, J=17.6, 13.4, 6.8 Hz, 1H), 2.20 (dd, J=11.6, 3.1 Hz, 1H), 2.10-2.04 (m, 1H), 1.99-1.86 (m, 4H), 1.62 (td, J=8.0, 7.1, 2.6 Hz, 1H), 1.41 (d, J=12.8 Hz, 1H), 1.08 (t, J=7.5 Hz, 3H).

Methyl (E)-2-((2S,3S,7aS,12bS)-3-ethyl-7a,8-dimethoxy-1,2,3,4,6,7,7a,12b-octahydroindolo[2,3-a]quinolizin-2-yl)-3-methoxyacrylate (7-methoxymitragynine, VM1537)

Mitragynine (70 mg, 0.176 mmol)(VM1500) was dissolved in MeOH (6 mL) and cooled to 0° C. PIFA (83 mg, 1.1 equiv) was added and the mixture stirred at 0° C. for 1 h. Solvent removed under reduced pressure and the residue was transferred onto a silica gel loading cartridge. Purified using Flash chromatography (solvent: 1-5% MeOH/DCM) to yield 20 mg (26%) of VM1537 as a white amorphous solid. $^{1}$H NMR (600 MHz, Chloroform-d) δ 7.44 (s, 1H), 7.32 (t, J=8.0 Hz, 1H), 7.23 (d, J=7.6 Hz, 1H), 6.75 (d, J=8.3 Hz, 1H), 3.86 (s, 3H), 3.80 (s, 3H), 3.70 (s, 3H), 3.06-2.98 (m, 2H), 2.95 (dd, J=11.2, 2.4 Hz, 1H), 2.85 (s, 3H), 2.84-2.74 (m, 1H), 2.68 (dt, J=14.2, 2.4 Hz, 1H), 2.58 (ddd, J=11.5, 4.4, 2.2 Hz, 1H), 2.46 (dd, J=11.5, 3.0 Hz, 1H), 1.87 (dt, J=13.6, 3.0 Hz, 1H), 1.74-1.65 (m, 1H), 1.64-1.56 (m, 2H), 0.81 (t, J=7.4 Hz, 3H). $^{13}$C NMR (151 MHz, $CDCl_3$) δ 184.28, 169.52, 160.93, 156.77, 155.95, 131.15, 122.87, 114.50, 111.43, 109.02, 86.88, 62.13, 61.98, 58.30, 55.79, 52.12, 51.53, 50.37, 40.75, 39.52, 35.34, 26.19, 19.17, 13.04. ESI-MS $C_{24}H_{32}N_2O_5$ (MH+): 430.1.

Methyl (E)-2-((2S,3S,7aS,12bS)-7a-acetoxy-3-ethyl-8-methoxy-1,2,3,4,6,7,7a,12b-octahydroindolo[2,3-a]quinolizin-2-yl)-3-methoxyacrylate (7-acetoxymitragynine, VM1538)

Mitragynine (50 mg, 0.125 mmol)(VM1500) was dissolved in dry DCM (1.0 mL) and cooled to 0° C. Added $Pb(OAc)_4$ (112.8 mg, 2.03 eq.) and stirred for 4 hr at 0° C. The reaction mixture was poured into cold water and extracted with DCM (10 mL×5). The organic layer was dried over $Na_2SO_4$ and concentrated. Purified by Alumina basic TLC plate (solvent: 50% EtOAc in hexanes). Collected the 3rd band from the top to yield 17.8 mg (31%) of VM1538 as a pale brown amorphous solid. ESI-MS $C_{25}H_{32}N_2O_6$ (MH+): 457.3.

Methyl 2-(3-ethyl-8-methoxy-1,2,3,4,6,7,12,12b-octahydroindolo[2,3-a]quinolizin-2-yl)acetate (16-desmethoxymethylene-mitragynine, VM1527)

3-ethyl-8-methoxy-2-(2-methoxy-2-oxoethyl)-7,12-dihydro-6H-indolo[2,3-a]quinolizin-5-ium (38 mg, 0.108 mmol) was dissolved in 20 mL EtOH. 10 mg PtO2 was added and stirred under hydrogen atmosphere for 16 hours at rt at atmospheric pressure. The catalyst was filtered and the solvent was evaporated at reduced pressure. Purified using Flash column chromatography using 0-5% MeOH in DCM gradient. The procedure yields the racemic mixture of two enantiomers. Yield: 17 mg, 44%. $^{1}$H NMR (600 MHz, $CDCl_3$) δ 7.74 (s, 1H), 7.00 (t, J=7.9 Hz, 1H), 6.89 (d, J=8.1 Hz, 1H), 6.46 (d, J=7.8 Hz, 1H), 3.87 (s, 3H), 3.72 (s, 4H), 3.16-3.05 (m, 2H), 3.03-2.88 (m, 3H), 2.65-2.51 (m, 1H), 2.45-2.32 (m, 2H), 2.32-2.22 (m, 2H), 1.90 (d, J=11.7 Hz, 1H), 1.64 (s, 1H), 1.59-1.43 (m, 2H), 0.96-0.87 (m, 3H). ESI-MS $C_{21}H_{28}N_2O_3$ (MH+): 357.2.

Methyl 2-((7aS)-3-ethyl-7a-hydroxy-8-methoxy-1,2,3,4,6,7,7a,12b-octahydroindolo[2,3-a]quinolizin-2-yl)acetate (7-hydroxy-16-desmethoxymethylene Mitragynine, VM1529)

Dissolved racemic 16-desmethoxymethylene-mitragynine (14.9 mg, 0.0418 mmol)(VM1527) in dry DCM (2.2 mL) and cooled to 0° C. Added $Pb(OAc)_4$ (95%, 39.6 mg, 0.0849 mmol, 2.03 equiv) at 0° C. under argon and stirred for 2 hr. The reaction mixture was poured into cold water and extracted with DCM (5 mL×5). The organic layer was washed with brine, dried over $Na_2SO_4$ and concentrated. Purified by Alumina basic TLC plate (50% EtOAc in Hexanes). Collected the major band. 11.0 mg, light yellow amorphous solid (7-acetoxy-intermediate), 64% yield. This intermediate (11 mg, 0.0265 mmol) was dissolved in the solution of MeOH (350 μL) and aq. 15% NaOH (50 μL) and stirred at 0° C. for 2 hr. The reaction was poured into cold water (1 mL) and was extracted with DCM (1 mL×5). The organic layer was dried over $Na_2SO_4$, filtered, and concentrated to give light yellow solid. Purified by alumina basic TLC (60% EtOAc in Hexanes). Collecting the major band yielded 4.0 mg, 40% of VM1529 (2 diastereomers). ESI-MS $C_{21}H_{28}N_2O_4$ (MH+): 373.2.

Methyl 2-(6'-ethyl-4-methoxy-3-oxo-2',3',6',7',8',8a'-hexahydro-5'H-spiro[indoline-2,1'-indolizin]-7'-yl)acetate (16-desmethoxymethylene Mitragynine Pseudoindoxyl VM1530)

Dissolved 7-hydroxy-16-desmethoxymethylene-mitragynine (4 mg, 0.0107 mmol)(VM1529) and NaOMe (95%, 1.34 mg, 0.0234 mmol, 2.2 equiv) in dry MeOH (0.4 mL) and refluxed overnight. Added water, extracted with DCM and washed with brine. Purified using alumina prep TLC, 2% MeOH in DCM. Yield: 0.64 mg (16%). $^{1}$H NMR (600 MHz, $CDCl_3$+MeOD) δ 7.44 (s, 1H), 7.27 (td, J=8.1, 4.0 Hz, 1H), 6.31 (d, J=8.2 Hz, 1H), 6.08-6.02 (m, 1H), 3.80 (s, 3H), 3.26 (dt, J=3.2, 1.6 Hz, 3H), 3.14 (d, J=10.1 Hz, 1H), 3.10-3.05 (m, 1H), 2.40-2.28 (m, 2H), 2.27-2.12 (m, 4H), 2.08 (m, 1H), 2.01 (t, J=12.5 Hz, 1H), 1.98-1.79 (m, 3H), 1.58-1.38 (m, 2H), 1.29-1.12 (m, 3H), 0.85 (t, J=7.2 Hz, 3H). ESI-MS $C_{21}H_{28}N_2O_4$ (MH+): 373.2.

Methyl 2-(8-methoxy-1,2,3,4,6,7,12,12b-octahydroindolo[2,3-a]quinolizin-2-yl)acetate (20-desethyl-16-desmethxymethylene Mitragynine, VM1528)

8-methoxy-2-(2-methoxy-2-oxoethyl)-7,7a-dihydro-6H-indolo[2,3-a]quinolizin-5-ium (84 mg, 0.26 mmol) was dissolved in EtOH (20 mL) and 10 mg PtO2 was added. The mixture was stirred under hydrogen atmosphere at atmospheric pressure for 24 h at rt. Solvent was evaporated under reduced pressure and the residue purified using silica gel Flash chromatography (0-5% MeOH in DCM gradient). Yield: 22 mg (26%) racemic product VM1528 as a pale brown amorphous solid. $^{1}$H NMR (600 MHz, $CDCl_3$) δ 7.81 (s, 1H), 7.00 (t, J=7.9 Hz, 1H), 6.90 (d, J=8.1 Hz, 1H), 6.46 (d, J=7.8 Hz, 1H), 3.87 (s, 3H), 3.71 (s, 3H), 3.23 (t, J=15.9 Hz, 1H), 3.20-3.09 (m, 1H), 3.09-2.97 (m, 2H), 2.62-2.54 (m, 1H), 2.41 (ddd, J=27.5, 13.7, 3.8 Hz, 1H), 2.31 (ddd, J=23.2, 15.5, 7.1 Hz, 2H), 2.15 (dd, J=19.2, 8.8 Hz, 1H), 2.07 (dd, J=9.5, 6.0 Hz, 1H), 1.79 (dd, J=12.9, 1.3 Hz, 1H), 1.78 (dt, J=16.2, 8.2 Hz, 1H), 1.59-1.48 (m, 1H), 1.31 (dd, J=23.8, 11.9 Hz, 1H). ESI-MS $C_{19}H_{24}N_2O_3$(MH+): 329.2.

Methyl 2-((7aS)-7a-hydroxy-8-methoxy-1,2,3,4,6,7,7a,12b-octahydroindolo[2,3-a]quinolizin-2-yl)acetate (7-OH 20-desethyl-16-desmethxymethylene Mitragynine, VM1531)

Dissolved racemic 20-desethyl-16-desmethoxymethylene-mitragynine (22 mg, 0.067 mmol)(VM1528) in dry DCM (1.0 mL) and cooled to 0° C. Added $Pb(OAc)_4$ (95%, 60 mg, 2 equiv) at 0° C. under argon and stirred for 2 hr. The reaction mixture was poured into cold water and extracted with DCM (5 mL×5). The organic layer was washed with brine, dried over $Na_2SO_4$ and concentrated. Purified by Alumina basic TLC plate (5% MeOH in DCM). Collected the major band. 10.0 mg, light yellow amorphous solid (7-acetoxy-intermediate), 39% yield. This intermediate (10 mg, 0.026 mmol) was dissolved in the solution of MeOH (500 µL) and aq. 15% NaOH (50 µL) and stirred at 0° C. for 2 hr. The reaction was poured into cold water (1 mL) and was extracted with DCM (1 mL×5). The organic layer was dried over $Na_2SO_4$, filtered, and concentrated to give light yellow solid. Purified by alumina basic TLC (5% MeOH in DCM). Collecting the major band yielded 1.5 mg, 17% of VM1531 (2 diastereomers). ESI-MS $C_{19}H_{24}N_2O_4$ (MH+): 345.1.

Pharmacological and Behavioral Assays

Mice: Male CD1 mice (20-32 g) were obtained from Charles River Laboratories, C57BI/6J mice (20-32 g each) were obtained from Jackson Laboratories (Bar Harbor, ME). All mice were maintained on a 12-hour light/dark cycle with Purina rodent chow and water available ad libitum, and housed in groups of five until testing. All animal studies were preapproved by the Institutional Animal Care and Use Committees of the Memorial Sloan Kettering Cancer Center or University of Florida, in accordance with the 2002 National Institutes of Health Guide for the Care and Use of Laboratory Animals.

Rats: Sprague Dawley rats (200-400 g) were obtained from Charles River Laboratories. All mice were maintained on a 12-hour light/dark cycle with Purina rodent chow and water available ad libitum, and housed in groups of two until testing. All rats were maintained on a 12-hour light/dark cycle with Purina rodent chow and water available ad libitum, and housed in groups of five until testing. All animal studies were preapproved by the Institutional Animal Care and Use Committees of the Memorial Sloan Kettering Cancer Center, in accordance with the 2002 National Institutes of Health Guide for the Care and Use of Laboratory Animals.

Receptor-Binding Assays: Competition-binding assays in MOR-1/CHO (mu), DOR-1/CHO (delta) and KOR-1/CHO (kappa) were performed at 25° C. in 50 mM potassium phosphate buffer, pH 7.4, containing 5 mM magnesium sulfate (only in the case of CHO-MOR-1) for 90 min. Specific binding was defined as the difference between total binding and nonspecific binding, determined in the presence of 8 µM levallorphan. $^{125}$I-IBNtxA was used as the universal radioligand to determine the relative affinity of drugs in MOR-CHO, KOR—CHO and DOR-CHO. Binding in MOR/CHO was carried out in 50 mM potassium phosphate buffer with 5 mM $MgSO_4$ and 20 µg/ml protein while binding in KOR—CHO and DOR-/CHO was carried out in 50 mM potassium phosphate pH=7.0 buffer and 40 µg/ml protein. (Majumdar et al., *Bioorg. Med. Chem. Lett.*, 2011, 21, 4001-4004). 6TM/E11 receptor competition binding assays were carried out in whole brain membrane homogenates, performed at 25° C. in 50 mM potassium phosphate buffer, pH 7.4, containing 5 mM magnesium sulfate for 90 minutes in presence of 100 nM CTAP, 100 nM U50488 h and 100 nM DPDPE. $^{125}$I-IBNtxA was used as the radioligand in the assays, typically 500 micrograms of protein and 0.15 nM of the radioligand was used in a 0.5 mL assay. Specific binding was defined as the difference between total binding and nonspecific binding, determined in the presence of 8 µM levallorphan. Protein concentration was determined as described by Lowry et al. using bovine serum albumin as the standard (Lowry et al., *J. Biol. Chem.,* 1951, 193, 265-275). Kd, Bmax, and Ki values were calculated by nonlinear regression analysis (GraphPadPrism). Compounds that bind with the 6TM/E11 site and that exhibit K; less than 100 nM exhibit useful analgesia, and compounds that are selective for kappa3 exhibit improved side-effect profiles. In addition, compounds that bind to MOR-1 and DOR-1 and that exhibit K; less than 100 nM exhibit useful analgesia, and compounds that are selective for MOR-1/DOR-1 exhibit improved side-effect profiles. Similarly, it was observed in the past that compounds that bind with the 6TM/E11 site and that exhibit $K_i$ less than 100 nM exhibit useful analgesia, and compounds that are selective for 6TM/E11 exhibit improved side-effect profiles. (Majumdar, et al. *Proc. Natl. Acad. Sci. U.S.A,* 2011, 108, 19776-19783).

TABLE 3

Receptor affinities for Exemplary Compounds in Opioid Transfected Cell lines and Analgesia Effects in Mice
Receptor affinities in opioid transfected cell lines and analgesia in mice

| | Affinity ($K_i$ nM)[a] | | | Analgesia | Analgesia |
|---|---|---|---|---|---|
| Compound | MOR-1 | KOR-1 | DOR-1 | icv (µg) | sc (mg/kg) |
| VM1500 | 230 | 231 | 1011 | 42 | 166 |
| VM1501 | 37 | 132 | 91 | 0.06 | 0.46 |
| VM1502 | 0.8 | 24 | 3 | 0.38 | 0.76 |
| VM1503 | 375 | >1000 | >1000 | | — |
| VM1505 | 249 | 136 | 258 | | — |
| VM1506 | | | | | |
| VM1507 | 1.4 | 170 | 6.1 | | 0.18 |
| VM1508 | 0.46 | 19 | 2.9 | | 0.24 |
| VM1509 | 0.5 | 47 | 2.4 | | 0.32 |
| VM1510 | 2.5 | 31 | 20 | | 0.38 |
| VM1511 | 0.91 | 51 | 0.8 | | 1 |
| VM1512 | 0.94 | 39 | 1.5 | | 1.1 |
| VM1513 | | | | | |
| VM1514 | 41 | 119 | 40 | | |
| VM1515 | | | | | |
| VM1516 | 0.41 | 12 | 2.1 | | |
| VM1517 | 104 | 195 | 847 | | |
| VM1518 | | | | | |
| VM1519 | 281 | 129 | 653 | | |
| VM1520 | 278 | 185 | 617 | | |
| VM1521 | 364 | 204 | >1000 | | |
| VM1522 | 23 | 781 | 147 | 0.1 | |
| VM1523 | 36 | 36 | 109 | | |
| VM1524 | 117 | 338 | >1000 | | |
| VM1525 | | | | | |
| VM1526 | 247 | 72 | 369 | | |
| VM1527 | | | | | |
| VM1528 | | | | | |
| VM1529 | | | | | |
| VM1530 | | | | | |
| VM1531 | >1000 | >1000 | >1000 | | |
| VM1532 | 207 | 769 | 532 | 9 | |
| VM1533 | 93 | 395 | >1000 | | |
| VM1534 | >1000 | — | — | | |
| VM1535 | >1000 | — | — | | |
| VM1536 | >1000 | — | — | | |
| VM1537 | 190 | 90 | 997 | | |
| VM1538 | | | | | |

TABLE 3-continued

Receptor affinities for Exemplary Compounds in Opioid Transfected Cell lines and Analgesia Effects in Mice
Receptor affinities in opioid transfected cell lines and analgesia in mice

| | Affinity ($K_i$ nM)[a] | | | Analgesia | Analgesia |
|---|---|---|---|---|---|
| Compound | MOR-1 | KOR-1 | DOR-1 | icv (μg) | sc (mg/kg) |
| VM1539 | 52 | 14 | 332 | | |
| VM1540 | 57 | 385 | 172 | 0.1 | |
| VM1541 | 163 | 143 | >1000 | | |
| VM1542 | 116 | 329 | 374 | | |
| DAMGO | 3.3 | — | — | | |
| U50,488H | — | 0.73 | — | | |
| DPDPE | — | — | 1.39 | | |
| NTI | — | — | 0.46 | | |
| norBNI | — | 0.23 | — | | |
| morphine | 4.6 | — | — | 0.53 | 4.6 |

[a]Competition studies were performed with the indicated compounds against $^{125}$I-IBNtxA (0.1 nM) in membranes from CHO cells stably expressing the indicated cloned mouse opioid receptors.
[b]Cumulative dose-response curves were carried out on groups of CD1 mice (n = 10) using radiant heat tail-flick assays with indicated compound (sc and icv), and antinociception was tested 15 min later at peak effect. Results from two independent experiments are shown as mean.
"—"Denotes not determined or not applicable.

[$^{35}$S]GTPγS functional assays: [$^{35}$S]GTPγS binding was performed on membranes prepared from stably transfected cells in the presence and absence of the indicated compound for 60 min at 30° C. in the assay buffer (50 mM Tris-HCl, pH 7.4, 3 mM $MgCl_2$, 0.2 mM EGTA, and 10 mM NaCl) containing 0.05 nM [$^{35}$S]GTPγS; 2 μg/ml each leupeptin, pepstatin, aprotinin, and bestatin; and 30 μM GDP, as previously described (Bolan et al 2004 Synapse). After the incubation, the reaction was filtered through glass-fiber filters (Whatman Schleicher & Schuell, Keene, NH) and washed three times with 3 ml, of ice-cold 50 mM Tris-HCl, pH 7.4, on a semiautomatic cell harvester. Filters were transferred into vials with 3 ml, of Liquiscent (National Diagnostics, Atlanta, GA), and the radioactivity in vials was determined by scintillation spectroscopy in a Tri-Carb 2900TR counter (PerkinElmer Life and Analytical Sciences). Basal binding was determined in the presence of GDP and the absence of drug. Data was normalized to 1 μM DAMGO, DPDPE, and U50,488 for MOR, DOR, and KOR binding, respectively. $EC_{50}$ and % Emax values were calculated by nonlinear regression analysis (GraphPad Prism, San Diego, CA).

TABLE 4

[$^{35}$S]GTPγS functional assays in transfected cell lines.

| | [$^{35}$S]GTPγS functional assays[a] | | | | | |
|---|---|---|---|---|---|---|
| | MOR-1 | | KOR-1 | | DOR-1 | |
| Compound | $EC_{50}$ (nM) | Emax (%) | $EC_{50}$ (nM) | $IC_{50}$ (nM) | $EC_{50}$ (nM) | $IC_{50}$ (nM) |
| VM1500 | 203 | 65 | — | >4 uM | — | >4 uM |
| VM1501 | 53 | 77 | — | 2524 | — | 691 |
| VM1502 | 1.7 | 84 | — | 31 | — | 61 |
| VM1503 | — | — | — | — | — | — |
| VM1505 | — | — | — | — | — | — |
| VM1506 | | | | | | |
| VM1507 | 2 | 124 | — | — | — | 293 |
| VM1508 | 1.4 | 116 | — | 252 | — | 193 |
| VM1509 | 0.7 | 122 | — | 721 | — | 73 |
| VM1510 | 3.9 | 120 | — | — | — | — |
| VM1511 | 1.4 | 123 | — | 171 | 0.83 (89)[b] | — |
| VM1512 | 1.5 | 100 | — | 202 | — | 39 |
| VM1513 | | | | | | |
| VM1514 | >1000 | — | 40 | — | 244 | — |
| VM1515 | | | | | | |
| VM1516 | | | | | | |
| VM1517 | | | | | | |
| VM1518 | | | | | | |
| VM1519 | | | | | | |
| VM1520 | | | | | | |
| VM1521 | | | | | | |
| VM1522 | 34 | 116 | | | | |
| VM1523 | | | | | | |
| VM1524 | | | | | | |
| VM1525 | | | | | | |
| VM1526 | | | | | | |
| VM1527 | | | | | | |
| VM1528 | | | | | | |
| VM1529 | | | | | | |
| VM1530 | | | | | | |
| VM1531 | | | | | | |
| VM1532 | 422 | 62 | | | | |
| VM1532 | | | | | | |
| VM1533 | | | | | | |
| VM1534 | | | | | | |
| VM1535 | | | | | | |
| VM1536 | | | | | | |
| VM1537 | | | | | | |
| VM1538 | | | | | | |
| VM1539 | | | | | | |
| VM1540 | 104 | 74 | | | | |
| VM1541 | | | | | | |
| VM1542 | | | | | | |

TABLE 4-continued

[$^{35}$S]GTPγS functional assays in transfected cell lines.

| Compound | [$^{35}$S]GTPγS functional assays[a] MOR-1 $EC_{50}$ (nM) | Emax (%) | KOR-1 $EC_{50}$ (nM) | $IC_{50}$ (nM) | DOR-1 $EC_{50}$ (nM) | $IC_{50}$ (nM) |
|---|---|---|---|---|---|---|
| DAMGO | 19 | — | — | — | — | — |
| U50,488H | — | — | 17 | — | — | — |
| DPDPE | — | — | — | — | 10 | — |
| NTI | — | — | — | — | — | 0.72 |
| norBNI | — | — | — | 2.9 | — | — |

[a]Efficacy data were obtained using agonist induced stimulation of [$^{35}$S]GTPγS binding assay. Efficacy is represented as $EC_{50}$ (nM) and percent maximal stimulation ($E_{max}$) relative to standard agonist DAMGO (MOR-1), DPDPE (DOR-1), or U50,488H (KOR-1) at 1000 nM. To determine the antagonist properties of a compound, membranes were incubated with 100 nM of the appropriate agonist in the presence of varying concentrations of the compound

[b]Compound 8 is an agonist at DOR-1.

"—" Denotes not determined or not applicable.

As depicted in FIG. 7A, [$^{35}$S]GTPγS binding was performed on membranes prepared from transfected CHO cells stably expressing mu opioid receptors in the presence and absence of the indicated compound. Data was normalized to 100 nM DAMGO for mu receptor binding. $EC_{50}$, IC50, and % Emax values were calculated by nonlinear regression analysis. As depicted in FIG. 7B and FIG. 7D, β-arrestin-2 recruitment was determined using the DiscoveRx PathHunter enzyme complementation assay using modified MOR-1 in CHO cells. Compounds were found to be completely G-protein biased. As depicted in FIG. 7B, β-arrestin-2 recruitment was evaluated for compound VM1502. As depicted in FIG. 7D, β-arrestin-2 recruitment was evaluated for compounds VM1500, VM1501, VM1502, VM1507, VM1508, VM1509, VM1511, VM1512, DAMGO, and endomorphin-2. As depicted in FIG. 7C, antagonism of β-arrestin-2 recruitment was evaluated: the same cells as for FIG. 7B and FIG. 7D were incubated with the antagonist (VM1501, VM1502) for 30 minutes at 37° C. prior to the addition of agonist (10 μM DAMGO) at MOR-1. Compounds VM1501 and VM1502 were able to antagonize β-arrestin-2 recruitment by DAMGO.

β-arrestin-2 Recruitment Assay: β-arrestin-2 recruitment was determined using the PathHunter enzyme complementation assay (DiscoveRx. Fremont, CA) using modified MOR in CHO cells (a gift from DiscoveRx). Cells were plated at a density of 2500 cells/well in a 384-well plate as described in the manufacturer's protocol. The following day, cells were treated with the indicated compound for 90 minutes at 37° C. followed by incubation with PathHunter detection reagents for 60 minutes. Chemiluminescence was measured with an Infinite M1000 Pro plate reader (Tecan, Männedorf, Switzerland). For the antagonist dose response assay, the cells were incubated with the antagonist for 30 minutes at 37° C. prior to the addition of agonist. Following antagonist treatment, the cells were treated with 10 μM DAMGO for 90 minutes at 37° C. and chemiluminescence was detected using the PathHunter detection reagents. It was observed that compounds, which do not recruit β-arrestin-2 up to 10 μM concentrations and are totally G-protein biased exhibit useful analgesia, with far improved side-effect profiles.

Tail Flick Analgesia Assays: Antinociception was determined using the radiant heat tail flick technique using an Ugo Basile model 37360 instrument as previously described. (Váradi et al. *ACS Chemical Neuroscience,* 2015, 6, 1813-1824; Váradi et al. *ACS Chem Neuroscience,* 2015, 6, 1570-1577). The intensity was set to achieve a baseline between 2 and 3 seconds. Baseline latencies were determined before experimental treatments for all mice or rats. Tail flick antinociception was assessed quantally as a doubling or greater of the baseline latency, with a maximal 10 second latency to minimize damage to the tail. Data were analyzed as percent maximal effect, % MPE was calculated according to the formula: % MPE [(observed latency−baseline latency)/(maximal latency−baseline latency)]×100. Compounds were injected subcutaneously (s.c.) or intracerebroventricularly (i.c.v.), and antinociception was assessed 15 min later at the peak effect. Intracerebroventricular dosing (i.c.v.) was carried out as previously described. (Haley et al., *Br. J. Pharmacol. Chemother.,* 1957, 12, 12-15). Briefly, the mice were anesthetized by isoflurane. A small incision was made, and synthetic opiate analog (2 ul/mouse) was injected using a 10 uL Hamilton syringe fitted to a 27-gauge needle. Injections were made into the right lateral ventricle at the following coordinates: 2 mm caudal to bregma, 2 mm lateral to sagittal suture, and 2 mm in depth. Mice were tested for antinociception 15 minutes post injection. Compounds with an $ED_{50}$ less than 10 mg/kg are preferred because the potency allows for smaller dosages, but higher $ED_{50}$'s are possible. For the antagonism studies β-FNA (40 mg/kg, s.c.) and norbinaltorphimine (norBNI, 10 mg/kg, s.c.) were administered 24 hours before administration of the agonist opioid drug. Naltrindole (NTI, 0.5 mg/kg, s.c.) was administered 15 min before administration of the agonist opioid drug. In vivo experiments were evaluated using GraphPad Prism, San Diego, CA. It was observed that compounds whose analgesia is attenuated by the selective mu antagonist β-FNA while insensitive to delta and kappa antagonists like NTI and norBNI respectively exhibit useful analgesia, with far improved side-effect profiles.

Figure 8A:
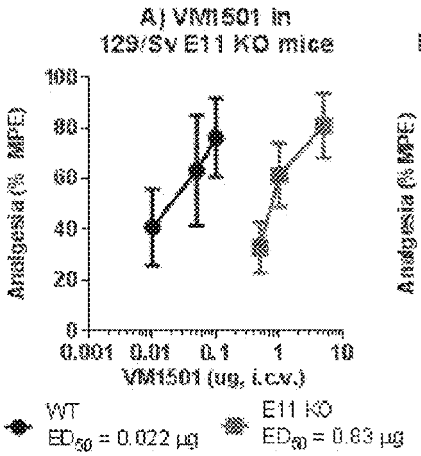
FIGS. 8A-8E show in vivo pharmacological evaluation of compound VM1501.

FIG. 8A depicts dose-response curves of antinociception of VM1501 and given supraspinally in 129/Sv mice (wild type and Exon11 knockout). Two independent determinations of the cumulative dose-response curves were performed on groups of mice (n=5) for antinociception in the tail flick assay with VM1501 intracerebroventricularly. Animals were tested 15 min later at peak effect to generate the analgesic dose-response curve. Each point represents mean t SEM for 10 mice. $ED_{50}$ values (and 95% CI) were 0.022 μg in wild type and 0.83 μg in Exon11 knockout animals. VM1501's analgesia is mediated, in part, by Exon11 6TM splice variants. As depicted in FIG. 8C, respiratory rate of animals was evaluated: animals were randomly assigned to receive saline (n=5), VM1501 (2.5 mg/kg, sc, n=5), or morphine (10 mg/kg, n=5 at). Each animal's baseline average breath rate was measured every 5 min for 25 min before drug injection, and breath rates after drug injection are expressed as a percent of baseline. Breath rates were measured for 50 minutes post-injection. While morphine caused respiratory depression at 2× antinociceptive $ED_{50}$ dose (10 mg/kg), VM1501 did not depress respiratory rate at 5× antinociceptive $ED_{50}$ dose (2.5 mg/kg) and was not significantly different from saline at any time point, whereas morphine (10 mg/kg) decreased respiratory depression in comparison with VM1501 ($p<0.05$) as determined by repeated-measures ANOVA followed by Tukey's multiple-comparison test.

Figure 9A:
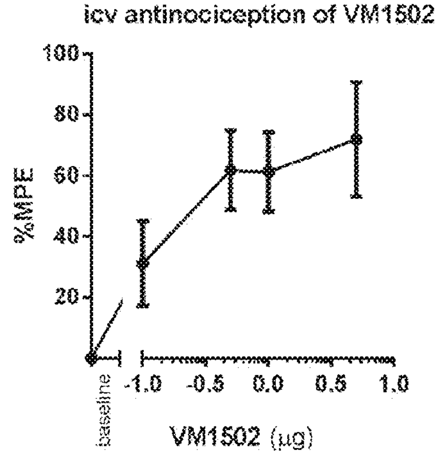
FIGS. 9A-9C show antinociception of compound VM1502 upon intracerebroventricular, subcutaneous, and oral administration.
Figure 9B:
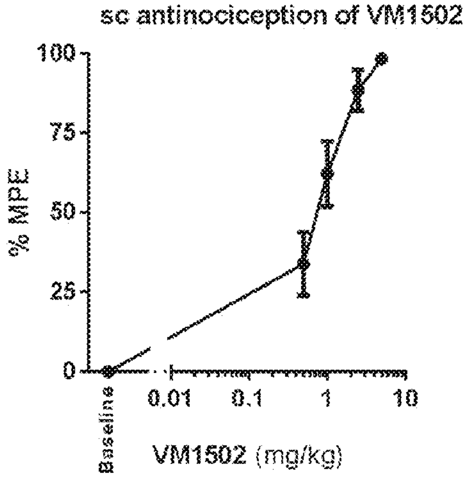
Figure 9C:
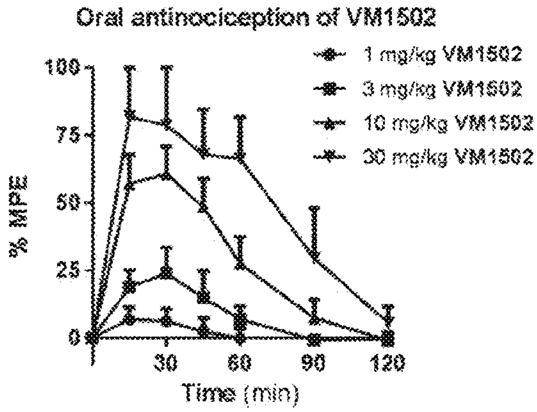

FIGS. 9A-9C show antinociception of compound VM1502 upon intracerebroventricular, subcutaneous, and oral administration. FIG. 9A shows dose-response curves of antinociception of VM1502 and morphine given supraspinally in CD1 mice: two independent determinations of the cumulative dose-response curves were performed on groups of mice (n=5) for antinociception in the tail flick assay with VM1502 intracerebroventricularly. Animals were tested 15 min later at peak effect to generate the analgesic dose-response curve. Each point represents mean t SEM for 10 mice. $ED_{50}$ values (and 95% CI) were 0.38 μg (0.18, 0.81) for VM1502. In FIG. 9B, dose-response curves of antinociception of VM1502 were given subcutaneously in CD1 mice: three independent determinations of the cumulative dose-response curves were performed on groups of mice (n=10) for antinociception in the tail flick assay, 30 mice in total. $ED_{50}$ (and 95% CI)=0.76 mg/kg (0.56, 0.83). In FIG. 9C, time course of tail flick antinociception of VM1502 given orally in CD1 male mice. Groups of mice (n=10) were given different doses of VM1502 orally by gavage and tested for analgesic response at the indicated time points. $ED_{50}$ (and 95% CI)=7.5 mg/kg (4.3, 13) [a]The means of each point in each determination were determined as percentage maximal possible effect (% MPE) [(observed latency−baseline latency)/(maximal latency−baseline latency)]×100. Points represent mean t SEM.

FIG. 10 shows antinociception of compound VM1502 in rats upon subcutaneous administration. In FIG. 10, groups of rats (n=3) were assessed for subcutaneously given VM1502 analgesia at 15 mins in a cumulative dose-response paradigm where animals received escalating doses of VM1502 to generate the analgesic dose-response curve. The $ED_{50}$ was 1.4 mg/kg.

Figure 11A:
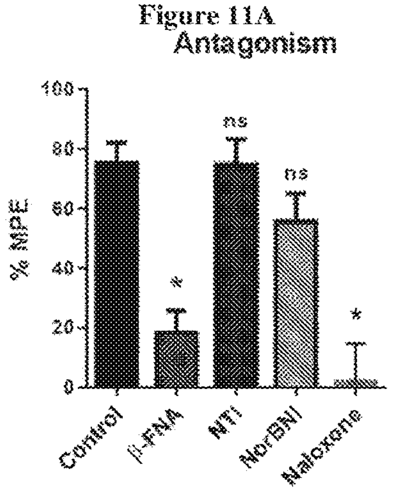
FIGS. 11A-11C show pharmacological and genetic reversal of antinociception of compound VM1502.
Figure 11B:
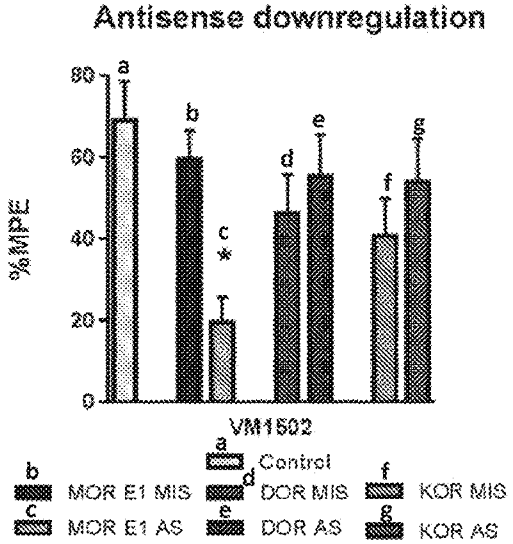
Figure 11C:
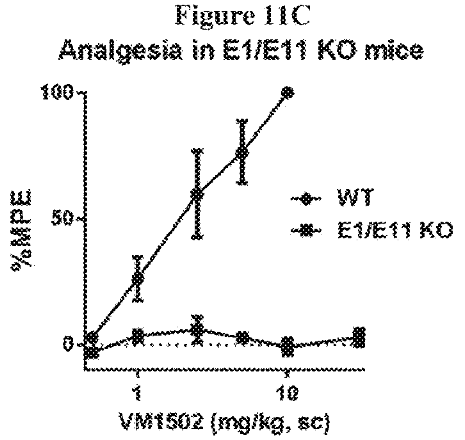

FIGS. 11A-11C show pharmacological and genetic reversal of antinociception of compound VM1502. FIG. 11A depicts reversal of antinociception by selective antagonists: Groups of CD1 mice (n=10) received VM1502 (1.5 mg/kg sc) and the indicated antagonist. β-funaltrexamine (β-FNA; 40 mg/kg sc) and norbinaltorphimine (norBNI; 10 mg/kg sc) were administered 24 hours before agonist testing. Naltrindole (NTI; 0.5 mg/kg sc) and naloxone (1 mg/kg) were administered 15 minutes before VM1502. All antinociception testing was performed 15 min after the administration of VM1502. Similar results were observed in two independent replications. VM1502 antinociception is insensitive to NTI and norBNI, whereas antinociception is antagonized by β-FNA (two-way ANOVA followed by Bonferroni post hoc comparisons test, $p<0.05$). All values are expressed as the mean±SEM. In FIG. 11B, antisense (AS) and mismatch (MIS) oligodeoxynucleotides were designed based upon the published sequences of the mouse mu opioid receptor gene (Oprm1), delta opioid receptor gene (Oprd1), and kappa opioid receptor gene (Oprk1). Antisense oligodeoxynucleotide injection: Groups of mice (n=15) received the stated antisense (5-10 μg) or mismatch (5-10 μg) oligodeoxynucleotide icv under light isoflurane anesthesia on days 1, 3 and 5. Tail flick antinociception was tested on day 6. Control groups received no injection prior to testing. On test day, mice received VM1502 (1.5 mg/kg, sc). All experiments were performed 3 times with similar results observed with each determination. Analgesic response of VM1502 was only affected in MOR-1-downregulated mice (one-way ANOVA followed by Bonferroni post hoc comparisons test). *Significantly different from control ($p<0.05$). FIG. 11C depicts dose-response curves of antinociception of VM1502 and given subcutaneously in C57/BL6 (wild type and E1-E11 double MOR-1 knockout). The analgesia of VM1502 was eliminated in MOR-1 knockout mice suggesting that analgesia of VM1502 is mediated through MOR-1.

Antisense Assays: Antisense (AS) and mismatch (MS) oligodeoxynucleotides were designed based upon the published sequences of the mouse mu opioid receptor gene (Oprm1), delta opioid receptor gene (Oprd1), and kappa opioid receptor gene (Oprk1) (Table 5). These probes have been previously described and validated. (Pasternak et al., *Brain Research,* 1999, 826, 289-292; Rossi et al., *Neurosci. Lett.,* 1996, 216, 1-4; Rossi et al., *Neurosci. Lett.,* 1995, 198, 99-102; Rossi et al., *Brain Res.,* 1997, 753, 176-179). Antisense oligodeoxynucleotide injection: Groups of mice received the stated antisense (5-10 μg) or mismatch (5-10 μg) oligodeoxynucleotide i.c.v. under light isoflurane anesthesia on days 1, 3 and 5, as previously described. (Rossi et al., *Neurosci. Lett.,* 1995, 198, 99-102). Tail flick antinociception was tested on day 6. Control groups received no injection prior to testing. On test day, mice received VM 1502 (1.5 mg/kg, s.c.), morphine (0.75 μg, i.c.v.), DPDPE (10 μg, i.c.v.), or U50,488H (5 mg/kg, s.c.). All experiments were performed 3 times with similar results observed with each determination. Antisense oligo downregulation experiments of were similarly carried out with VM1501 by downregulating mouse mu opioid receptor gene (Oprm1). It was observed that compounds whose analgesia is attenuated by oligos targeting Oprm1 while being insensitive to Oprk1 and Oprd1 exhibit useful analgesia, with far improved side-effect profiles.

Figure 8B:
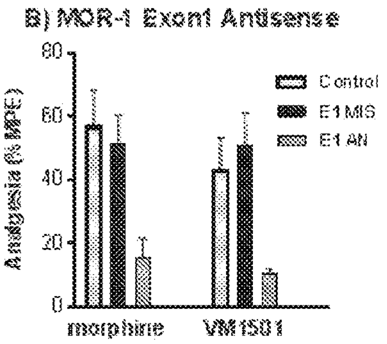
Figure 8C:
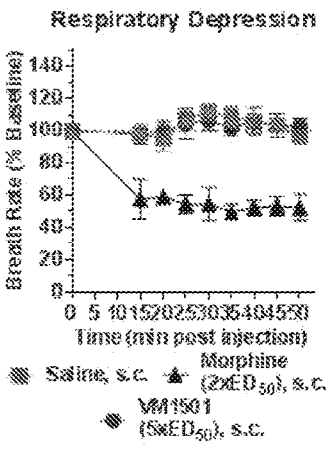

As depicted in FIG. 8B, antisense (AN) and mismatch (MIS) oligodeoxynucleotides were designed based upon the published sequences of the mouse mu opioid receptor gene (Oprm1). Antisense oligodeoxynucleotide injection: Groups of mice (n=15) received the stated antisense (5-10 pg) or mismatch (5-10 μg) oligodeoxynucleotide icv under light isoflurane anesthesia on days 1, 3 and 5. Tail flick antinociception was tested on day 6. Control groups received no injection prior to testing. On test day, mice received VM1501 (1.0 mg/kg, sc). All experiments were performed 3 times with similar results observed with each determination. Analgesic response of VM1501 was diminished in MOR-1-downregulated mice (one-way ANOVA followed by Bonferroni post hoc comparisons test). VM1501's analgesia is mediated, in part, by MOR-1.

TABLE 5

Sequences of Antisense (AS) and mismatch (MS) oligodeoxynucleotides.

| Target | Antisense | SEQ ID NO: | Mismatch Control | SEQ ID NO: |
|---|---|---|---|---|
| MOR-1 exon 1 | CGCCCCAGCCTCTT CCTCT | 1 | CGCCCCGACCT CTTCCCTT | 3 |

TABLE 5-continued

Sequences of Antisense (AS) and mismatch (MS) oligodeoxynucleotides.

| Target | Antisense | SEQ ID NO: | Mismatch Control | SEQ ID NO: |
|---|---|---|---|---|
| DOR-1 exon 3 | AGGGGAAGGTCGG GTAGG | 2 | GAGGAGAGGTG CGTGGAG | 4 |
| KOR-1 exon 2 | CGCCCCAGCCTCTT CCTCT | 1 | CTCCGCGCTCT CACCCTCT | 5 |

Analgesia in E11 MOR-1 KO mice and E1-E11 MOR-1 KO mice: Cumulative dose response curves were carried out in mice lacking either E11 splice variants of the mu opioid receptor (E11 MOR-1 KO mice) and/or both E1 and E11 splice variants of mu opioid receptor (E1-E11 MOR-1 KO mice) with the drug administered either icy or sc using radiant tail flick analgesia assay. It was observed in the past that compounds whose analgesia is either completely lost or attenuated in E11 MOR-1 KO mice exhibit useful analgesia, and improved side-effect profiles. (Majumdar et al., *Proc. Natl. Acad. Sci. U.S.A.,* 2011, 108, 19776-19783).

Gastrointestinal motility assay: Gastrointestinal transit was determined as described by Paul and Pasternak (Paul et al., *Eur. J. Pharmacol.,* 1988, 149, 403-404). In brief, after withholding food for 8 hours, animals received the indicated drug and then were given a charcoal meal (0.2 mL; 10% of purified charcoal and 2.5% of gum tragacanth, w/v) by gavage and were sacrificed 30 min later. The distance traveled by the charcoal meal was then measured and reported in centimeters. It was observed that compounds whose analgesia is E11 MOR-1 dependent and/or are G-protein biased MOR-1 agonists with DOR-1 antagonism exhibit useful analgesia, and improved side-effect profiles.

Figure 8D:
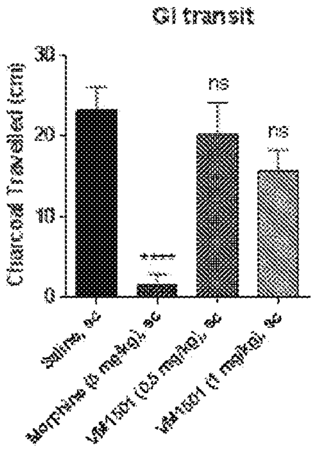
Figure 8E:
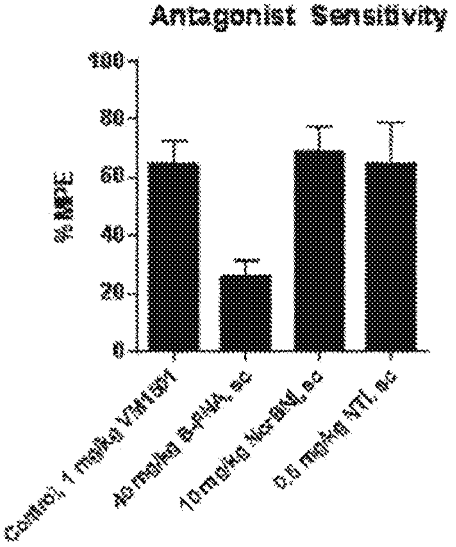

As depicted in FIG. 8D, gastrointestinal transit was evaluated: groups of mice (n=10) received saline, morphine (5 mg/kg), or VM1501 (0.5 and 1 mg/kg) before receiving an oral dose of 0.2 mL of charcoal meal (2.5% gum tragacanth in 10% activated charcoal in water) by gavage. Animals were sacrificed 30 min later, and the distance traveled by charcoal was measured. VM1501 did not lower transit significantly compared with saline (P<0.05) and the effect was significantly less than morphine at both doses (P<0.05) as determined by ANOVA followed by Tukey's multiple-comparison test. In FIG. 8E, reversal of antinociception by selective antagonists was evaluated: groups of CD1 mice (n=10) received VM1501 (1.0 mg/kg sc) and the indicated antagonist. β-funaltrexamine (β-FNA; 40 mg/kg sc) and norbinaltorphimine (norBNI; 10 mg/kg sc) were administered 24 hours before agonist testing. Naltrindole (NTI; 0.5 mg/kg sc) and naloxone (1 mg/kg) were administered 15 minutes before VM1501. All antinociception testing was performed 15 min after the administration of VM1501. Similar results were observed in two independent replications. VM1501 antinociception is insensitive to NTI and norBNI, whereas antinociception is antagonized by β-FNA (two-way ANOVA followed by Bonferroni post hoc comparisons test, p<0.05). All values are expressed as the mean t SEM.

Conditional place preference/Aversion and Locomotor activity: Mice were conditioned with a counterbalanced place conditioning paradigm using similar timing as detailed previously. (Váradi et al. *ACS Chemical Neuroscience,* 2015, 6, 1813-1824). The amount of time subjects spent in each of three compartments was measured over a 30 min testing period. Prior to place conditioning, the animals (n=95) did not demonstrate significant differences in their time spent exploring the left (543±13 s) vs. right (571±12 s) compartments (p=0.15; Student's t-test), resulting in a combined preconditioning response of −0.1±19 s. During each of the next two days, mice were administered vehicle (0.9% saline) and consistently confined in a randomly assigned outer compartment for 40 min, half of each group in the right chamber, half in the left chamber. Four hours later, mice were administered morphine (10 mg/kg, i.p.), U50,488H (30 mg/kg, i.p.), cocaine (10 mg/kg, i.p.), or VM1502 (1.3 or 3.2 mg/kg, sc) and confined to the opposite compartment for 40 min. Conditioned place preference data is presented as the difference in time spent in drug- and vehicle-associated chambers, and were analyzed via repeated measures two-way ANOVA with the difference in time spent on the treatment- vs. vehicle-associated side as the dependent measure and conditioning status as the between-groups factor. Where appropriate, Tukey's HSD or Sidak's multiple comparison post-hoc tests were used to assess group differences. Effects were considered significant when p<0.05. All effects are expressed as mean t SEM. It was observed that compounds whose analgesia is E11 MOR-1 dependent and/or are G-protein biased MOR-1 agonists with DOR-1 antagonism exhibit useful analgesia, and improved side-effect profiles. Tolerance and physical dependence studies: Groups of mice (n=10) were treated with either morphine (6 mg/kg s.c.) or test compound (1.5 mg/kg s.c.) twice daily till animals show no analgesic activity. Tail-flick latencies were determined before and 30 minutes after each injection. (Gistrak et al., *J. Pharmacol. Exp. Ther.,* 1989, 251 (2), 469-476). Animals were challenged with naloxone (1 mg/kg, s.c.) to precipitate withdrawal in completely tolerant animals. Animals were evaluated for signs of diarrhea and jumping.[15] We have observed that compounds whose analgesia is E11 MOR-1 dependent and/or are G-protein biased MOR-1 agonists with DOR-1 antagonism exhibit useful analgesia, and improved side-effect profiles.

Figure 12A:
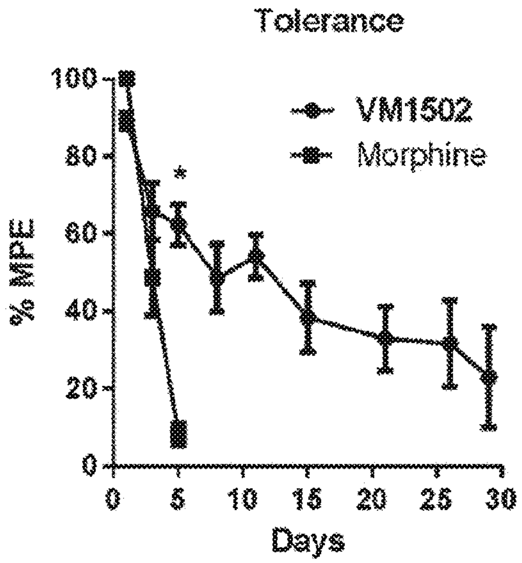
FIGS. 12A-12E show side effect studies with compound VM1502.
Figure 12B:
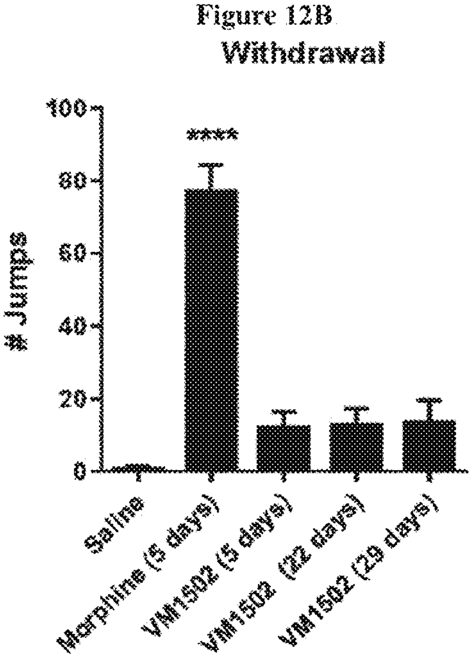
Figure 12C:
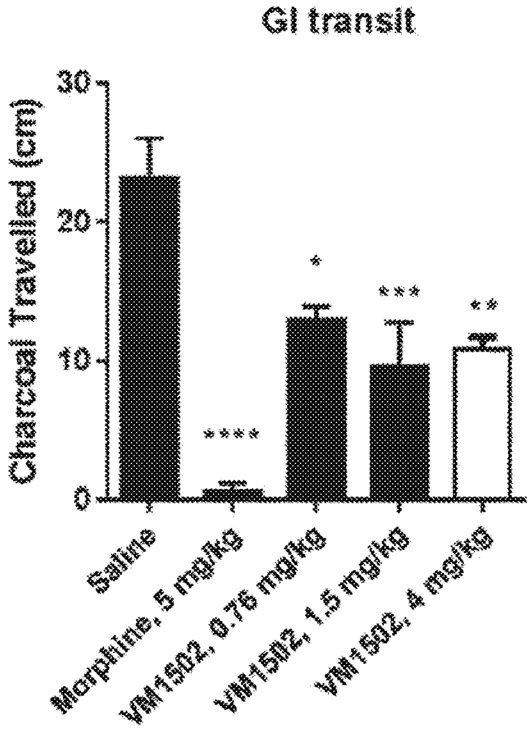
Figure 12D:
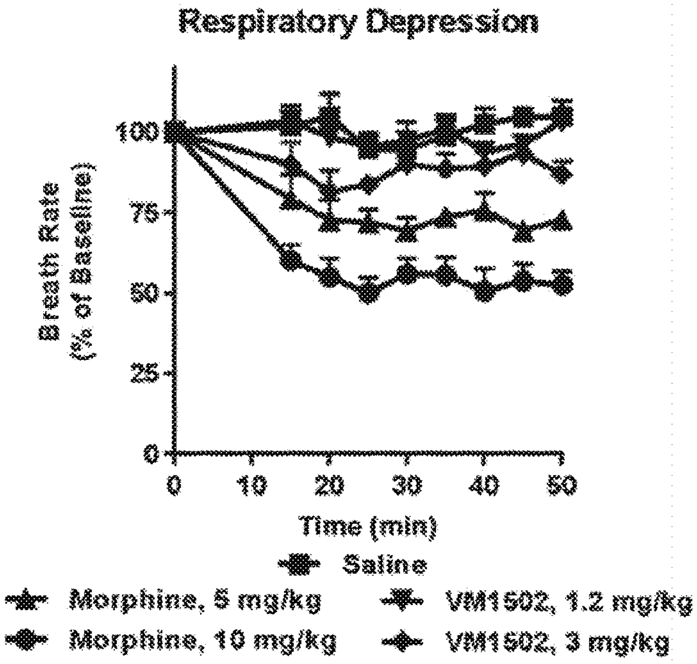
Figure 12E:
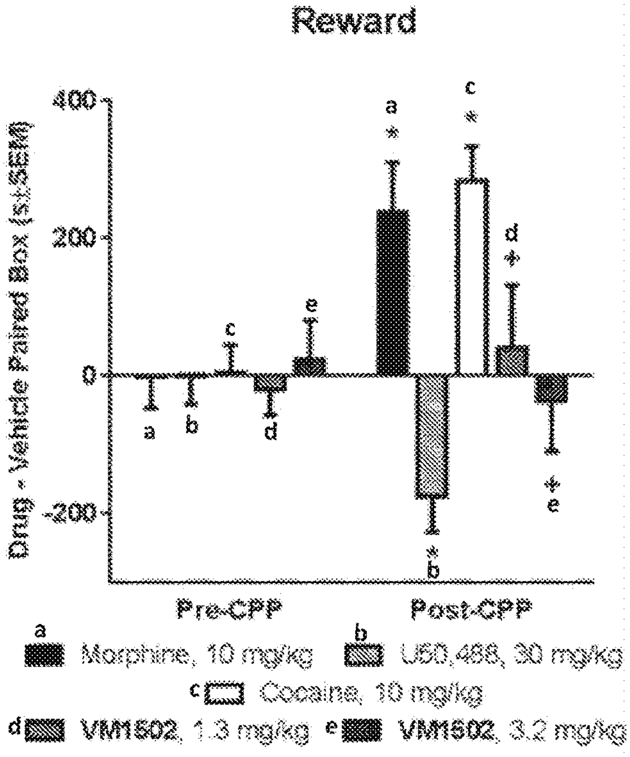

FIGS. 12A-12E show side effect studies with compound VM1502. FIG. 12A shows evaluation of tolerance: Mice were dosed 2× daily with 2× antinociceptive $ED_{50}$ with either morphine or VM1502 until they showed complete analgesic tolerance. VM1502 showed very slow onset of tolerance compared with morphine. *Significantly different from morphine (p<0.05). The experiment was replicated at least twice with similar results. FIG. 12B shows evaluation of physical dependence: Groups of mice were dosed 2× daily with 2× antinociceptive $ED_{50}$ with morphine or VM1502. Separate groups of mice were used for the 5, 22 and 29-day treatment with VM1502 and the animals within each group were sacrificed following the experiment with naloxone. Animals were challenged with naloxone (1 mg/kg) on day 5 of the morphine group, and days 5, 22, and 29 of the VM1502 groups. Number of jumps was counted over a 15 min period post-injection. The response of mice treated with VM1502 on either day was not significantly greater than that of mice treated with saline. *Significantly different from saline. (One-way ANOVA followed by Dunnett's multiple comparison test, p<0.05). FIG. 12C shows evaluation of Gastrointestinal transit. Groups of mice (n=10) received saline, morphine (5 mg/kg), or VM1502 (1.5 and 4 mg/kg) before receiving an oral dose of 0.2 mL of charcoal meal (2.5% gum tragacanth in 10% activated charcoal in water) by gavage. Animals were sacrificed 30 min later, and the distance traveled by charcoal was measured. VM1502 lowered transit significantly compared with saline (P<0.05) but less than morphine at both doses (P<0.05) as determined by ANOVA followed by Tukey's multiple-comparison test. The inhibition of gastrointestinal transit seems to plateau even at doses five times higher than the antinociceptive $ED_{50}$. FIG. 12D shows evaluation of respiratory rate. Animals were randomly assigned to receive saline (n=5), VM1502 (1.2 and 3 mg/kg, sc, n=5 at each dose), or morphine (5 and 10 mg/kg, n=5 at each dose). Each animal's baseline average breath rate was measured every 5 min for 25 min before drug injection, and breath rates after drug injection are expressed as a percent of baseline. Breath rates were measured for 50 minutes post-injection. While morphine caused respiratory depression at both 2× and 5× antinociceptive $ED_{50}$ dose (5 and 10 mg/kg, respectively), VM1502 did not depress respiratory rate at 2× antinociceptive $ED_{50}$ dose (1.2 mg/kg) and was not significantly different from saline at any time point, whereas morphine (5 mg/kg) decreased respiratory depression in comparison with VM1502 ($p<0.05$) as determined by repeated-measures ANOVA followed by Tukey's multiple-comparison test. However, at 5× antinociceptive $ED_{50}$ dose (3 mg/kg), VM1502 showed signs of respiratory depression albeit significantly less than the equianalgesic dose of morphine (10 mg/kg) at any given time point. (repeated-measures ANOVA followed by Tukey's multiple-comparison test). FIG. 12E shows evaluation of conditioned place-preference and aversion: Compound VM1502 alone did not produce conditioned place preference or aversion. After determination of initial preconditioning preferences, mice were place conditioned daily for 2 days with morphine (10 mg/kg/d, ip), U50,488 (30 mg/kg/d, ip), cocaine (10 mg/kg/d, ip) or VM1502 (1.3 mg/kg/d, ip and 3.2 mg/kg/d, ip). Mean difference in time spent on the drug-paired side t SEM is presented (n=17-21). *Significantly different from matching preconditioning preference ($p<0.05$); +significantly different from cocaine, morphine and U50,488 preference (two-way repeated measures ANOVA with Sidak's post hoc test).

Figure 13A:
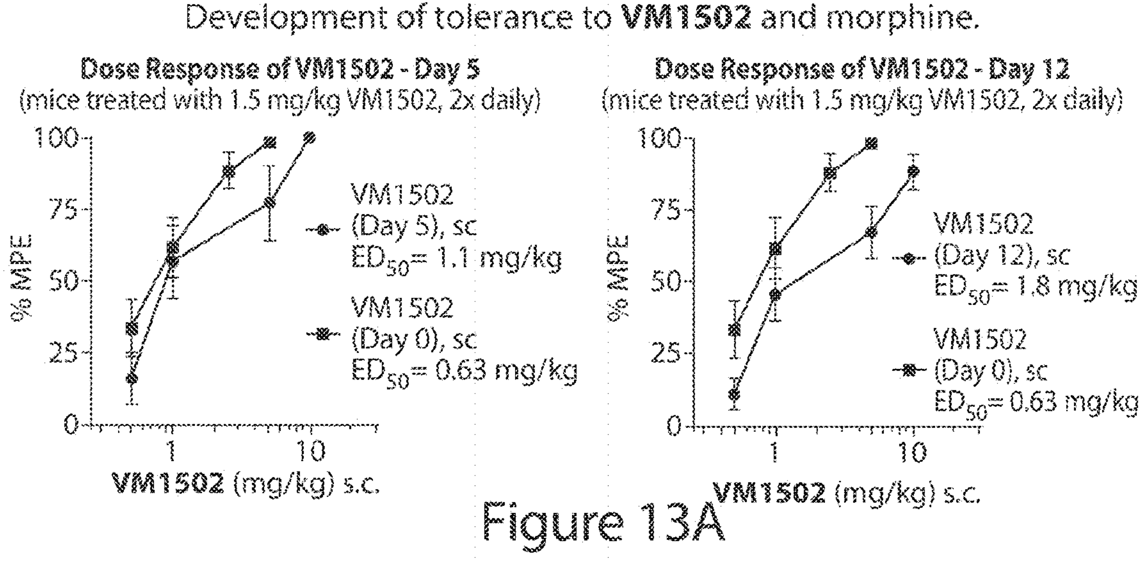
FIGS. 13A-13C show the development of tolerance in mice, to compound VM1502 and morphine.
Figure 13B:
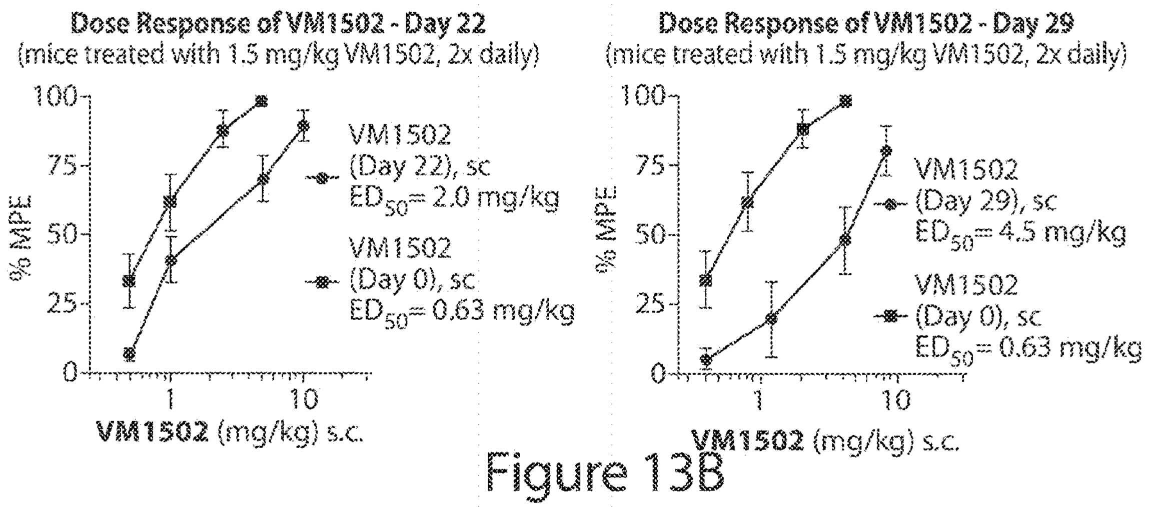
Figure 13C:
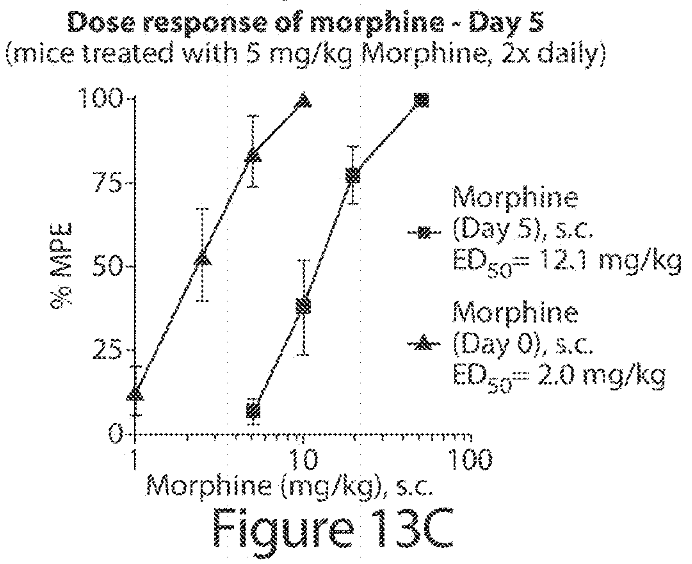

FIGS. 13A-13C shows the development of tolerance in mice, to compound VM1502 and morphine. FIG. 13A depicts the dose response curve on the group of mice treated with VM1502 on days 5 and 12. FIG. 13B depicts the dose response curve on the group of mice treated with VM1502 on days 22 and 29. FIG. 13C depicts the dose response curve on the group of mice treated with morphine on day 5. Groups of CD1 male mice (n=10) were treated with either morphine (2×$ED_{50}$, 5 mg/kg) or VM1502 (2×$ED_{50}$, 1.5 mg/kg) subcutaneously. Determinations of the cumulative dose-response curves were performed on the morphine group and VM1502 on day 5. Separate groups of CD1 mice (n=10 per group) were treated with VM1502 for 12, 22, and 29 days. Cumulative dose-response experiments were performed with VM1502 on the respective group on days 12, 22, and 29. The means of each dose in each determination were determined as percentage maximal possible effect (% MPE) [(observed latency−baseline latency)/(maximal latency−baseline latency)]×100. Each point represents mean t SEM for 10 mice. $ED_{50}$ values (and 95% confidence limits) were: Morphine, naïve (day 0): 2.0 mg/kg (1.2, 3.3); day 5: 12.1 mg/kg (7.6, 19.4). Compound VM1502: naïve (day 0): 0.63 mg/kg (0.42, 0.95); day 5: 1.1 mg/kg (0.66, 2.0); day 12: 1.8 mg/kg (1.2, 2.7); day 22: 2.0 mg/kg (1.4, 2.8); day 29: 4.5 mg/kg (2.7, 7.7).

FIG. 14 depicts the comparison of respiratory depression for animals dosed with compounds VM1502 and VM1512. Animals were randomly assigned to receive saline (n=5), VM1502 (3.75 mg/kg, sc, n=5), VM1512 (5.0 mg/kg, sc, n=5) or morphine (10 mg/kg, n=5). Each animal's baseline average breath rate was measured every 5 min for 25 min before drug injection, and breath rates after drug injection are expressed as a percent of baseline. Breath rates were measured for 50 minutes post-injection. Morphine caused respiratory depression at 5× antinociceptive $ED_{50}$ dose (5 and 10 mg/kg, respectively), VM1502 at 5× antinociceptive $ED_{50}$ dose (3.75 mg/kg) showed signs of respiratory depression albeit significantly less than the equianalgesic dose of morphine (10 mg/kg) at any given time point. However, at 5× antinociceptive $ED_{50}$ dose (5.0 mg/kg), VM1512 showed no signs respiratory depression compared to equianalgesic dose of morphine (10 mg/kg) and VM1502 at any given time point. (repeated-measures ANOVA followed by Tukey's multiple-comparison test).

Effects of Chronic administration: Mice were pelleted with morphine pellets (75 mg free base; NIDA) and tested for analgesia on Day 1 and 3. On Day 3 they also were tested with test compound (1 mg/kg, s.c.) for analgesia and with naloxone (1 mg/kg, s.c.) to precipitate withdrawal. A separate group of mice received test compound alone as a control for its analgesia in the morphine-tolerant mice. Similarly, group of mice (n=10) were made tolerant to test compound by twice daily injections to 1 mg/kg, s.c. for 10 days. On Day 10 they also were tested with test compound (1 mg/kg, s.c.) for analgesia and with naloxone (1 mg/kg, s.c.) and levallorphan (1 mg/kg) to precipitate withdrawal. Animals were evaluated for signs of diarrhea and jumping (Gistrak et al., *J. Pharmacol. Exp. Ther.,* 1989, 251 (2), 469-476).

Respiratory Depression assessment: The MouseOx Pulse Oximeter system (Starr Life Sciences, Pittsburgh, PA) was used to assess respiratory rate in awake, freely-moving, adult male CD1 mice. For 30 minutes, each animal was habituated to the device using a blank collar, after which the oximeter collar was placed on the animal. A five-second average breath rate was assessed at 5 minute intervals. A baseline for each animal was obtained over a 25 minute period prior to drug injection; beginning 15 minutes post-injection, measurements were then taken for a period of 35 minutes. Groups of mice (n=5) were treated subcutaneously with either morphine or test compound and breath rates were measured for both sets.[4] We have observed that compounds whose analgesia is E11 MOR-1 dependent and/or are G-protein biased MOR-1 agonists with DOR-1 antagonism exhibit useful analgesia, and improved side-effect profiles. (Varadi et al. *Eur. J. Med. Chem,* 2013, 69C, 786-789).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Majumdar, S.; Burgman, M.; Haselton, N.; Grinnell, S.; Ocampo, J.; Pasternak, A. R.; Pasternak, G. W. Generation of novel radiolabeled opiates through site-selective iodination. *Bioorg. Med. Chem. Lett.* 2011, 21, 4001-4004.
2. Majumdar, S.; Grinnell, S.; Le, R., V; Burgman, M.; Polikar, L.; Ansonoff, M.; Pintar, J.; Pan, Y. X.; Pasternak, G. W. Truncated G protein-coupled mu opioid receptor MOR-1 splice variants are targets for highly potent opioid analgesics lacking side effects. *Proc. Natl. Acad. Sci. U.S.A* 2011, 108, 19776-19783.
3. Pickett, J. E.; Váradi, A.; Palmer, T. C.; Grinnell, S. G.; Schrock, J. M.; Pasternak, G. W.; Karimov, R. R.; Majumdar, S. Mild, Pd-catalyzed stannylation of radioiodination targets. *Bioorganic & Medicinal Chemistry Letters* 2015, 25, 1761-1764.
4. Varadi, A.; Hosztafi, S.; Le, R., V; Toth, G.; Urai, A.; Noszal, B.; Pasternak, G. W.; Grinnell, S. G.; Majumdar, S. Novel 6beta-acylaminomorphinans with analgesic activity. *Eur. J. Med. Chem* 2013, 69C, 786-789.
5. Váradi, A.; Marrone, G. F.; Eans, S. O.; Ganno, M. L.; Subrath, J. J.; Le Rouzic, V.; Hunkele, A.; Pasternak, G. W.; McLaughlin, J. P.; Majumdar, S. Synthesis and Characterization of a Dual Kappa-Delta Opioid Receptor Agonist Analgesic Blocking Cocaine Reward Behavior. *ACS Chemical Neuroscience* 2015, 6, 1813-1824.
6. Majumdar, S.; Subrath, J.; Le Rouzic, V.; Polikar, L.; Burgman, M.; Nagakura, K.; Ocampo, J.; Haselton, N.; Pasternak, A. R.; Grinnell, S.; Pan, Y.-X.; Pasternak, G. W. Synthesis and evaluation of aryl-naloxamide opiate analgesics targeting truncated exon 11-associated mu opioid receptor (MOR-1) splice variants. *J. Med. Chem.* 2012, 55, 6352-6362.
7. Lowry, O. H.; Rosebrough, N. J.; Farr, A. L.; Randall, R. J. Protein measurement with the Folin phenol reagent. *J. Biol. Chem.* 1951, 193, 265-275.
8. Váradi, A.; Palmer, T. C.; Haselton, N.; Afonin, D.; Subrath, J. J.; Le Rouzic, V.; Hunkele, A.; Pasternak, G. W.; Marrone, G. F.; Borics, A.; Majumdar, S. Synthesis of Carfentanil Amide Opioids Using the Ugi Multicomponent Reaction. *ACS Chem Neurosci* 2015, 6, 1570-1577.
9. Haley, T. J.; McCormick, W. G. Pharmacological effects produced by intracerebral injection of drugs in the conscious mouse. *Br. J. Pharmacol. Chemother.* 1957, 12, 12-15.
10. Pasternak, K. R.; Rossi, G. C.; Zuckerman, A.; Pasternak, G. W. Antisense mapping KOR-1: evidence for multiple kappa analgesic mechanisms. *Brain Research* 1999, 826, 289-292.
11. Rossi, G. C.; Brown, G. P.; Leventhal, L.; Yang, K.; Pasternak, G. W. Novel receptor mechanisms for heroin and morphine-6b-glucuronide analgesia. *Neurosci. Lett.* 1996, 216, 1-4.
12. Rossi, G. C.; Standifer, K. M.; Pasternak, G. W. Differential blockade of morphine and morphine-6b-glucuronide analgesia by antisense oligodeoxynucleotides directed against MOR-1 and G-protein a subunits in rats. *Neurosci. Lett.* 1995, 198, 99-102.
13. Rossi, G. C.; Su, W.; Leventhal, L.; Su, H.; Pasternak, G. W. Antisense mapping DOR-1 in mice: further support for delta receptor subtypes. *Brain Res.* 1997, 753, 176-179.
14. Paul, D.; Pasternak, G. W. Differential blockade by naloxonazine of two m opiate actions: analgesia and inhibition of gastrointestinal transit. *Eur. J. Pharmacol.* 1988, 149, 403-404.
15. Gistrak, M. A.; Paul, D.; Hahn, E. F.; Pasternak, G. W. Pharmacological actions of a novel mixed opiate agonist/antagonist: naloxone benzoylhydrazone. *J. Pharmacol. Exp. Ther.* 1989, 251, 469-476.
16. Ponglux, D.; Wongseripipatana, S.; Takayama, H.; Kikuchi, M.; Kurihara, M.; Kitajima, M.; Aimi, N.; Sakai, S. A New Indole Alkaloid, 7 alpha-Hydroxy-7H-mitragynine, from *Mitragyna speciosa* in Thailand. *Planta Med* 1994, 60, 580-1.
17. Takayama, H.; Ishikawa, H.; Kurihara, M.; Kitajima, M.; Aimi, N.; Ponglux, D.; Koyama, F.; Matsumoto, K.; Moriyama, T.; Yamamoto, L. T.; Watanabe, K.; Murayama, T.; Horie, S. Studies on the synthesis and opioid agonistic activities of mitragynine-related indole alkaloids: discovery of opioid agonists structurally different from other opioid ligands. *Journal of Medicinal Chemistry* 2002, 45, 1949-56.

What is claimed is:

1. A compound of the formula:

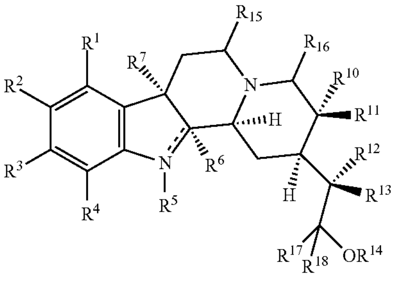

(I')

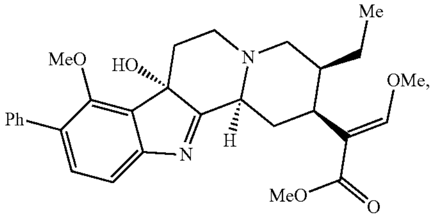 [SMILES: CC[C@@H]1CN2CC[C@@]3(O)C(=Nc4ccc(-c5ccccc5)c(OC)c43)[C@@H]2C[C@@H]1/C(=C\OC)C(=O)OC]

or a pharmaceutically acceptable salt or tautomer thereof, wherein:

is a single bond or double bond;

each of $R^1$, $R^2$, $R^3$, and $R^4$ is independently selected from the group consisting of hydrogen, halogen, —CN, —$NO_2$, —$N_3$, optionally substituted alkenyl, optionally substituted alkynyl, optionally substituted carbocyclyl, optionally substituted heterocyclyl, optionally substituted heteroaryl, —$OR^A$, —$N(R^B)_2$, —$SR^A$, —$SeR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, —S(═O)$R^C$, —$SO_2R^C$, —$NR^BSO_2R^C$, and —$SO_2N(R^B)_2$;

$R^5$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(═O)$R^C$, —C(═O)$OR^A$, —C(═O)$N(R^B)_2$, —S(═O)$R^C$, —$SO_2R^C$, —$SO_2N(R^B)_2$, or a nitrogen protecting group;

$R^6$ is hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —C(═O)$R^C$, —C(═O)$OR^A$, —C(═O)$N(R^B)_2$, —OC(═O)$R^C$, —OC(═O)$N(R^B)_2$, —$NR^B$C(═O)$R^C$, —$NR^B$C(═O)$OR^A$, —$NR^B$C(═O)$N(R^B)_2$, —S(═O)$R^C$, —$SO_2R^C$, —$NR^BSO_2R^C$, or —$SO_2N(R^B)_2$;

or $R^5$ and $R^6$ are absent and is a double bond;

provided that (i) $R^2$ is optionally substituted heteroaryl, and $R^7$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —OC(═O)$R^C$, —C(═O)$R^C$, —C(═O)$OR^A$, —OC(═O)$N(R^B)_2$, —C(═O)$N(R^B)_2$, —S(═O)$R^C$, —$SO_2R^C$, or —$SO_2N(R^B)_2$; or (ii) at least one of $R^1$, $R^2$, $R^3$, and $R^4$ is independently optionally substituted alkenyl, optionally substituted alkynyl, optionally substituted carbocyclyl, optionally substituted, monocyclic or bicyclic heterocyclyl, or optionally substituted heteroaryl, and $R^7$ is —OH;

each of $R^{10}$, $R^{11}$, $R^{12}$, and $R^{13}$ is independently selected from the group consisting of hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, and —$SR^A$;

or $R^{12}$ and $R^{13}$ are taken together to form an optionally substituted alkenyl moiety;

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of $R^{15}$ and $R^{16}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted aryl, optionally substituted heterocyclyl, optionally substituted heteroaryl, —CN, —$N_3$, —$OR^A$, —$N(R^B)_2$, and —$SR^A$;

each of $R^{17}$ and $R^{18}$ is independently selected from the group consisting of hydrogen, halogen, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, and —$SR^A$; or $R^{17}$ and $R^{18}$ are taken together to form

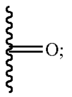

each instance of $R^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to oxygen, a sulfur protecting group when attached to sulfur, or a selenium protecting group when attached to selenium;

each instance of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group, or two $R^B$ groups are taken together with their intervening atoms to form an optionally substituted heterocyclic ring; and each instance of $R^C$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl.

2. The compound of claim 1, wherein the compound is of Formula (I):

(I)

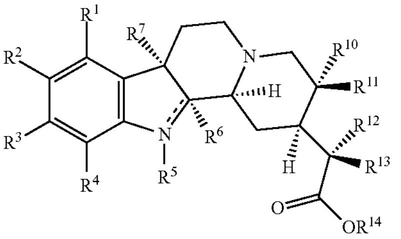

or a pharmaceutically acceptable salt or tautomer thereof.

3. The compound of claim 1, wherein the compound is of Formula (I-a):

(I-a)

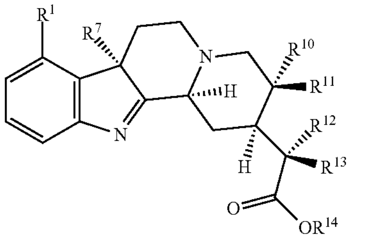

or a pharmaceutically acceptable salt or tautomer thereof.

4. A compound of one of the following formulae:

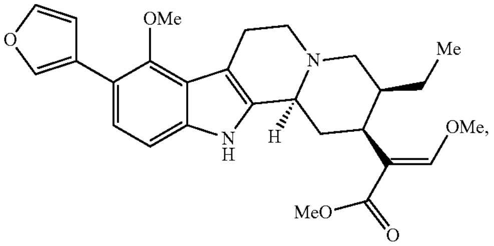

-continued

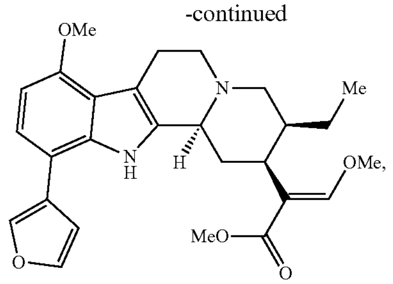

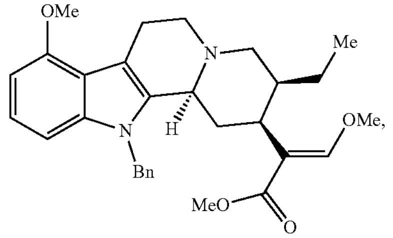

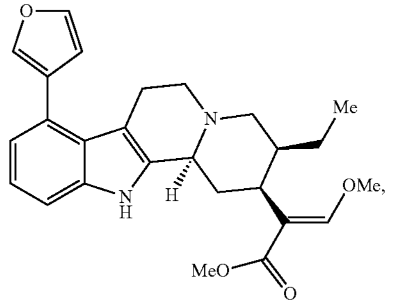

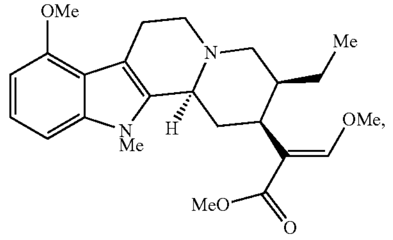

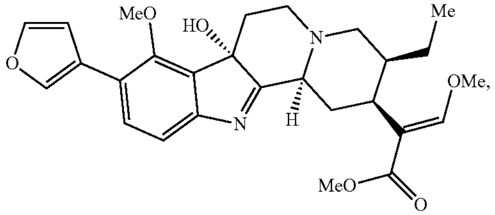

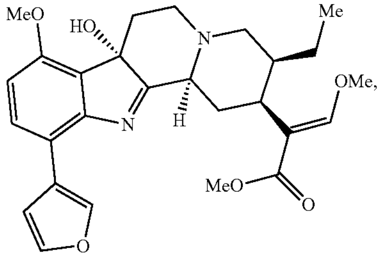

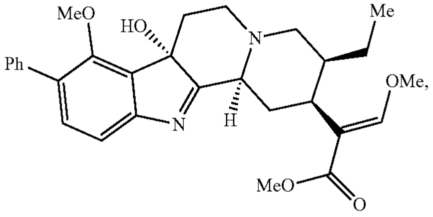

and

-continued

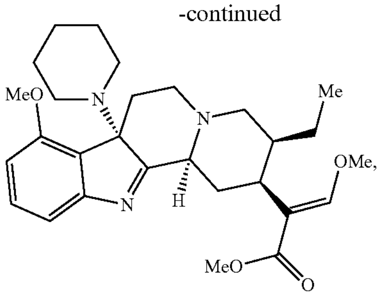

or a pharmaceutically acceptable salt or tautomer thereof.

5. A pharmaceutical composition comprising a compound of claim 1, or a pharmaceutically acceptable salt or tautomer thereof, and optionally a pharmaceutically acceptable carrier.

6. The compound of claim 1, wherein the compound is of Formula (I-b):

(I-b)

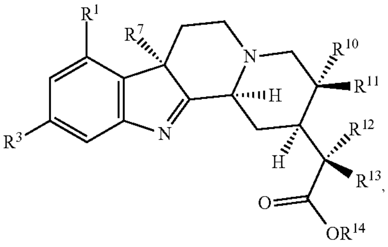

or a pharmaceutically acceptable salt or tautomer thereof.

7. The compound of claim 1, wherein the compound is of Formula (I-c):

(I-c)

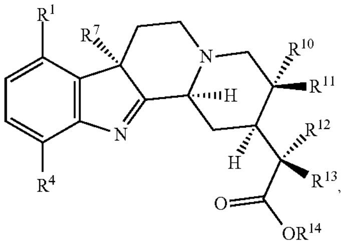

or a pharmaceutically acceptable salt or tautomer thereof.

8. The compound of claim 1, wherein the compound is of Formula (I-d):

(I-d)

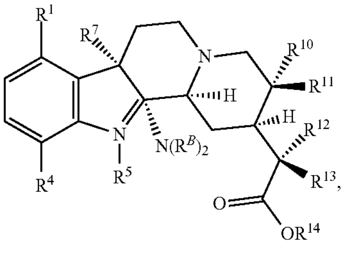

or a pharmaceutically acceptable salt thereof.

9. The compound of claim 1, or a pharmaceutically acceptable salt or tautomer thereof, wherein $R^1$ is optionally substituted heteroaryl.

10. The compound of claim 1, or a pharmaceutically acceptable salt or tautomer thereof, wherein $R^2$ is optionally substituted five-membered heteroaryl.

11. The compound of claim 1, or a pharmaceutically acceptable salt or tautomer thereof, wherein $R^3$ is hydrogen.

12. The compound of claim 1, or a pharmaceutically acceptable salt or tautomer thereof, wherein $R^4$ is optionally substituted heteroaryl.

13. The compound of claim 1, or a pharmaceutically acceptable salt or tautomer thereof, wherein is a single bond, and $R^5$ is hydrogen or optionally substituted alkyl.

14. The compound of claim 1, or a pharmaceutically acceptable salt or tautomer thereof, wherein is a single bond, and $R^6$ is hydrogen or optionally substituted alkyl.

15. The compound of claim 1, or a pharmaceutically acceptable salt or tautomer thereof, wherein is a single bond, and $R^7$ is hydrogen or —$OR^A$.

16. The compound of claim 1, or a pharmaceutically acceptable salt or tautomer thereof, wherein is a single bond, and $R^7$ is optionally substituted, monocyclic or bicyclic heterocyclyl.

17. The compound of claim 1, or a pharmaceutically acceptable salt or tautomer thereof, wherein is a double bond, and $R^5$ and $R^6$ are absent.

18. The compound of claim 1, or a pharmaceutically acceptable salt or tautomer thereof, wherein $R^{10}$ is hydrogen.

19. The compound of claim 1, or a pharmaceutically acceptable salt or tautomer thereof, wherein $R^{11}$ is optionally substituted alkyl.

20. The compound of claim 1, or a pharmaceutically acceptable salt or tautomer thereof, wherein $R^{12}$ and $R^{13}$ are taken together to form an optionally substituted alkenyl moiety.

21. The compound of claim 20, or a pharmaceutically acceptable salt or tautomer thereof, wherein $R^{12}$ and $R^{13}$ are taken together to form:

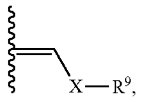

wherein:

X is O; and $R^9$ is optionally substituted alkyl.

22. The compound of claim 1, or a pharmaceutically acceptable salt or tautomer thereof, wherein $R^{14}$ is optionally substituted alkyl.

23. The compound of claim 1, or a pharmaceutically acceptable salt or tautomer thereof, wherein $R^1$ is $—OR^A$.

24. The compound of claim 1, or a pharmaceutically acceptable salt or tautomer thereof, wherein $R^1$ is $—OCH_3$.

25. The compound of claim 1, or a pharmaceutically acceptable salt or tautomer thereof, wherein $R^2$ is optionally substituted furanyl.

26. A pharmaceutical composition comprising a compound of claim 4, or a pharmaceutically acceptable salt or tautomer thereof, and optionally a pharmaceutically acceptable carrier.

27. A method of treating a painful condition comprising administering to a subject in need thereof a therapeutically effective amount of a compound according to claim 1, or a pharmaceutically acceptable salt or tautomer thereof.

28. A method of inducing analgesia in a subject comprising administering to the subject in need thereof a therapeutically effective amount of a compound according to claim 1, or a pharmaceutically acceptable salt or tautomer thereof.

29. A method of treating a neurological or psychiatric disease or condition in a subject comprising administering to the subject in need thereof a therapeutically effective amount of a compound according to claim 1, or a pharmaceutically acceptable salt or tautomer thereof.

30. A method of treating an inflammatory disease or condition in a subject comprising administering to the subject in need thereof a therapeutically effective amount of a compound according to claim 1, or a pharmaceutically acceptable salt or tautomer thereof.

31. A method of modulating opioid receptor activity in a subject comprising administering to the subject a therapeutically effective amount of a compound of claim 1, or a pharmaceutically acceptable salt or tautomer thereof.

32. A method of treating a painful condition comprising administering to a subject in need thereof a therapeutically effective amount of a compound according to claim 4, or a pharmaceutically acceptable salt or tautomer thereof.

33. A method of inducing analgesia in a subject comprising administering to the subject in need thereof a therapeutically effective amount of a compound according to claim 4, or a pharmaceutically acceptable salt or tautomer thereof.

34. A method of treating a neurological or psychiatric disease or condition in a subject comprising administering to the subject in need thereof a therapeutically effective amount of a compound according to claim 4, or a pharmaceutically acceptable salt or tautomer thereof.

35. A method of treating an inflammatory disease or condition in a subject comprising administering to the subject in need thereof a therapeutically effective amount of a compound according to claim 4, or a pharmaceutically acceptable salt or tautomer thereof.

36. A method of modulating opioid receptor activity in a subject comprising administering to the subject a therapeutically effective amount of a compound of claim 4, or a pharmaceutically acceptable salt or tautomer thereof.

37. A method of preparing a compound of claim 1 comprising coupling a compound of Formula (r-1):

(r-1)

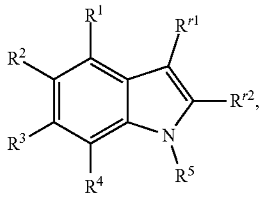

with a compound of Formula (r-2):

(r-2)

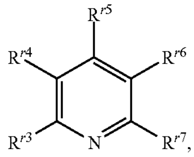

wherein each of $R^{r1}$, $R^{r2}$, $R^{r3}$, $R^{r4}$, $R^{r5}$, $R^{r6}$, and $R^{r7}$ is independently selected from the group consisting of hydrogen, halogen, —CN, $—NO_2$, $—N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, $—OR^A$, $—N(R^B)_2$, $—SR^A$, $—SeR^A$, $—C(=O)R^C$, $—C(=O)OR^A$, $—C(=O)N(R^B)_2$, $—OC(=O)R^C$, $—OC(=O)N(R^B)_2$, $—NR^BC(=O)R^C$, $—NR^BC(=O)OR^A$, $—NR^BC(=O)N(R^B)_2$, $S(=O)R^C$, $—SO_2R^C$, $—NR^BSO_2R^C$, and $—SO_2N(R^B)_2$.

* * * * *

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 1
cgccccagcc tcttcctct 19

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 2
aggggaaggt cgggtagg 18

<210> SEQ ID NO 3
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 3
cgccccgacc tcttccctt 19

<210> SEQ ID NO 4
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 4
gaggagaggt gcgtggag 18

<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
ctccgcgctc tcaccctct 19